US007422850B2

(12) United States Patent
Marshall et al.

(10) Patent No.: US 7,422,850 B2
(45) Date of Patent: Sep. 9, 2008

(54) MATERIALS AND METHODS FOR DETECTION OF NUCLEIC ACIDS

(75) Inventors: David J. Marshall, Madison, WI (US); James R. Prudent, Madison, WI (US); Christopher B. Sherrill, Madison, WI (US); Gideon Shapiro, Alachua, FL (US); Jennifer K. Grenier, Madison, WI (US); Craig S. Richmond, Madison, WI (US); Simona Jurczyk, Gainesville, FL (US); Jerod L. Ptacin, Beloit, WI (US)

(73) Assignee: Eragen Biosciences, Inc., Madison, WI (US)

( * ) Notice: Subject to any disclaimer, the term of this patent is extended or adjusted under 35 U.S.C. 154(b) by 295 days.

(21) Appl. No.: 09/861,292

(22) Filed: May 18, 2001

(65) Prior Publication Data
US 2002/0150900 A1 Oct. 17, 2002

Related U.S. Application Data

(60) Provisional application No. 60/282,831, filed on Apr. 10, 2001, provisional application No. 60/240,398, filed on Oct. 14, 2000, provisional application No. 60/205,712, filed on May 19, 2000.

(51) Int. Cl.
*C12Q 1/68* (2006.01)
(52) U.S. Cl. .................. 435/6; 435/91.1; 435/91.2
(58) Field of Classification Search ............... 435/6, 435/91.1, 91.2, 4; 536/23.1, 23.5, 24.3, 24.33
See application file for complete search history.

(56) References Cited

U.S. PATENT DOCUMENTS

| | | | | |
|---|---|---|---|---|
| 4,458,066 | A | 7/1984 | Caruthers et al. | 536/27 |
| 4,683,195 | A | 7/1987 | Mullis et al. | 435/6 |
| 4,683,202 | A | 7/1987 | Mullis et al. | 435/91 |
| 4,800,159 | A | 1/1989 | Mullis et al. | 435/172.3 |
| 4,996,143 | A | 2/1991 | Heller et al. | 435/6 |
| 5,210,015 | A * | 5/1993 | Gelfand et al. | 435/6 |
| 5,432,272 | A | 7/1995 | Benner | 536/25.3 |
| 5,843,669 | A * | 12/1998 | Kaiser et al. | 435/6 |
| 5,846,717 | A | 12/1998 | Brow et al. | 435/6 |
| 5,928,869 | A | 7/1999 | Nadeau et al. | 435/6 |
| 5,965,364 | A * | 10/1999 | Benner | 435/6 |
| 6,001,983 | A | 12/1999 | Benner | 536/23.1 |
| 6,007,984 | A | 12/1999 | Wang et al. | 435/6 |
| 6,037,120 | A | 3/2000 | Benner | 435/6 |
| 6,140,496 | A | 10/2000 | Benner | 536/27.1 |
| 6,232,462 | B1 * | 5/2001 | Collins et al. | 536/25.3 |
| 6,548,250 | B1 * | 4/2003 | Sorge | 435/6 |
| 6,833,257 | B2 * | 12/2004 | Lee et al. | 435/91.1 |

FOREIGN PATENT DOCUMENTS

| EP | 0416817 A2 | 10/1996 |
|---|---|---|
| EP | 0382433 A2 | 11/1997 |
| EP | 0915174 A1 | 5/1999 |

OTHER PUBLICATIONS

Newton et al. (Nuc. Acid res. (1993) 21(5): 1155-1162).*
Switzer et al. Enzymatic recognition of the base pair between isocytidine and isoguanosine. 1993. Biochemistry vol. 32:10489-10496.*
Narang et al. (1979) *Methods in Enzymology* 68:90.
Brown et al. (1979) *Methods in Enzymology* 68:109.
Beaucage et al. (1981) *Tetrahedron Letters* 22:1859.
Ren et al. (1996) *J. Am. Chem. Soc.* 118, 7671.
McMinn et al. (1999) *J. Am. Chem. Soc.* 121, 11585.
Hosfeld et al. *J. Biol. Chem* (1998) 273:27154-61.
Bult et al. *Science* (1996) 273:1058-73.
Newton, et al., "The Production of PCR Products with 5' Single-Stranded Tails Using Primers That Incorporate Novel Phosphoramidite Intermediates," *Nucleic Acids Research* vol. 21, No. 5, pp. 1155-1162, 1993. Oxford University Press, Surrey, GB.
Livak, et al., "Oligonucleotides with Fluorescent Dyes at Opposite Ends Provide a Quenched Probe System Useful for Detecting PCR Product and Nucleic Acid Hybridization," *PCR Methods and Applications* (4) No. 6, pp. 357-362, 1995. U.S.
Cantor, "Lighting up Hybridization," *Nature Biotechnology* (14) No. 1, p. 247, 1996. Nature Publishing, U.S.
Whitcombe, et al., "Detection of PCR Products Using Self-Probing Amplicons and Fluorescence," *Nature Biotech*, (17) No. 8, pp. 804-807, 1999. Nature Publishing, U.S.
International Search Report for PCT/US01/16359.
Cobianchi, F. and Wilson, S. H., "Enzymes for Modifying and Labeling DNA and RNA," in *Methods in Enzymology*, (Berger,S.L. and Kimmel, A.R., Eds.) vol. 152, pp. 94-100, Academic Press, NY (1987).

(Continued)

*Primary Examiner*—Gary Benzion
*Assistant Examiner*—Heather G. Calamita
(74) *Attorney, Agent, or Firm*—Foley & Lardner LLP

(57) ABSTRACT

Assays using non-natural bases are described. In one embodiment, the method involves contacting a sample suspected of containing the target nucleic acid with a polymerase and first and second primers; amplifying the target nucleic acid, if present in the sample, by PCR using the first and second primers to generate an amplification product having a double-stranded region and a single-stranded region that comprises the non-natural base; contacting the sample with a reporter comprising a label and a non-natural base that is complementary to the non-natural base of the single-stranded region; annealing at least a portion of the reporter to the single-stranded region of the amplification product; cleaving, after annealing, at least a portion of the reporter to release at least one reporter fragment; and correlating the release of the at least one reporter fragment with the presence of the target nucleic acid in the sample. The invention also provides corresponding kits for use in detecting target nucleic acids in a sample. Alternatively, the reporter can be incorporated into the amplification product rather than annealing and then cleaving.

16 Claims, 24 Drawing Sheets

OTHER PUBLICATIONS

Roberts et al., Theoretical and Experimental Study of Isoguanine and Isocytosine: Base Pairing in an Expanded Genetic System, *J. Am. Chem. Soc.*, vol. 199 pp. 4640-4649 (1997).

Jurczyk et al., "Synthesis of 2'-Deoxyisoguanosine 5'-Triphosphate and 2'-Deoxy-5-methylisocytosine 5'-Triphosphate," *Helvetica Chimica Acta*, vol. 82 pp. 1005-1015 (1999).

Ogawa et al., "Efforts toward the Expansion of the Genetic Alphabet: Information Storage and Replication with Unnatural Hydrophobic Base Pairs," *J. Am. Chem. Soc.*, vol. 122 pp. 3274-3287 (2000).

Tor, Yitzhak and Dervan, Peter B., Site Specific Enzymatic Incorporation of an Unnatural Base, N6-(6-Aminohexyl)isoguanosine, into RNA, J. Am. Chem. Soc. 115:4461-4467 (1993).

* cited by examiner

SEQUENCE LISTING

```
<160> NUMBER OF SEQ ID NOS: 41

<210> SEQ ID NO 1
<211> LENGTH: 12
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents deoxy-iso-guanine (d-isoG)
<220> FEATURE:
<221> NAME/KEY: modified_base
<222> LOCATION: (3)..(3)
<223> OTHER INFORMATION: n represents
      5'-5-[N-4'-carboxy-4(dimethylamino)-azobenzene)-aminohexyl-3-acry
      limido]-2'-deoxyUridine
<220> FEATURE:
<221> NAME/KEY: modified_base
<222> LOCATION: (12)..(12)
<223> OTHER INFORMATION: n represents deoxycytidylate 3' labeled with
      BiotinTEG CPG

<400> SEQUENCE: 1
tnncctgtct gn                                                         12
```

```
<210> SEQ ID NO 2
<211> LENGTH: 15
<212> TYPE: DNA
<213> ORGANISM: Artificial
<220> FEATURE:
<223> OTHER INFORMATION: synthetic oligonucleotide

<400> SEQUENCE: 2
ggccagcata agccm                                                          15

<210> SEQ ID NO 3
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (11)..(11)
<223> OTHER INFORMATION: n represents deoxy-iso-cytosine (d-isoC)

<400> SEQUENCE: 3
gcagacagga naccatcagc tgttttcgtt g                                        31

<210> SEQ ID NO 4
<211> LENGTH: 15
<212> TYPE: DNA
<213> ORGANISM: Artificial
<220> FEATURE:
<223> OTHER INFORMATION: synthetic oligonucleotide

<400> SEQUENCE: 4
ggccagcata agccc                                                          15

<210> SEQ ID NO 5
<211> LENGTH: 15
<212> TYPE: DNA
<213> ORGANISM: Artificial
<220> FEATURE:
<223> OTHER INFORMATION: synthetic oligonucleotide

<400> SEQUENCE: 5
ggccagcata agcca                                                          15

<210> SEQ ID NO 6
<211> LENGTH: 45
<212> TYPE: DNA
<213> ORGANISM: Artificial
<220> FEATURE:
<223> OTHER INFORMATION: synthetic oligonucleotide

<400> SEQUENCE: 6
tgaatttcca gtcttgcaag caaagtgact agcttgacgt aaggg                         45

<210> SEQ ID NO 7
<211> LENGTH: 45
<212> TYPE: DNA
<213> ORGANISM: Artificial
<220> FEATURE:
<223> OTHER INFORMATION: synthetic oligonucleotide

<400> SEQUENCE: 7
cccttacgtc aagctagtca ctttgcttgc aagactggaa attca                         45

<210> SEQ ID NO 8
<211> LENGTH: 45
<212> TYPE: DNA
```

```
<213> ORGANISM: Artificial
<220> FEATURE:
<223> OTHER INFORMATION: synthetic oligonucleotide

<400> SEQUENCE: 8
tgaatttcca gtcttgcaag caaattgact agcttgacgt aaggg            45

<210> SEQ ID NO 9
<211> LENGTH: 45
<212> TYPE: DNA
<213> ORGANISM: Artificial
<220> FEATURE:
<223> OTHER INFORMATION: synthetic oligonucleotide

<400> SEQUENCE: 9
cccttacgtc aagctagtca atttgcttgc aagactggaa attca             45

<210> SEQ ID NO 10
<211> LENGTH: 21
<212> TYPE: DNA
<213> ORGANISM: Artificial
<220> FEATURE:
<223> OTHER INFORMATION: synthetic oligonucleotide

<400> SEQUENCE: 10
cccttacgtc aagctagtca c                                       21

<210> SEQ ID NO 11
<211> LENGTH: 21
<212> TYPE: DNA
<213> ORGANISM: Artificial
<220> FEATURE:
<223> OTHER INFORMATION: synthetic oligonucleotide

<400> SEQUENCE: 11
cccttacgtc aagctagtca a                                       21

<210> SEQ ID NO 12
<211> LENGTH: 22
<212> TYPE: DNA
<213> ORGANISM: Artificial
<220> FEATURE:
<223> OTHER INFORMATION: synthetic oligonucleotide

<400> SEQUENCE: 12
tgaatttcca gtcttgcaag ca                                      22

<210> SEQ ID NO 13
<211> LENGTH: 12
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxy-iso-cytosine (d-isoC)
<220> FEATURE:
<221> NAME/KEY: modified_base
<222> LOCATION: (2)..(2)
<223> OTHER INFORMATION: n represents deoxy-iso-guanine (d-isoG)
<220> FEATURE:
<221> NAME/KEY: modified_base
<222> LOCATION: (3)..(3)
<223> OTHER INFORMATION: n represents
      (5'-5-[(N-4'-carboxy-4(dimethylamino)-azobenzene)-aminohexyl-3-ac
      rylimido]-2'-deoxyUridine
<220> FEATURE:
<221> NAME/KEY: modified_base
```

```
<222> LOCATION: (12)..(12)
<223> OTHER INFORMATION: n represents deoxycytidylate 3' labeled with
      BiotinTEG CPG

<400> SEQUENCE: 13
nnncctgtct gn                                                            12

<210> SEQ ID NO 14
<211> LENGTH: 17
<212> TYPE: DNA
<213> ORGANISM: Artificial
<220> FEATURE:
<223> OTHER INFORMATION: synthetic oligonucleotide

<400> SEQUENCE: 14
ctcatggacc cccatac                                                       17

<210> SEQ ID NO 15
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (11)..(11)
<223> OTHER INFORMATION: n represents deoxy-iso-cytosine (d-isoC)

<400> SEQUENCE: 15
gcagacagga nagctaactg gagcgtgg                                           28

<210> SEQ ID NO 16
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (11)..(11)
<223> OTHER INFORMATION: n represents deoxy-iso-cytosine (d-isoC)
<220> FEATURE:
<221> NAME/KEY: modified_base
<222> LOCATION: (12)..(12)
<223> OTHER INFORMATION: n represents deoxy-iso-guanine (d-isoG)

<400> SEQUENCE: 16
gcagacagga nngctaactg gagcgtgg                                           28

<210> SEQ ID NO 17
<211> LENGTH: 41
<212> TYPE: DNA
<213> ORGANISM: Artificial
<220> FEATURE:
<223> OTHER INFORMATION: synthetic oligonucleotide

<400> SEQUENCE: 17
cctcatggac ccccatacat attgtccacg ctccagttag c                            41

<210> SEQ ID NO 18
<211> LENGTH: 25
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents deoxy-iso-guanine (d-isoG)
```

```
<220> FEATURE:
<221> NAME/KEY: modified_base
<222> LOCATION: (6)..(6)
<223> OTHER INFORMATION: n represents deoxy-iso-guanine (d-isoG)
<220> FEATURE:
<221> NAME/KEY: misc_feature
<222> LOCATION: (11)..(11)
<223> OTHER INFORMATION: n represents a n-propylene spacer (c3)

<400> SEQUENCE: 18
gtnatntgcg ntcgtgcggt gcgtc                                   25

<210> SEQ ID NO 19
<211> LENGTH: 18
<212> TYPE: DNA
<213> ORGANISM: Artificial
<220> FEATURE:
<223> OTHER INFORMATION: synthetic oligonucleotide

<400> SEQUENCE: 19
tagcctgctg tgctgtgt                                           18

<210> SEQ ID NO 20
<211> LENGTH: 18
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents deoxy-iso-cytosine (d-isoC)

<400> SEQUENCE: 20
tngcctgctg tgctgtgt                                           18

<210> SEQ ID NO 21
<211> LENGTH: 30
<212> TYPE: DNA
<213> ORGANISM: Artificial
<220> FEATURE:
<223> OTHER INFORMATION: synthetic oligonucleotide

<400> SEQUENCE: 21
tcgtgcggtg cgtcacacag cacagcaggc                              30

<210> SEQ ID NO 22
<211> LENGTH: 16
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents deoxy-iso-guanine (d-isoG)
<220> FEATURE:
<221> NAME/KEY: modified_base
<222> LOCATION: (3)..(3)
<223> OTHER INFORMATION: n represents
      (5'-5-[N-4'-carboxy-4(dimethylamino-azobenzene)-aminohexyl-3-acry
      limido]-2'-deoxyUridine
<220> FEATURE:
<221> NAME/KEY: modified_base
<222> LOCATION: (16)..(16)
<223> OTHER INFORMATION: n represents deoxythymidylate 3' labeled with
      BiotinTEG CPG

<400> SEQUENCE: 22
tnncctgtct gcctgn                                             16
```

<210> SEQ ID NO 23
<211> LENGTH: 25
<212> TYPE: DNA
<213> ORGANISM: Artificial
<220> FEATURE:
<223> OTHER INFORMATION: synthetic oligonucleotide

<400> SEQUENCE: 23
gataatcagt agctttgtaa ccctg                                    25

<210> SEQ ID NO 24
<211> LENGTH: 21
<212> TYPE: DNA
<213> ORGANISM: Artificial
<220> FEATURE:
<223> OTHER INFORMATION: synthetic oligonucleotide

<400> SEQUENCE: 24
gtggcacaag attgatggaa t                                        21

<210> SEQ ID NO 25
<211> LENGTH: 41
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (19)..(19)
<223> OTHER INFORMATION: n represents deoxy-iso-cytosine (d-isoC)
<220> FEATURE:
<221> NAME/KEY: modified_base
<222> LOCATION: (20)..(20)
<223> OTHER INFORMATION: n represents deoxy-iso-guanine (d-isoG)

<400> SEQUENCE: 25
cacgacaggc agacaggann cccaccaact gtttactgta c                  41

<210> SEQ ID NO 26
<211> LENGTH: 35
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (15)..(15)
<223> OTHER INFORMATION: n represents deoxy-iso-cytosine (d-isoC)
<220> FEATURE:
<221> NAME/KEY: modified_base
<222> LOCATION: (16)..(16)
<223> OTHER INFORMATION: n represents deoxy-iso-guanine (d-isoG)

<400> SEQUENCE: 26
acaggcagac aggannagga ccttgctgca gtaac                         35

<210> SEQ ID NO 27
<211> LENGTH: 16
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents deoxy-iso-guanine (d-isoG)
<220> FEATURE:
<221> NAME/KEY: modified_base
<222> LOCATION: (3)..(3)

```
<223> OTHER INFORMATION: n represents
     (5'-5-[(N-4'-carboxy-4(dimethylamino)-azobenzene)-aminohexyl-3-ac
     rylimido]-2'-deoxyUridine
<220> FEATURE:
<221> NAME/KEY: modified_base
<222> LOCATION: (16)..(16)
<223> OTHER INFORMATION: n represents deoxythymidylate 3' labeled with
     BiotinTEG CPG

<400> SEQUENCE: 27
tnncctgtct gcctgn                                                   16

<210> SEQ ID NO 28
<211> LENGTH: 16
<212> TYPE: DNA
<213> ORGANISM: Artificial
<220> FEATURE:
<223> OTHER INFORMATION: synthetic oligonucleotide

<400> SEQUENCE: 28
gcgcggcgat atcatc                                                   16

<210> SEQ ID NO 29
<211> LENGTH: 35
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (19)..(19)
<223> OTHER INFORMATION: n represents deoxy-iso-cytosine (d-isoC)
<220> FEATURE:
<221> NAME/KEY: modified_base
<222> LOCATION: (20)..(20)
<223> OTHER INFORMATION: n represents deoxy-iso-guanine (d-isoG)

<400> SEQUENCE: 29
cacgacaggc agacaggann cgccagctca ccatg                              35

<210> SEQ ID NO 30
<211> LENGTH: 17
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents deoxy-iso-cytosine (d-isoC)

<400> SEQUENCE: 30
tncgccagct caccatg                                                  17

<210> SEQ ID NO 31
<211> LENGTH: 12
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents deoxy-iso-guanine (d-isoG)
<220> FEATURE:
<221> NAME/KEY: modified_base
<222> LOCATION: (3)..(3)
<223> OTHER INFORMATION: n represents
     (5'-5-[(N-4'-carboxy-4(dimethylamino)-azobenzene)-aminohexyl-3-ac
     rylimido]-2'-deoxyUridine
<220> FEATURE:
```

```
<221> NAME/KEY: modified_base
<222> LOCATION: (12)..(12)
<223> OTHER INFORMATION: n represents deoxyguanylate 3' labeled with
      BiotinTEG CPG

<400> SEQUENCE: 31
tnnggacaga cn                                                              12

<210> SEQ ID NO 32
<211> LENGTH: 18
<212> TYPE: DNA
<213> ORGANISM: Artificial
<220> FEATURE:
<223> OTHER INFORMATION: synthetic oligonucleotide

<400> SEQUENCE: 32
gagcagtcgg tcagtgac                                                        18

<210> SEQ ID NO 33
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (11)..(11)
<223> OTHER INFORMATION: n represents deoxy-iso-cytosine (d-isoC)
<220> FEATURE:
<221> NAME/KEY: modified_base
<222> LOCATION: (12)..(12)
<223> OTHER INFORMATION: n represents deoxy-iso-guanine (d-isoG)

<400> SEQUENCE: 33
cgtctgtcca nngagctagc ggaggcc                                              27

<210> SEQ ID NO 34
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (11)..(11)
<223> OTHER INFORMATION: n represents deoxy-iso-cytosine (d-isoC)
<220> FEATURE:
<221> NAME/KEY: modified_base
<222> LOCATION: (12)..(12)
<223> OTHER INFORMATION: n represents deoxy-iso-guanine (d-isoG)

<400> SEQUENCE: 34
gcagacagga nnggagctag cggaggct                                             28

<210> SEQ ID NO 35
<211> LENGTH: 26
<212> TYPE: DNA
<213> ORGANISM: Artificial
<220> FEATURE:
<223> OTHER INFORMATION: synthetic oligonucleotide

<400> SEQUENCE: 35
atttctgaaa ggttacttca aggaca                                               26

<210> SEQ ID NO 36
<211> LENGTH: 33
<212> TYPE: DNA
<213> ORGANISM: Artificial
<220> FEATURE:
```

```
<223> OTHER INFORMATION: synthetic oligonucleotide
<220> FEATURE:
<221> NAME/KEY: modified_base
<222> LOCATION: (15)..(15)
<223> OTHER INFORMATION: n represents deoxy-iso-cytosine (d-isoC)
<220> FEATURE:
<221> NAME/KEY: modified_base
<222> LOCATION: (16)..(16)
<223> OTHER INFORMATION: n represents deoxy-iso-guanine (d-isoG)

<400> SEQUENCE: 36
tgtccgtctg tccannagat ccctggacag gca                               33

<210> SEQ ID NO 37
<211> LENGTH: 32
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (15)..(15)
<223> OTHER INFORMATION: n represents deoxy-iso-cytosine (d-isoC)
<220> FEATURE:
<221> NAME/KEY: modified_base
<222> LOCATION: (16)..(16)
<223> OTHER INFORMATION: n represents deoxy-iso-guanine (d-isoG)

<400> SEQUENCE: 37
acaggcagac agganngatc cctggacagg cg                                32

<210> SEQ ID NO 38
<211> LENGTH: 70
<212> TYPE: DNA
<213> ORGANISM: Artificial
<220> FEATURE:
<223> OTHER INFORMATION: synthetic oligonucleotide

<400> SEQUENCE: 38
atttctgaaa ggttacttca aggacaaaat acctgtattc ctcgcctgtc cagggatctg   60
ctcttacaga                                                         70

<210> SEQ ID NO 39
<211> LENGTH: 70
<212> TYPE: DNA
<213> ORGANISM: Artificial
<220> FEATURE:
<223> OTHER INFORMATION: synthetic oligonucleotide

<400> SEQUENCE: 39
atttctgaaa ggttacttca aggacaaaat acctgtattc cttgcctgtc cagggatctg   60
ctcttacaga                                                         70

<210> SEQ ID NO 40
<211> LENGTH: 31
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (15)..(15)
<223> OTHER INFORMATION: n represents deoxy-iso-cytosine (d-isoC)
<220> FEATURE:
<221> NAME/KEY: modified_base
<222> LOCATION: (16)..(16)
<223> OTHER INFORMATION: n represents deoxy-iso-guanine (d-isoG)

<400> SEQUENCE: 40
```

-continued

```
tgtccgtctg tccanngagc tagcggaggc c                               31

<210> SEQ ID NO 41
<211> LENGTH: 32
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (15)..(15)
<223> OTHER INFORMATION: n represents deoxy-iso-cytosine (d-isoC)
<220> FEATURE:
<221> NAME/KEY: modified_base
<222> LOCATION: (16)..(16)
<223> OTHER INFORMATION: n represents deoxy-iso-guanine (d-isoG)

<400> SEQUENCE: 41
acaggcagac aggannggag ctagcggagg ct                              32
```

MATERIALS AND METHODS FOR DETECTION OF NUCLEIC ACIDS

CROSS-REFERENCE TO RELATED APPLICATION

This application claims the benefit of Provisional Applications Ser. Nos. 60/205,712, filed May 19, 2000, 60/240,398, filed Oct. 14, 2000, and 60/282,831, filed Apr. 10, 2001, all of which are hereby expressly incorporated by reference.

BACKGROUND OF THE INVENTION

Polymerase chain reaction (PCR) is a method for the enzymatic amplification of specific segments of DNA. The PCR is based on repeated cycles of the following basic steps: denaturation of double-stranded DNA, followed by oligonucleotide primer annealing to the DNA template, and primer extension by a nucleic acid polymerase (Mullis et al and Saiki et al. 1985; and U.S. Pat. Nos. 4,683,195, 4,683,202, and 4,800,159, the entire disclosures of which are incorporated herein by reference). The oligonucleotide primers used in PCR are designed to anneal to opposite strands of the DNA, and are positioned so that the nucleic acid polymerase-catalyzed extension product of one primer can serve as the template strand for the other primer. The PCR amplification process results in the exponential increase of discrete DNA fragments whose length is defined by the 5' ends of the oligonucleotide primers.

While the PCR technique as presently practiced is an extremely powerful method for amplifying nucleic acid sequences, the detection of the amplified material typically requires additional manipulation and subsequent handling of the PCR products to determine whether the target DNA is present. It is desirable to develop new methods and assays.

U.S. Pat. No. 5,210,015, incorporated herein by reference, teaches a method for detecting a target nucleic acid using labeled oligonucleotides. The process uses a polymerase with 5' to 3' nuclease activity to cleave annealed labeled oligonucleotide probe which can then be detected.

U.S. Pat. No. 5,846,717, incorporated herein by reference, teaches a method for detection of a target nucleic acid by forming a nucleic acid cleavage structure on the target sequence and then cleaving the nucleic acid cleavage structure in a site-specific manner using an enzyme with 5' nuclease activity.

U.S. Pat. No. 5,432,272, incorporated herein by reference, discloses non-standard bases that base pair in DNA or RNA but with a hydrogen bonding pattern different from the pattern observed with standard A:T or G:C base pairs.

SUMMARY OF THE INVENTION

The subject invention concerns materials and methods for the rapid detection of a target nucleic acid. Methods of the invention employ a reporter oligonucleotide; a nucleic acid polymerase; and first and second oligonucleotide primers, where at least one of the first and second oligonucleotide primers contains at least one non-natural base.

In one embodiment, the invention provides a method for detecting a target nucleic acid in a sample, the method comprising contacting the sample with a nucleic acid polymerase, a first oligonucleotide primer comprising a sequence complementary to a first portion of the target nucleic acid, a second oligonucleotide primer comprising a first region and a second region, the first region comprising a sequence complementary to a second portion of the target nucleic acid and the second region comprising a non-natural base; amplifying the target nucleic acid, if present in the sample, by PCR using the first and second oligonucleotide primers to generate an amplification product having (i) a double-stranded region and (ii) a single-stranded region that comprises the non-natural base; contacting the sample with a reporter comprising a label and a non-natural base that is complementary to the non-natural base of the single-stranded region; annealing at least a portion of the reporter to the single-stranded region of the amplification product; cleaving, after annealing, at least a portion of the reporter to release at least one reporter fragment; and correlating the release of the at least one reporter fragment with the presence of the target nucleic acid in the sample.

In another embodiment, the invention provides a method for detecting a target nucleic acid in a sample, the method comprising contacting the sample with a nucleic acid polymerase, a first oligonucleotide primer comprising a sequence complementary to a first portion of the target nucleic acid, a second oligonucleotide primer comprising a first region and a second region, the first region comprising a sequence complementary to a second portion of the target nucleic acid and the second region comprising a non-natural base; amplifying the target nucleic acid, if present in the sample, by PCR using the first and second oligonucleotide primers to generate an amplification product having (i) a double-stranded region and (ii) a single-stranded region that comprises the non-natural base; contacting the sample with a reporter comprising a label and a non-natural base that is complementary to the non-natural base of the single-stranded region; incorporating the reporter into the amplification product opposite the non-natural base of the single-stranded region; and correlating the incorporating of the reporter with the presence of the target nucleic acid in the sample.

In yet another embodiment, the invention provides kits for detection of target nucleic acid. In one embodiment, the kit comprises a nucleic acid polymerase; a first oligonucleotide primer comprising a sequence complementary to a first portion of the target nucleic acid; a second oligonucleotide primer comprising a first region and a second region, the first region comprising a sequence complementary to a second portion of the target nucleic acid and the second region comprising a non-natural base; and a reporter comprising a label and a non-natural base that is complementary to the non-natural base of the single-stranded region. Optionally, the kit further comprises other components such as buffers and reagents to perform the methods of the invention.

The methods of the invention can be incorporated into a variety of mass screening techniques and readout platforms.

BRIEF DESCRIPTION OF THE DRAWINGS

The invention may be more completely understood in consideration of the following detailed description of various embodiments of the invention in connection with the accompanying drawings, in which:

In FIG. 23A HEX fluorescence RFUs are shown on the Y axis; in FIG. 23B FAM fluorescence RFUs are shown on the Y axis.

Figure 1:
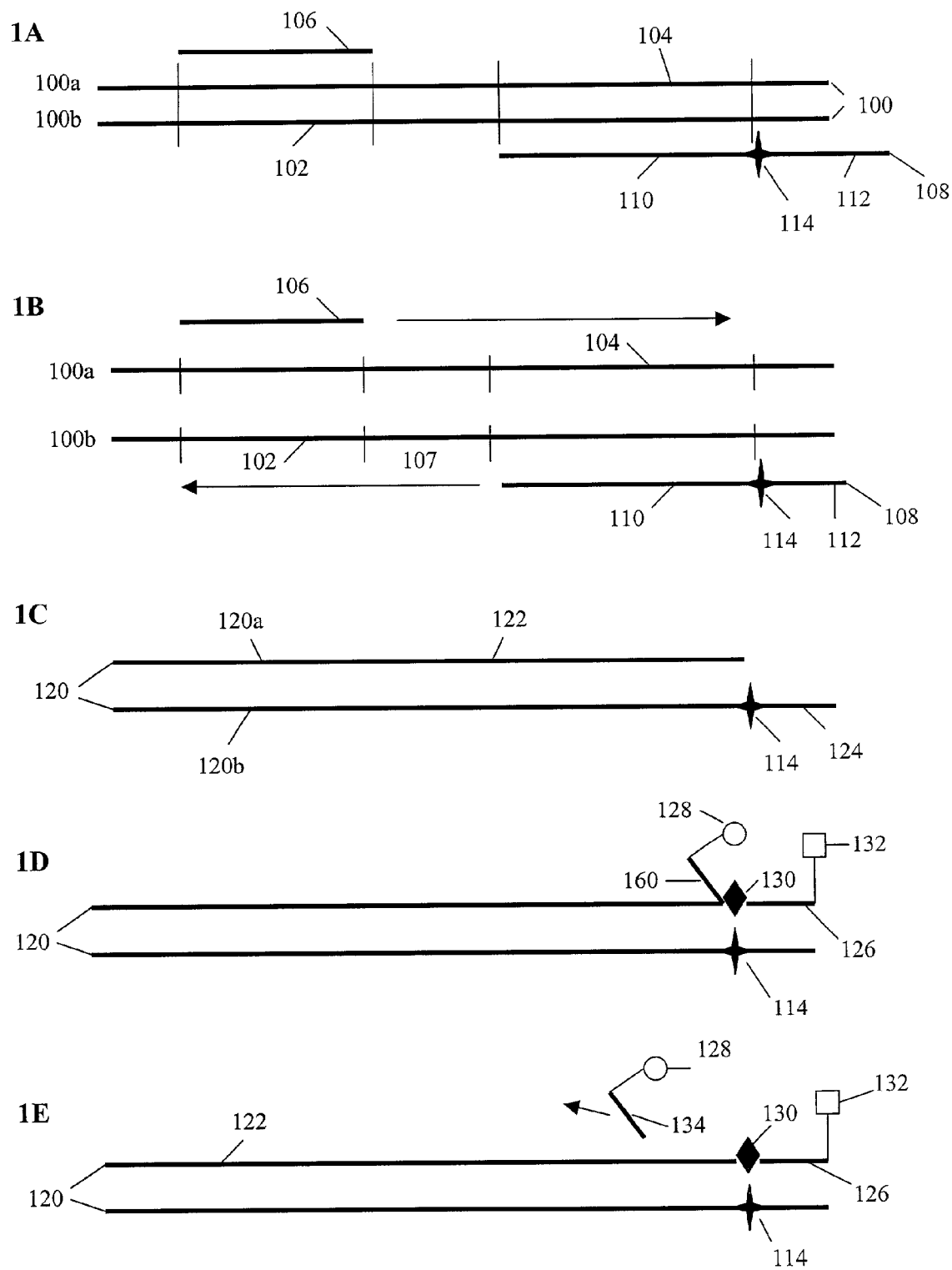
FIGS. 1A-1E schematically illustrate an assay method according to one embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DISCLOSURE OF THE INVENTION

The subject invention concerns methods and materials for detecting, analyzing mutations in, or quantifying the amount of a target nucleic acid in a sample. Methods of the invention generally include the use of PCR. The PCR can be a Fastshot™ amplification. The methods of the present invention employ a reporter oligonucleotide; a nucleic acid polymerase; and first and second oligonucleotide primers, where at least one of the first and second primer oligonucleotides contains at least one non-natural base. Other related assay methods for use with solid supports are described in WO 02/33126, entitled "Solid Support Assay Systems and Methods Utilizing Non-natural Bases".

As used herein, "nucleic acids" include polymeric molecules such as deoxyribonucleic acid (DNA), ribonucleic acid (RNA), peptide nucleic acid (PNA), or any sequence of what are commonly referred to as bases joined by a chemical backbone where the bases have the ability to form base pairs or hybridize with a complementary chemical structure. Suitable non-nucleotidic backbones include, for example, polyamide and polymorpholino backbones. The term "nucleic acids" includes oligonucleotide, nucleotide, or polynucleotide sequences, and fragments or portions thereof. The nucleic acid can be provided in any suitable form, e.g., isolated from natural sources, recombinantly produced, or artificially synthesized, can be single- or double-stranded, and can represent the sense or antisense strand.

The term "oligonucleotide" refers generally to short chain (e.g., less than about 100 nucleotides in length, and typically about 6 to about 50 nucleotides in length) nucleic acids that can be prepared using techniques presently available in the art such as, for example, solid support nucleic acid synthesis, DNA replication, reverse transcription, restriction digest, run-off transcription, or the like. The exact size of the oligonucleotide will depend upon many factors, which in turn will depend upon the ultimate function or use of the oligonucleotide.

A "sequence" refers to an ordered arrangement of nucleotides.

The term "sample" is used in its broadest sense. The term includes a specimen or culture (e.g., microbiological cultures), as well as biological and non-biological samples.

As used herein, "target" or "target nucleic acid" refers to a nucleic acid containing a nucleic acid sequence, suspected to be in a sample and to be detected or quantified in the method or system of the invention. Target nucleic acids contain the target nucleic acid sequences that are actually assayed during an assay procedure. The target can be directly or indirectly assayed. In at least some embodiments, the target nucleic acid, if present in the sample, is used as a template for amplification according to the methods of the invention.

As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. For non-natural bases, as described herein, the base-pairing rules include the formation of hydrogen bonds in a manner similar to the Watson-Crick base pairing rules or by hydrophobic, entropic, or van der Waals forces. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

The term "hybridization" is used in reference to the pairing of complementary nucleic acids. Hybridization and the strength of hybridization (i.e., the strength of the association between the nucleic acids) is influenced by such factors as the degree of complementarity between the nucleic acids, stringency of the hybridization conditions involved, the melting temperature ($T_m$) of the formed hybrid, and the G:C ratio within the nucleic acids.

As used herein, "label" refers to any atom or molecule which can provide a detectable (preferably quantifiable) signal, and which can be attached to a nucleic acid or protein. Labels can provide signals detectable by such techniques as colorimetric, fluorescent, electrophoretic, electrochemical, spectroscopic, chromatogaphic, densitometric, or radiographic techniques, and the like. Labels can be molecules that do not themselves produce a detectable signal, but when used in conjunction with another label can produce or quench a detectable signal. For example, a label can be a quencher of a quencher-dye pair.

As used herein, the term "thermostable nucleic acid polymerase" refers to an enzyme that catalyzes the polymerization of nucleosides and which is relatively stable to heat when compared, for example, to nucleotide polymerases from *E. coli*. Generally, the enzyme will initiate synthesis at the 3'-end of the primer annealed to the target sequence, and will proceed in the 5'-direction along the template, and if possessing a 5' to 3' nuclease activity, hydrolyzing an intervening, annealed oligonucleotide to release intervening nucleotide bases or oligonucleotide fragments, until synthesis terminates. A thermostable enzyme has activity at a temperature of at least about 37° C. to about 42° C., typically in the range from about 50° C. to about 75° C. Representative thermostable polymerases include, for example, thermostable polymerases such as native and altered polymerases of Thermus species, including, but not limited to, *Thermus aquaticus* (Taq), *Thermus flavus* (Tfl), and *Thermus thermophilus* (Tth), and of the *Thermotoga* species, including, but not limited to, *Thermotoga neapolitana*.

As used herein, the term "DNA polymorphism" refers to the condition in which two or more different nucleotide sequences can exist at a particular site in DNA and includes any nucleotide variation, such as single or multiple nucleotide substitutions, deletions or insertions. These nucleotide variations can be mutant or polymorphic allele variations. At least some of the embodiments of the methods described herein can detect single nucleotide changes in nucleic acids such as occur in β-globin genetic diseases caused by single-base mutations, additions or deletions (some β-thalassemias, sickle cell anemia, hemoglobin C disease, etc.), as well as multiple-base variations such as are involved with α-thalassemia or some β-thalassemias. In addition, the process herein can detect polymorphisms, which are not necessarily associated with a disease, but are merely a condition in which two or more different nucleotide sequences (whether having substituted, deleted or inserted nucleotide base pairs) can exist at a particular site in the nucleic acid in the population, as with HLA regions of the human genome and random polymorphisms such as mitochondrial DNA.

The present invention provides methods and materials for detecting a target nucleic acid in a sample. In one embodiment, a method includes contacting a sample suspected of containing the target nucleic acid with a polymerase and first and second primers; amplifying the target nucleic acid, if present in the sample, by PCR using the first and second primers to generate an amplification product having a double-stranded region and a single-stranded region that comprises at least one non-natural base; contacting the sample with a reporter comprising a label and a non-natural base (or bases) that is complementary to the non-natural base (or bases) of the single-stranded region; annealing at least a portion of the reporter to the single-stranded region of the amplification product; cleaving, after annealing, at least a portion of the reporter to release at least one reporter fragment; and correlating the release of the at least one reporter fragment with the presence of the target nucleic acid in the sample.

In another embodiment, a method includes contacting a sample suspected of containing the target nucleic acid with a polymerase and first and second primers; amplifying the target nucleic acid, if present in the sample, by PCR using the first and second primers to generate an amplification product having a double-stranded region and a single-stranded region that comprises at least one non-natural base; contacting the sample with a reporter comprising a label and a non-natural base (or bases) that is complementary to the non-natural base (or bases) of the single-stranded region; incorporating the reporter into the amplification product; and correlating the incorporating of the reporter with the presence of the target nucleic acid in the sample.

The invention also includes corresponding kits for use in detecting target nucleic acids in a sample using one or more of the methods described herein.

The invention can provide a number of advantages, if desired, including, in some embodiments, the ability to detect target nucleic acid in a sample without the need for post-reaction processing such as washing or separation (e.g. by gel electrophoresis). In addition, in some embodiments, the method can be performed by adding all of the elements into one reaction mixture that is processed using one set of reaction conditions. This can, in turn, avoid or reduce problems or concerns associated with multiple reaction steps and reagents.

General Discussion

One embodiment of the invention will now be described in general terms with reference to the schematic representation shown in FIG. 1. Referring to FIG. 1A, a sample is suspected to contain target nucleic acid 100, the target nucleic acid 100 including a first portion 102 and a second portion 104. As shown, target nucleic acid 100 is a double-stranded molecule comprised of strands 100a and 100b.

Referring to FIG. 1B, the sample is contacted with a first primer 106 and a second primer 108 as illustrated. The first primer 106 is complementary to the first portion 102 of the target nucleic acid 100. The second primer 108 includes a first region 110 and a second region 112, the first region 110 comprising a sequence that is complementary to the second portion 104 of the target nucleic acid 100. The second region 112 of the second primer 108 includes a non-natural base 114. The second region 112 is not complementary to the target nucleic acid 100.

In addition to the first primer and the second primer, the sample is also contacted with a polymerase and subjected to polymerase chain reaction (PCR), as herein described. If the target nucleic acid 100 is present in the sample, the complementary region of the first primer 106 and the complementary region of the second primer 108 anneal to the corresponding portions 102 and 104 of the target nucleic acid 100 following standard base-pairing rules. As shown, when the primers are annealed to the target, the 3' terminal nucleotide of the first primer 106 is separated from the 3' terminal nucleotide of the second primer 108 by a sequence of nucleotides, or a "gap," depicted as 107 in FIG. 1B. In a preferred embodiment, the first and second oligonucleotide primers are designed such that a gap 107 of between about zero (0) to about five (5) bases on the template nucleic acid exists between the 3' ends of the PCR primers when annealed to the template nucleic acid.

As shown in FIG. 1B, the polymerase is used to synthesize a single strand from the 3'-OH end of each primer, using PCR, or Fast-shot™ amplification. That is, first primer 106 is used to synthesize strand 120a that is complementary to at least a portion of strand 100a of the target nucleic acid 100, and the second primer 108 is used to synthesize strand 120b that is complementary to at least a portion of strand 100b of the target nucleic acid 100, as illustrated in FIG. 1C. The polymerase chain reaction is allowed to proceed for the desired number of cycles to obtain an amplification product 120.

As shown in FIG. 1C, the amplification product 120 includes a double-stranded region 122 and a single-stranded region 124. As shown in this embodiment, the non-natural base 114 is located in the single-stranded region 124, adjacent the double-stranded region 122. The single-stranded region 124 can include more than one non-natural base.

Referring now to FIG. 1D, the amplification product 120 is contacted with a reporter 126. It is contemplated that the reporter 126 can be added to the reaction before, during, or after, amplification of the target nucleic acid has occurred. The reporter 126 comprises a label 128, 132 and a non-natural base 130 that is complementary to the non-natural base 114 of the single-stranded region 124 of the amplification product 120. In the embodiment shown in FIG. 1D, the reporter 126 includes a label comprising a dye 128 and a quencher 132, and a non-natural base 130. The reporter 126 is allowed to anneal to the amplification product 120. After annealing, at least a portion of the reporter 126 is cleaved, generating a reporter fragment 134 that includes dye 128, as illustrated in FIG. 1E. The release of the reporter fragment 134 is correlated with the presence of the target nucleic acid in the sample. In the illustrated case, the presence of the unquenched dye of the reporter fragment is detected. In an alternative embodiment, the positions of the dye and quencher are reversed, with the reporter fragment carrying away the quencher upon cleavage.

Figure 8:
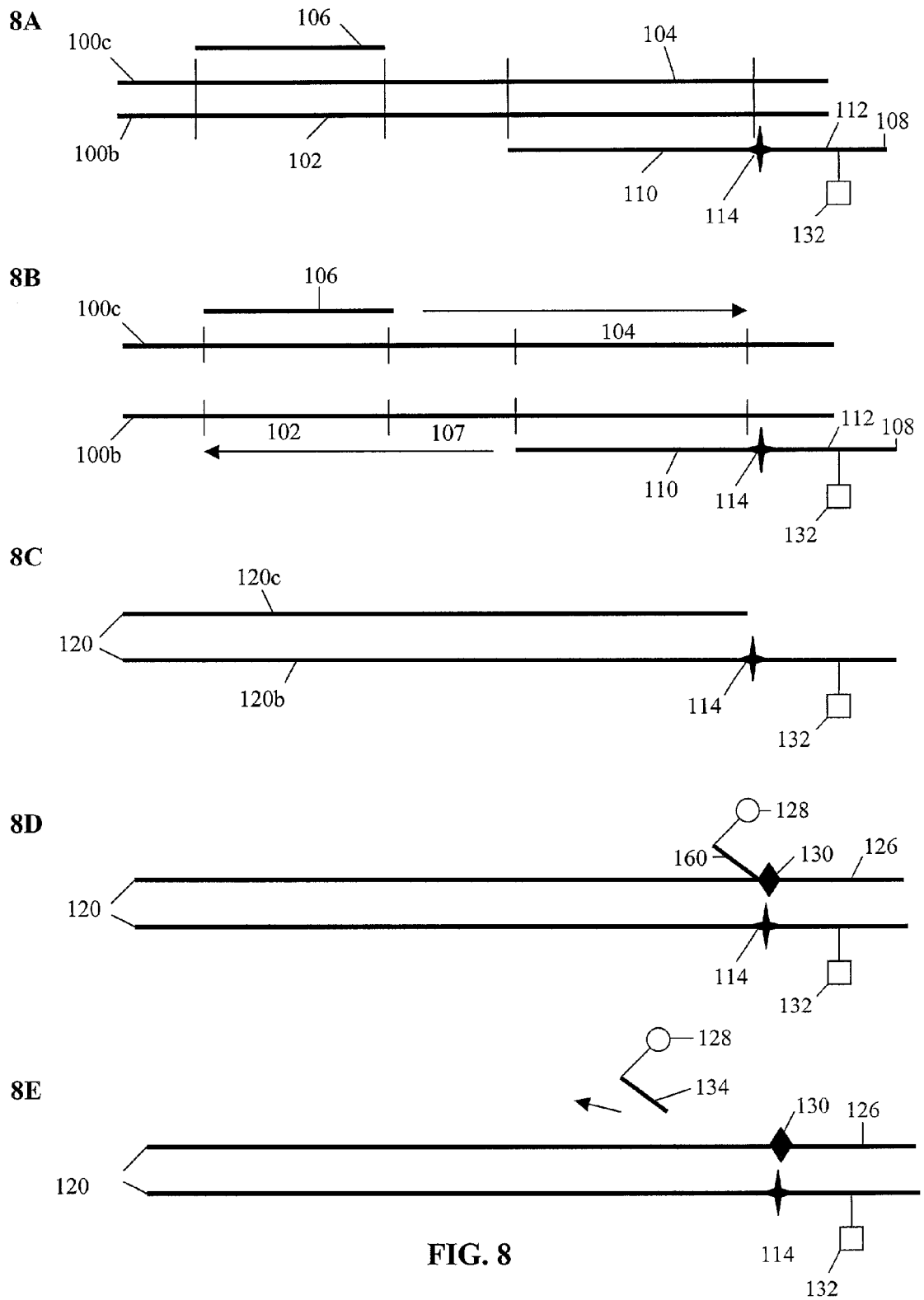
FIGS. 8A-8E schematically illustrate an assay method according to a seventh embodiment of the invention.
Figure 9:
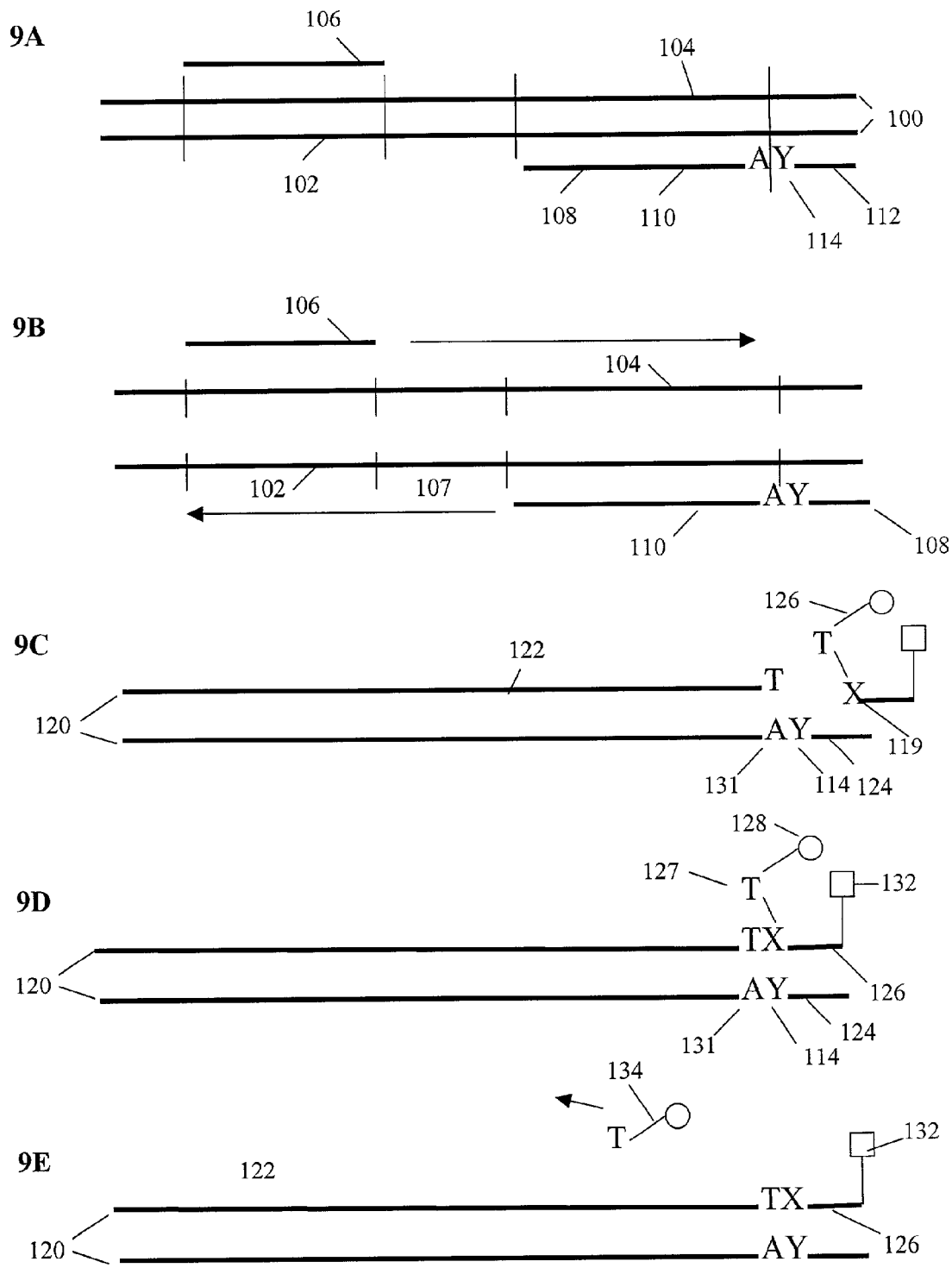
FIGS. 9A-9E schematically illustrate an assay method according to an eighth embodiment of the invention.
Figure 10:
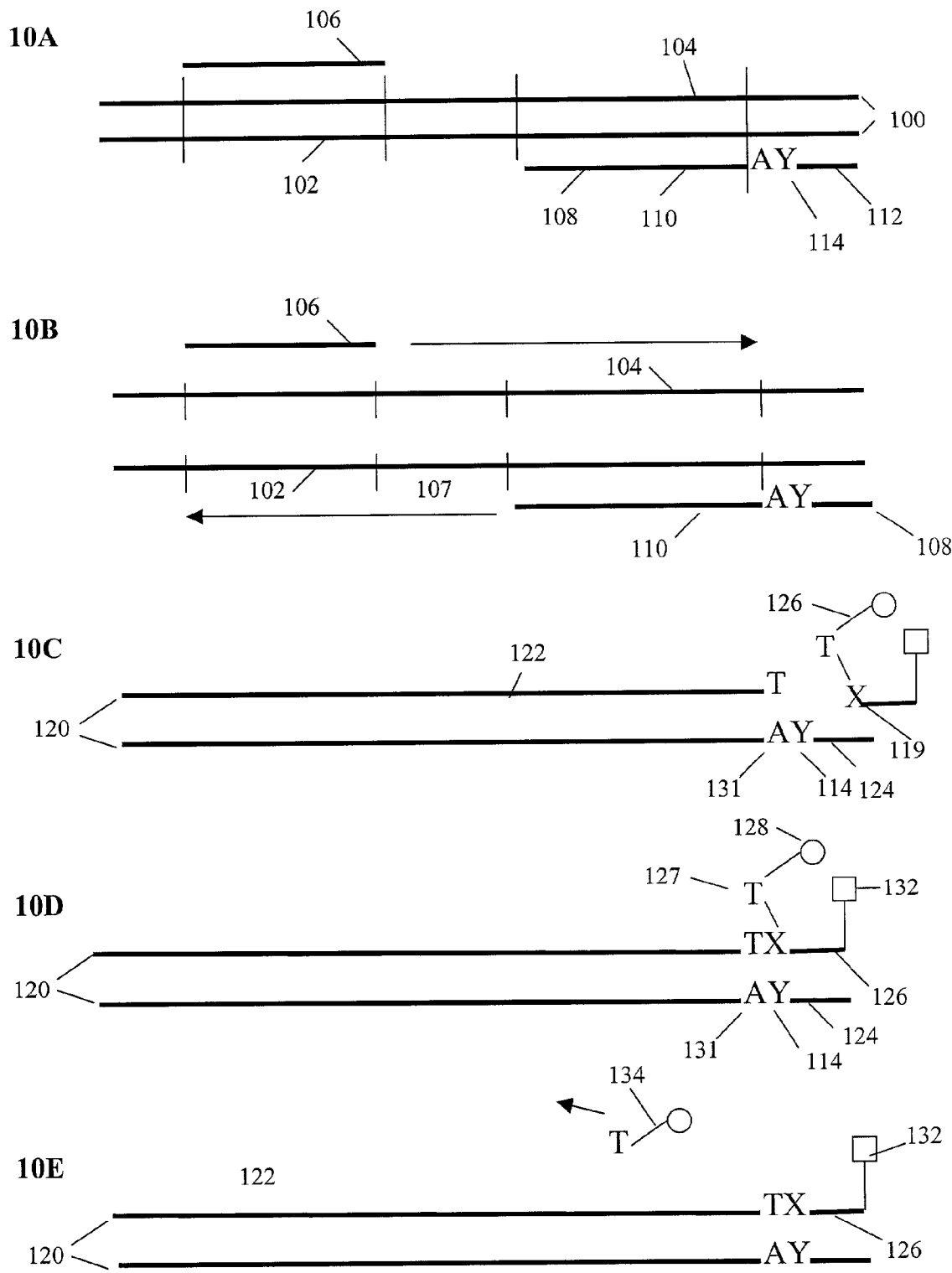
FIGS. 10A-10E schematically illustrate an assay method according to a ninth embodiment of the invention.
Figure 11:
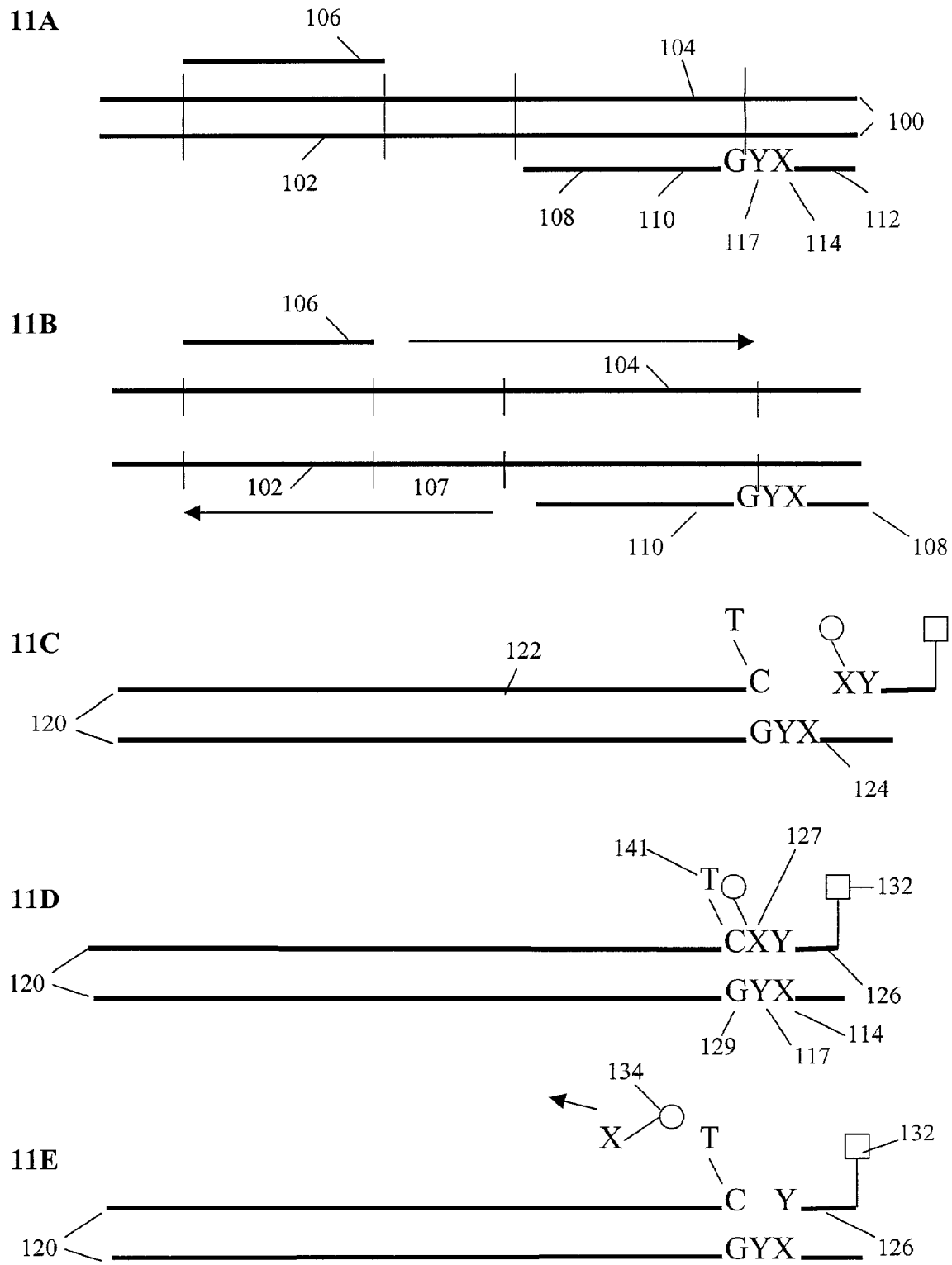
FIGS. 11A-11E schematically illustrate an assay method according to a tenth embodiment of the invention.
Figure 12:
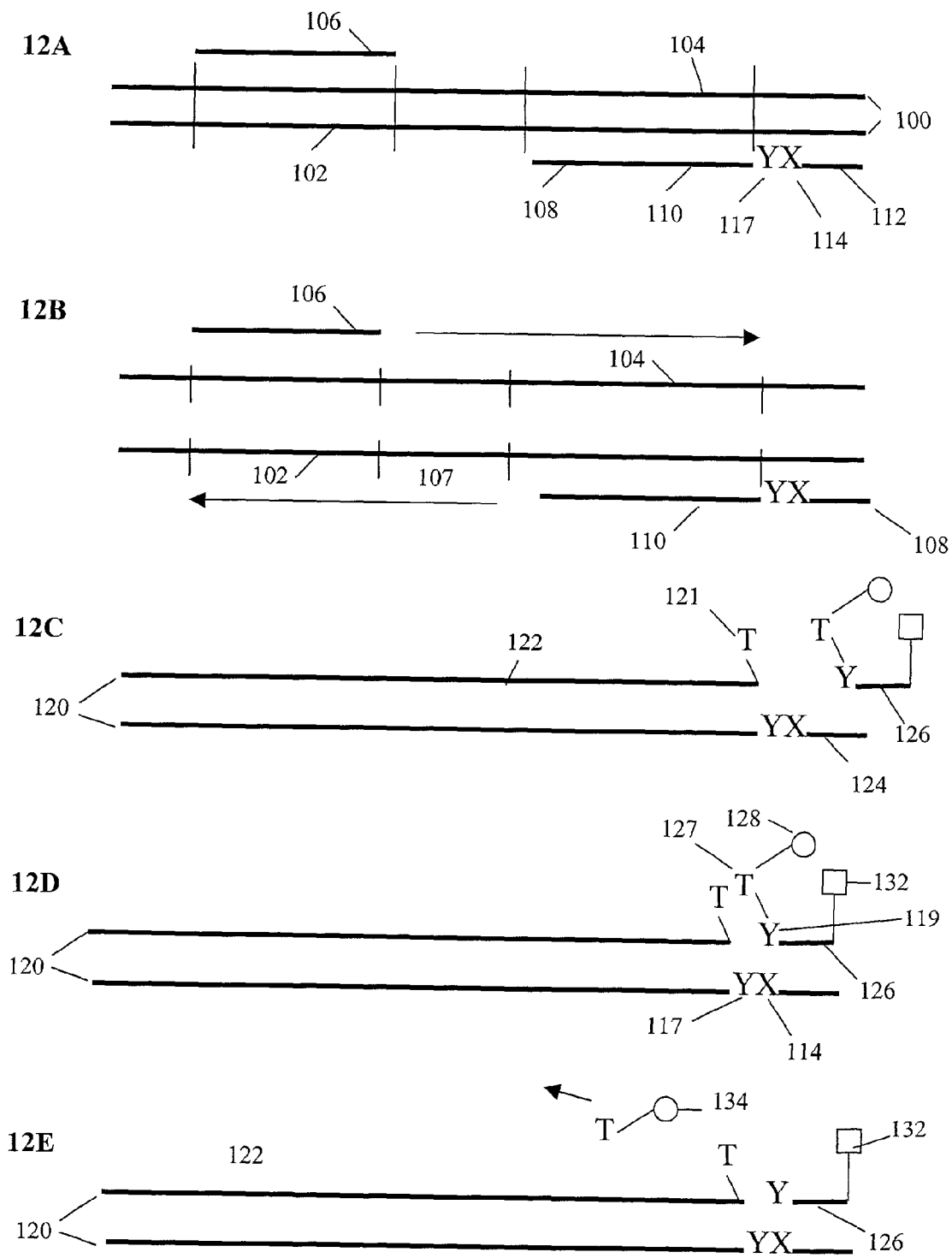
FIGS. 12A-12E schematically illustrate an assay method according to an eleventh embodiment of the invention.
Figure 13:
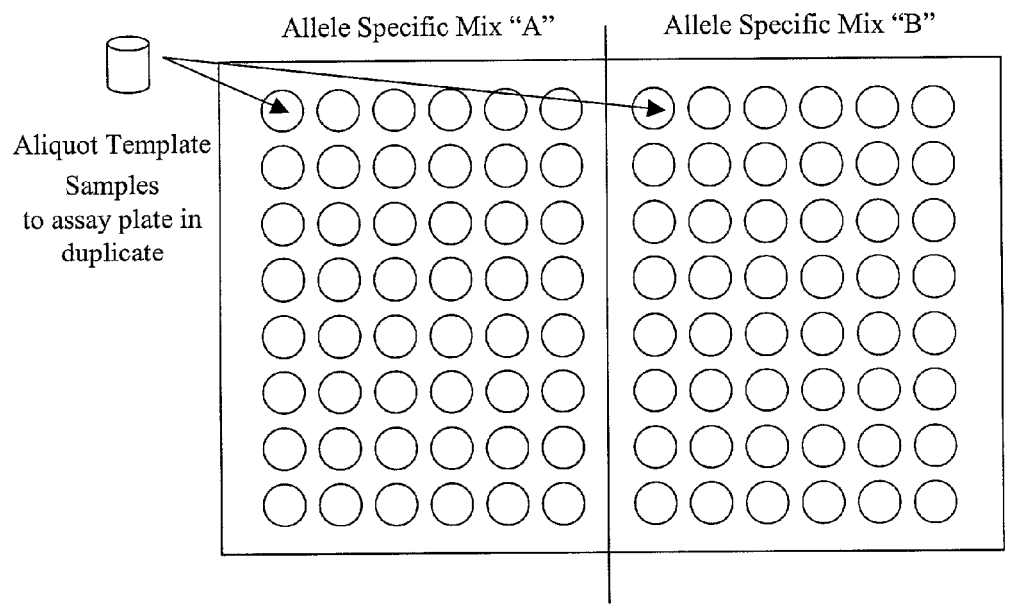
FIG. 13 schematically illustrates a general procedure for preparing an assay plate that contains allele specific PCR mixtures and template samples.

FIG. 8 illustrates an alternative assay in which the quencher 132 is coupled to the second primer 108 instead of the reporter. The quencher 132 quenches the fluorescence of the dye 128 of the reporter 126 until a portion of the reporter 126 is cleaved to generate a reporter fragment 134 that includes the dye 128. As an alternative, the quencher can be coupled to the reporter and the dye can be coupled to the second primer. In the present description, elements in common between the embodiments of the figures are numbered identically, and such elements need not be separately discussed.

FIGS. 9A-9E, 10A-10E, 11A-11E, and 12A-12E illustrate a number of embodiments similar to the assay of FIGS. 1A-1E where X and Y represent non-standard bases. For example, X can represent iso-cytidine (iso-C) and Y can represent iso-guanosine (iso-G). The following descriptions illustrate the differences between the assay of FIGS. 1A-1E and these embodiments. Otherwise, the same considerations and conditions are applicable.

In the assay of FIGS. 9A-9E, the first and second primers 106, 108 are brought into contact with the double stranded target nucleic acid 100, as illustrated in FIG. 9A. The second primer has a first region 110 that is complementary to a portion of the target nucleic acid and a second region 112 that is not complementary to the target nucleic acid and does not typically hybridize to the target nucleic acid. The second primer 108 has a non-standard base 114 in the second region 112 and adjacent to the first region 110 of the second primer that anneals to the target nucleic acid. The first and second primers are used to synthesize by PCR an amplification product 120 that is complementary to portions of the target nucleic acid, as illustrated in FIGS. 9B and 9C. The amplification product 120 has a double stranded region 122 and a single stranded region 124. A reporter 126 is brought into contact with the single stranded region 124 of the amplification product 120, as illustrated in FIG. 9C. The reporter includes a non-standard base 119 that is complementary to the non-standard base 114 of the single stranded region 124. The reporter 126 anneals to the single stranded region 124, as illustrated in FIG. 9D. In the reporter 126, a base 127 adjacent the non-standard base 119 can be complementary, but is not necessarily so, to the base 131 of the double-stranded region adjacent to the non-standard base 114 of the single stranded region. The base 127 is cleaved by the polymerase to form a reporter fragment 134, as illustrated in FIG. 9E, that typically contains a label or a portion 128 of a label, such as a fluorophore or quencher to allow the detection of the reporter fragment of the amplification product 120. Optionally, base 127 is replaced with an oligonucleotide sequence that typically includes the label 128 and is cleaved from the remainder of the reporter.

Another embodiment is illustrated in FIGS. 10A-10E. In this embodiment, base 131 is not part of the first region 110 of the second primer 108 that is complementary to the target nucleic acid sequence, but instead base 131 is non-complementary to the target nucleic acid sequence and is part of the second region 112 of the second primer 108. Otherwise, the steps and procedures of this assay are the same as those of the assay of FIGS. 9A-9E.

In another embodiment, the first and second primers 106, 108 are brought into contact with the double stranded target nucleic acid 100, as illustrated in FIG. 11A. The second primer has a first region 110 that is complementary to a portion of the target nucleic acid and a second region 112 that is not complementary to the target nucleic acid and does not typically hybridize to the target nucleic acid. The second primer 108 has at least two consecutive non-standard bases 114, 117 in the second region 112 and adjacent to the first region 110 of the second primer that anneals to the target nucleic acid. The first and second primers are used to synthesize by PCR an amplification product 120 that is complementary to portions of the target nucleic acid, as illustrated in FIGS. 11B and 11C. The amplification product 120 has a double stranded region 122 and a single stranded region 124. Optionally, a base 141 is misincorporated across from the first of the non-standard bases 114, 117. A reporter 126 is brought into contact with the single stranded region 124 of the amplification product 120, as illustrated in FIG. 11C. The reporter includes non-standard bases that are complementary to the non-standard bases of the second primer. The reporter 126 anneals to the single stranded region 124, as illustrated in FIG. 11D. Non-standard base 127 is cleaved by the polymerase to form a reporter fragment 134, as illustrated in FIG. 11E, that typically contains a label or a portion 128 of a label, such as a fluorophore or quencher to allow detection of the reporter fragment or the amplification product 120. Optionally, base 127 is replaced with an oligonucleotide sequence that typically includes the label 128 and is cleaved from the remainder of the reporter.

In yet another embodiment, the first and second primers 106, 108 are brought into contact with the double stranded target nucleic acid 100, as illustrated in FIG. 12A. The second primer has a first region 110 that is complementary to a portion of the target nucleic acid and a second region 112 that is not complementary to the target nucleic acid and does not typically hybridize to the target nucleic acid. The second primer 108 has two non-standard bases 114, 117 in the second region 112 and adjacent to the first region 110 of the second primer that anneals to the target nucleic acid. The first and second primers are used to synthesize by PCR an amplification product 120 that is complementary to portions of the target nucleic acid, as illustrated in FIGS. 12B and 12C. The amplification product 120 has a double stranded region 122 and a single stranded region 124. Optionally, the amplification product 120 includes a base 121 misincorporated by the polymerase across from non-standard base 117. A reporter 126 is brought into contact with the single stranded region 124 of the amplification product 120, as illustrated in FIG. 12C. The reporter includes a non-standard base that is complementary to the non-standard base 114 of the second primer. The reporter 126 anneals to the single stranded region 124, as illustrated in FIG. 12D. The reporter 126 includes a base 127 coupled to a non-standard base 119 that anneals to base 114 of the single-stranded region, but the base 127 is not complementary to the base 117 of the single-stranded region. Base 127 is cleaved by the polymerase to form a reporter fragment 134, as illustrated in FIG. 12E, that typically contains a label or a portion 128 of a label, such as a fluorophore or quencher, to allow detection of the reporter fragment or the amplification product 120. Optionally, base 127 is replaced with an oligonucleotide sequence that typically includes the label 128 and is cleaved from the remainder of the reporter.

Figure 2:
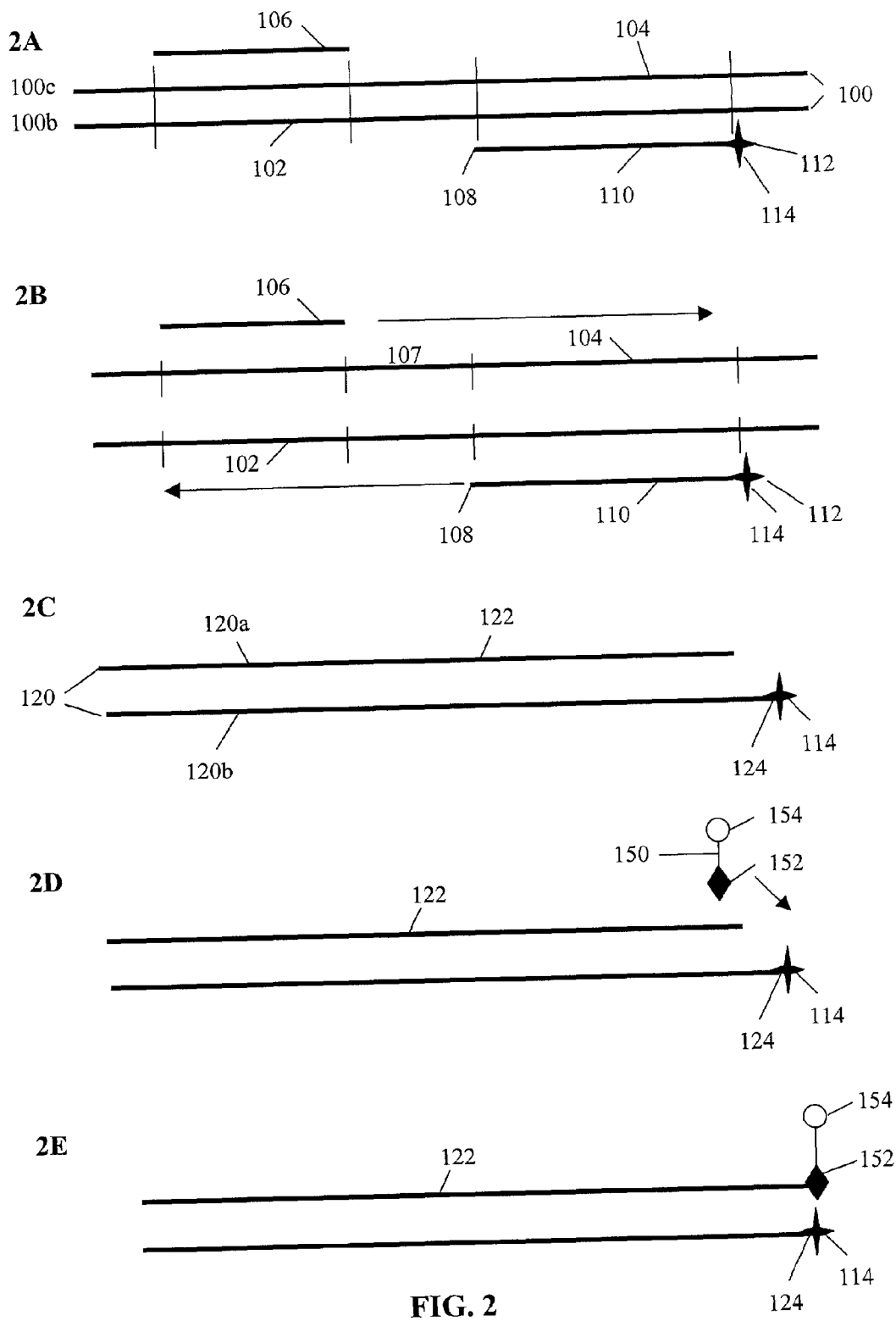
FIGS. 2A-2E schematically illustrate an assay method according to a second embodiment of the invention.

A another embodiment of the invention is shown schematically in FIG. 2. As shown in FIG. 2A, a double-stranded target nucleic acid 100 includes a first portion 102 and a second portion 104. The sample is contacted with a first primer 106 and a second primer 108. The first primer 106 is complementary to the first portion 102 of the target nucleic acid 100. The second primer 108 includes a first region 110 that is complementary to the second portion 104 of the target nucleic acid 100, and a second region 114 that comprises a non-natural base 114 and is not complementary to the target nucleic acid 100.

In addition to the first primer 106 and second primer 108, the sample is contacted with a polymerase (not shown), and a polymerase chain reaction is run. Similar to the embodiment shown in FIG. 1, if the target nucleic acid 100 is present in the sample, the complementary portion of the first primer 106 and the complementary portion 110 of the second primer 108 will anneal to the corresponding regions 102, 104 of the target nucleic acid 100 following standard base-pairing rules. Similar to the embodiment shown in FIG. 1, when the primers are annealed to the target, the 3' terminal nucleotide of the first primer 106 is separated from the 3' terminal nucleotide of the second primer 108 by a sequence of nucleotides, or a "gap" 107. In a preferred embodiment, the first and second oligonucleotide primers are designed such that a gap of between about zero (0) to about five (5) bases on the template nucleic acid exists between the 3' ends of the PCR primers when annealed to the template nucleic acid.

As shown in FIGS. 2B and 2C, the polymerase is used to synthesize a single strand 120a, 120b from the 3'-OH end of each primer, using polymerase chain reaction, or a Fast-shot™ amplification. The polymerase chain reaction is allowed to proceed for the desired number of cycles, to obtain an amplification product 120 shown in FIG. 2C.

As shown in FIG. 2C, the amplification product 120 includes a double-stranded region 122 and a single-stranded region 124. As shown, the single-stranded region 124 comprises the non-natural base 114 of the second primer 108. Although the single-stranded region 124 is shown including a single non-natural base, the invention is not so limited, and the single-stranded region can include more than one non-natural base.

Referring now to FIG. 2D, the amplification product 120 is contacted with a reporter 150. The reporter 150 is added to the sample before, during or after PCR amplification. The reporter 150 comprises a label 154 and a non-natural base 152 that is complementary to the non-natural base 114 of the single-stranded region 124 of the amplification product 120, as illustrated in FIG. 2E. The reporter 150 is incorporated into the amplification product opposite the non-natural base 114. As discussed in more detail below, incorporation of the reporter 150 can be accomplished using any suitable enzyme, such as, for example, a polymerase or ligase. Presence of the target nucleic acid in the sample is determined by correlating the presence of the reporter in the amplification product. In the illustrated case, for example, presence of the target nucleic acid is determined by detecting the label 154, for example, by fluorescence or other visualization method. Suitable detection and visualization methods will be described in more detail below.

While the schematic diagrams of FIGS. 1 and 2 show relative positions and sizes of the components of the invention, these representations are for illustrative purposes only. As will be apparent from the discussion herein, the relative sizes of the first primer and second primer, as well as the first portion and second portion of the target nucleic acid, will vary depending upon the particular application. Further, the relative location of the first primer and the second primer along the target nucleic acid will vary. Additionally, the location of the non-natural base and labels used in the invention will vary depending upon application.

Polymerase

The invention provides methods and materials that utilize the polymerase chain reaction, or a Fast-shot™ amplification, to detect a target nucleic acid of interest in a sample. Suitable nucleic acid polymerases include, for example, polymerases capable of extending an oligonucleotide by incorporating nucleic acids complementary to a template oligonucleotide. For example, the polymerase can be a DNA polymerase.

Enzymes having polymerase activity catalyze the formation of a bond between the 3' hydroxyl group at the growing end of a nucleic acid primer and the 5' phosphate group of a nucleotide triphosphate. These nucleotide triphosphates are usually selected from deoxyadenosine triphosphate (A), deoxythymidine triphosphate (T), deoxycytidine triphosphate (C) and deoxyguanosine triphosphate (G). However, in at least some embodiments, polymerases useful for methods of the present invention can also incorporate non-natural bases using nucleotide triphosphates of those non-natural bases.

Because the relatively high temperatures necessary for strand denaturation during methods such as PCR can result in the irreversible inactivation of many nucleic acid polymerases, nucleic acid polymerase enzymes useful for the invention preferably retain sufficient polymerase activity to complete the reaction when subjected to the temperature extremes of methods such as PCR. Preferably, the nucleic acid polymerase enzymes useful for methods of the invention are thermostable nucleic acid polymerases. Suitable thermostable nucleic acid polymerases include, but are not limited to, enzymes derived from thermophilic organisms. Examples of thermophilic organisms from which suitable thermostable nucleic acid polymerase can be derived include, but are not limited to, *Thermus aquaticus, Thermus thermophilus, Thermus flavus, Thermotoga neapolitana* and species of the *Bacillus, Thermococcus, Sulfobus,* and *Pyrococcus* genera. Nucleic acid polymerases can be purified directly from these thermophilic organisms. However, substantial increases in the yield of nucleic acid polymerase can be obtained by first cloning the gene encoding the enzyme in a multicopy expression vector by recombinant DNA technology methods, inserting the vector into a host cell strain capable of expressing the enzyme, culturing the vector-containing host cells, then extracting the nucleic acid polymerase from a host cell strain which has expressed the enzyme. Suitable thermostable nucleic acid polymerases, such as those described above, are commercially available.

A number of nucleic acid polymerases possess activities in addition to nucleic acid polymerase activity; these can include 5'-3' exonuclease activity and 3'-5' exonuclease activity. The 5'-3' and 3'-5' exonuclease activities are known to those of ordinary skill in the art. The 3'-5' exonuclease activity improves the accuracy of the newly-synthesized strand by removing incorrect bases that have been incorporated. In contrast, the 5'-3' exonuclease activity often present in nucleic acid polymerase enzymes can be undesirable in a particular application since it may digest nucleic acids, including primers, that have an unprotected 5' end. Thus, a thermostable nucleic acid polymerase with an attenuated 5'-3' exonuclease activity, or in which such activity is absent, is a desired characteristic of an enzyme for use in at least some embodiments of the invention. In other embodiments, the polymerase is desired to have 5'-3' exonuclease activity to efficiently cleave the reporter and release labeled fragments so that the signal is directly or indirectly generated.

Suitable nucleic acid polymerases having no 5'-3' exonuclease activity or an attenuated 5'-3' exonuclease activity are known in the art. Various nucleic acid polymerase enzymes have been described where a modification has been introduced in a nucleic acid polymerase which accomplishes this object. For example, the Klenow fragment of *E. coli* DNA polymerase I can be produced as a proteolytic fragment of the holoenzyme in which the domain of the protein controlling the 5'-3' exonuclease activity has been removed. Suitable nucleic acid polymerases deficient in 5'-3' exonuclease activity are commercially available. Examples of commercially available polymerases that are deficient in 5'-3' exonuclease activity include AMPLITAQ STOFFEL™ DNA polymerase and KlenTaq™ DNA polymerase.

Polymerases can "misincorporate" bases during PCR. In other words, the polymerase can incorporate a nucleotide (for example adenine) at the 3' position on the synthesized strand that does not form canonical hydrogen base pairing with the paired nucleotide (for example, cytosine) on the template nucleic acid strand. The PCR conditions can be altered to decrease the occurrence of misincorporation of bases. For example, reaction conditions such as temperature, salt concentration, pH, detergent concentration, type of metal, concentration of metal, and the like can be altered to decrease the likelihood that polymerase will incorporate a base that is not complementary to the template strand.

As an alternative to using a single polymerase, any of the methods described herein can be performed using multiple enzymes. For example, a polymerase, such as an exo-nuclease deficient polymerase, and an exo-nuclease can be used in combination. Another example is the use of an exo-nuclease deficient polymerase and a thermostable flap endonuclease. In addition, it will be recognized that RNA can be used as a sample and that a reverse transcriptase can be used to transcribe the RNA to cDNA. The transcription can occur prior to or during PCR amplification.

First Primer and Second Primer

The invention provides a method of detecting a target nucleic acid using PCR that involves a polymerase, a first primer and a second primer. As shown in FIGS. 1, 2, and 9-12, the first primer 106 comprises a sequence complementary to a first portion 102 of the target nucleic acid 100. The second primer 108 comprises a first region 110 and a second region 112, the first region 110 comprising a sequence complementary to a second portion 104 of the target nucleic acid and the second region 112 comprising at least one non-natural base. The second region is generally not complementary to the target nucleic acid.

In PCR techniques, the primers are designed to be complementary to sequences known to exist in a target nucleic acid to be amplified. Typically, the primers are chosen to be complementary to sequences that flank (and can be part of) the target nucleic acid sequence to be amplified. Preferably, the primers are chosen to be complementary to sequences that flank the target nucleic acid to be detected. Once the sequence of the target nucleic acid is known, the sequence of a primer is prepared by first determining the length or size of the target nucleic acid to be detected, determining appropriate flanking sequences that are near the 5' and 3' ends of the target nucleic acid sequence or close to the 5' and 3' ends, and determining the complementary nucleic acid sequence to the flanking areas of the target nucleic acid sequence using standard Watson-Crick base pairing rules, and then synthesizing the determined primer sequences. This preparation can be accomplished using any suitable methods known in the art, for example, cloning and restriction of appropriate sequences and direct chemical synthesis. Chemical synthesis methods can include, for example, the phosphotriester method described by Narang et al. (1979) Methods in Enzymology 68:90, the phosphodiester method disclosed by Brown et al. (1979) Methods in Enzymology 68:109, the diethylphosphoramidate method disclosed in Beaucage et al. (1981) Tetrahedron Letters 22:1859, and the solid support method disclosed in U.S. Pat. No. 4,458,066, all of which are incorporated herein by reference.

The ability of the first primer and second primer to form sufficiently stable hybrids to the target nucleic acid depends upon several factors, for example, the degree of complementarity exhibited between the primer and the target nucleic acid. Typically, an oligonucleotide having a higher degree of complementarity to its target will form a more stable hybrid with the target.

Additionally, the length of the primer can affect the temperature at which the primer will hybridize to the target nucleic acid. Generally, a longer primer will form a sufficiently stable hybrid to the target nucleic acid sequence at a higher temperature than will a shorter primer.

Further, the presence of high proportion of G or C or of particular non-natural bases in the primer can enhance the stability of a hybrid formed between the primer and the target nucleic acid. This increased stability can be due to, for example, the presence of three hydrogen bonds in a G-C interaction or other non-natural base pair interaction compared to two hydrogen bonds in an A-T interaction.

Stability of a nucleic acid duplex can be estimated or represented by the melting temperature, or "$T_m$." The $T_m$ of a particular nucleic acid duplex under specified conditions is the temperature at which 50% of the population of the nucleic acid duplexes dissociate into single-stranded nucleic acid molecules. The $T_m$ of a particular nucleic acid duplex can be predicted by any suitable method. Suitable methods for determining the $T_m$ of a particular nucleic acid duplex include, for example, software programs. Primers suitable for use in the methods and kits of the present invention can be predetermined based on the predicted $T_m$ of an oligonucleotide duplex that comprises the primer.

As shown in FIGS. 1 and 2, when the first primer and second primer are annealed to the target nucleic acid, a gap 107 exists between the 3' terminal nucleotide of the first primer 106 and the 3' terminal nucleotide of the second primer 108. The gap 107 comprises a number of nucleotides of the target nucleic acid. The gap can be any number of nucleotides provided that the polymerase can effectively incorporate nucleotides into an elongating strand to fill the gap during a round of the PCR reaction (e.g., a round of annealing, extension, denaturation). Typically, a polymerase can place about 30 to about 100 bases per second. Thus, the maximum length of the gap between primers depends upon the amount of time within a round of PCR where the temperature is in a range in which the polymerase is active and the primers are annealed.

For a Fast-shot™ amplification, using a standard thermal cycler, the temperature change is relatively slow given the limitations of the Peltier cooling and heating. When using a standard thermal cycler, the time the Fast-shot™ amplification reaction conditions are within a temperature range where the polymerase is active and the primer is annealed is about 10 to about 15 seconds. It is contemplated that the methods of the invention can be performed using a microfluidics system capable of rapidly thermal cycling the temperature of a sample, where extension times are relatively short and temperature change is relatively rapid. Such rapid thermal cycling can be performed using, for example, LabChip™ technology (Caliper Technology, Palo Alto, Calif.). In one embodiment, the first and second oligonucleotide primers are designed such that a gap of between about zero (0) to about five (5) bases on the target nucleic acid exists between the 3' ends of the PCR primers when annealed to the target nucleic acid.

Non-Natural Bases

As contemplated in the invention, the second region of the second primer typically comprises at least one non-natural base. DNA and RNA are oligonucleotides that include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytidine (C), and uridine (U). These five bases are "natural bases". According to the rules of base pairing elaborated by Watson and Crick, the natural bases can hybridize to form purine-pyrimidine base pairs, where G pairs with C and A pairs with T or U. These pairing rules facilitate specific hybridization of an oligonucleotide with a complementary oligonucleotide.

The formation of these base pairs by the natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural bases, A, G, C, T, and U, can be derivatized by substitution at non-hydrogen bonding sites to form modified natural bases. For example, a natural base can be derivatized for attachment to a support by coupling a reactive functional group (for example, thiol, hydrazine, alcohol, amine, and the like) to a non-hydrogen bonding atom of the base. Other possible substituents include, for example, biotin, digoxigenin, fluorescent groups, alkyl groups (e.g., methyl or ethyl), and the like.

Figure 3:
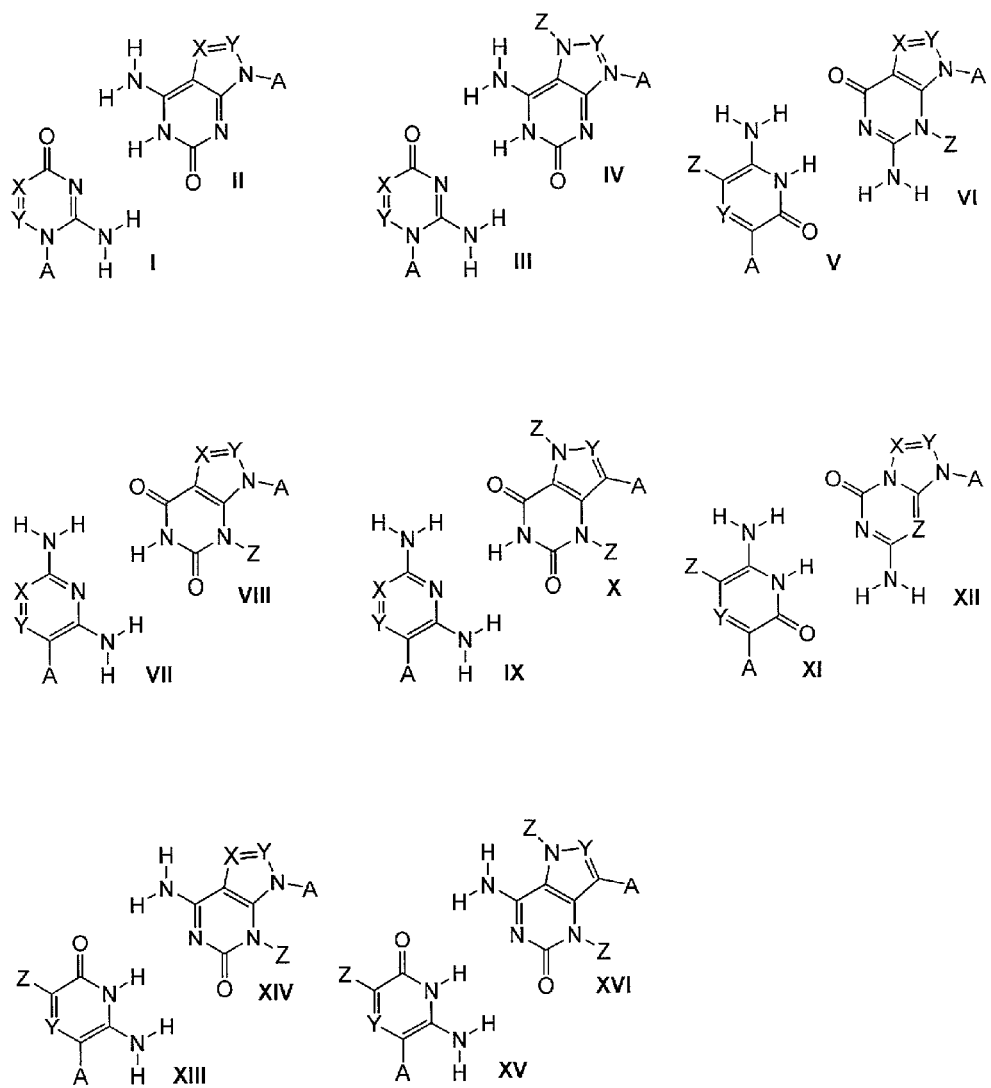
FIG. 3 displays chemical structures for a number of non-natural bases, where A is the point of attachment to a polymeric backbone, X is N or C-Z, Y is N or C—H, and Z is H, a substituted or unsubstituted alkyl group, or a halogen.

Non-natural bases, alternatively referred to herein as non-standard bases, which form hydrogen-bonding base pairs, can also be constructed as described, for example, in U.S. Pat. Nos. 5,432,272, 5,965,364, 6,001,983, and 6,037,120 and U.S. patent application Ser. No. 08/775,401, all of which are incorporated herein by reference. FIG. 3 illustrates several examples of suitable bases and their corresponding base pairs. Specific examples of these bases include the following bases in base pair combinations (iso-C/iso-G, K/X, H/J, and M/N):

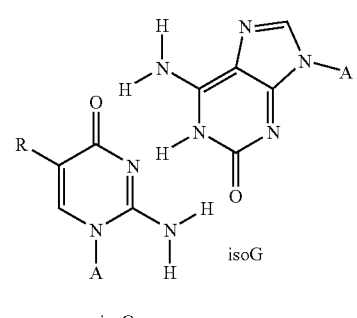

isoC    isoG

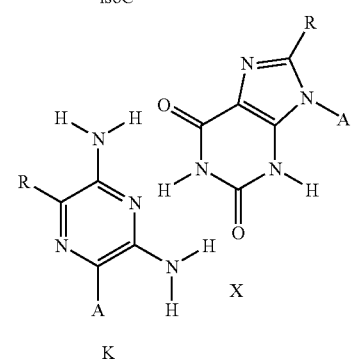

K    X

-continued

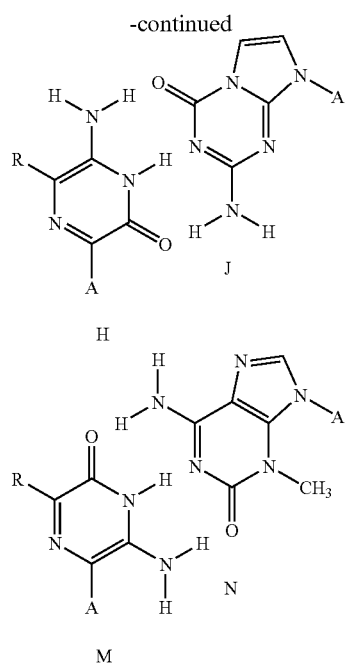

H

M where A is the point of attachment to the sugar or other portion of the polymeric backbone and R is H or a substituted or unsubstituted alkyl group. It will be recognized that other non-natural bases utilizing hydrogen bonding can be prepared, as well as modifications of the above-identified non-natural bases by incorporation of functional groups at the non-hydrogen bonding atoms of the bases.

The hydrogen bonding of these non-natural base pairs is similar to those of the natural bases where two or three hydrogen bonds are formed between hydrogen bond acceptors and hydrogen bond donors of the pairing non-natural bases. One of the differences between the natural bases and these non-natural bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural bases for use in oligonucleotides include, for example, naphthalene, phenanthrene, and pyrene derivatives as discussed, for example, in Ren et al., *J. Am. Chem. Soc.* 118, 1671 (1996) and McMinn et al., *J. Am. Chem. Soc.* 121, 11585 (1999), both of which are incorporated herein by reference. These bases do not utilize hydrogen bonding for stabilization, but instead rely on hydrophobic or van der Waals interactions to form base pairs.

The use of non-natural bases according to the invention is extendable beyond the detection and quantification of nucleic acid sequences present in a sample. For example, non-natural bases can be recognized by many enzymes that catalyze reactions associated with nucleic acids. While a polymerase requires a complementary nucleotide to continue polymerizing an extending oligonucleotide chain, other enzymes do not require a complementary nucleotide. If a non-natural base is present in the template and its complementary non-natural base is not present in the reaction mix, a polymerase will typically stall (or, in some instances, misincorporate a base when given a sufficient amount of time) when attempting to extend an elongating primer past the non-natural base. However, other enzymes that catalyze reactions associated with nucleic acids, such as ligases, kinases, nucleases, polymerases, topoisomerases, helicases, and the like can catalyze reactions involving non-natural bases. Such features of non-natural bases can be taken advantage of, and are within the scope of the present invention.

For example, non-natural bases can be used to generate duplexed nucleic acid sequences having a single strand overhang. This can be accomplished by performing a PCR reaction to detect a target nucleic acid in a sample, the target nucleic acid having a first portion and a second portion, where the reaction system includes all four naturally occurring dNTP's, a first primer that is complementary to the first portion of the target nucleic acid, a second primer having a first region and a second region, the first region being complementary to the first portion of the target nucleic acid, and the second region being noncomplementary to the target nucleic acid. The second region of the second primer comprises a non-natural base. The first primer and the first region of the second primer hybridize to the target nucleic acid, if present. Several rounds of PCR will produce an amplification product containing (i) a double-stranded region and (ii) a single-stranded region. The double-stranded region is formed through extension of the first and second primers during PCR. The single-stranded region includes the one or more non-natural bases. The single-stranded region of the amplification product results because the polymerase is not able to form an extension product by polymerization beyond the non-natural base in the absence of the nucleotide triphosphate of the complementary non-natural base. In this way, the non-natural base functions to maintain a single-stranded region of the amplification product.

As mentioned above, the polymerase can, in some instances, misincorporate a base opposite a non-natural base. In this embodiment, the misincorporation takes place because the reaction mix does not include a complementary non-natural base. Therefore, if given sufficient amount of time, the polymerase can, in some cases, misincorporate a base that is present in the reaction mixture opposite the non-natural base.

Amplifying

During PCR, the polymerase enzyme, first primer and second primer are used to generate an amplification product as described herein. One PCR technique that can be used is a modified PCR, or Fast-shot™ amplification. As used herein, the term "Fast-shot™ amplification" refers to a modified polymerase chain reaction.

Traditional PCR methods include the following steps: denaturation, or melting of double-stranded nucleic acids; annealing of primers; and extension of the primers using a polymerase. This cycle is repeated by denaturing the extended primers and starting again. The number of copies of the target sequence in principle grows exponentially. In practice, it typically doubles with each cycle until reaching a plateau at which more primer-template accumulates than the enzyme can extend during the cycle; then the increase in target nucleic acid becomes linear.

Fast-shot amplification is a modified polymerase chain reaction wherein the extension step, as well as the annealing and melting steps, are very short or eliminated. As used herein, when referring to "steps" of PCR, a step is a period of time during which the reaction is maintained at a desired temperature without substantial fluctuation of that temperature. For example, the extension step for a typical PCR is about 30 seconds to about 60 seconds. The extension step for a Fast-shot™ amplification typically ranges from about 0 seconds to about 20 seconds. Preferably, the extension step is about 1 second or less. In a preferred embodiment, the extension step is eliminated. The time for annealing and melting steps for a typical PCR can range from 30 seconds to 60 seconds. The time for annealing and melting steps for a Fast-shot™ amplification generally can range from about 0 seconds to about 60 seconds. For Fast-shot™ amplification, the annealing and melting steps are typically no more than about 2 seconds, preferably about 1 second or less. When the extension step is eliminated, the temperature is cycled between the annealing and melting steps without including an intermediate extension step between the annealing and melting temperatures.

Additionally, the limit of how quickly the temperature can be changed from the annealing temperature to the melting temperature depends upon the efficiency of the polymerase in incorporating bases onto an extending primer and the number of bases it must incorporate, which is determined by the gap between the primers and the length of the primers. Examples of Fast-shot™ amplification are shown in the Examples.

The number of Fast-shot™ amplification cycles required to determine the presence of a nucleic acid sequence in a sample can vary depending on the number of target molecules in the sample. In one of the examples described below, a total of 37 cycles was adequate to detect as little as 100 target nucleic acid molecules.

Amplification product

As illustrated, for example, in FIGS. 1, 2, and 9-12, PCR is used to generate an amplification product 120 comprising a double-stranded region 122 and a single-stranded region 124. As shown in these figures, the double-stranded region 122 results from extension of the first and second primers 106 and 108. As discussed above, the single-stranded region 124 results from incorporation of a non-natural base in the second primer of the invention. The second region 112 of the second primer 108 is not complementary to the target nucleic acid 100. Because the non-natural base follows base-pairing rules of Watson and Crick and forms bonds with other non-natural bases, as discussed above, the presence of the non-natural base maintains the second region 112 as a single-stranded region 124 in the amplification product 120.

In an alternative embodiment, the single-stranded region 124 comprises more than one non-natural base. The number of non-natural bases included in the second region 112 of the second primer 108 can be selected as desired.

Reporter

As used herein, the term "reporter" refers to a moiety (e.g., an oligonucleotide) that is complementary, and therefore forms a duplex structure with, the second portion of the second primer. Referring to the embodiments shown in, for example, FIGS. 1, 2, and 9-12, the reporter comprises a label 128, 132 (154 in FIG. 2) and at least one non-natural base 130 (152 in FIG. 2) that is complementary to the non-natural base 114 of the single-stranded region 124. The reporter, preferably, is not complementary to either the first primer or the second primer for the polymerase chain reaction. Preferably, the 3' terminus of the reporter is "blocked" to inhibit incorporation of the reporter into a primer extension product. "Blocking" can be achieved by using non-complementary bases or by adding a chemical moiety such as biotin or a phosphate group to the 3' hydroxyl of the last nucleotide, which can, depending upon the selected moiety, serve a dual purpose by also acting as a label.

Reporters useful in the invention can contain more than one non-natural base. The number of non-natural bases included in the reporter can be determined by the user and will depend upon such factors as, for example, the length and base composition of the second region of the second primer and the desired hybridization conditions and hybridization specificity.

The nucleotide content of the reporter is typically determined by the nucleotide content of the second region of the second primer. That is, the sequence of the reporter is determined by determining the sequence of the second region of the second primer, and determining the complement to that second region, using standard rules developed by Watson and Crick. In one embodiment, for example, the second region of the second primer comprises a single non-natural base. In this embodiment, the reporter would preferably include a single non-natural base that is complementary to the non-natural base included in the second primer. Likewise, when more than one non-natural base is included in the second region of the second primer, the sequence of the second region determines the complement to that sequence, and the reporter is synthesized accordingly.

Reporters having the same sequence that is capable of hybridizing to the second portion of a second primer can be used in a variety of assays, provided that the second portion of the second primer is also the same in those assays. In other words, a "universal" reporter and second portion of a second primer can be used. The "universal" second portion of the second primer can then be attached to or synthesized as part of a second primer, where the first portion is specific to the target nucleic acid. This can be used, for example, in kits that are customized by the user for a desired target nucleic acid.

In other embodiments, within a given assay, it is beneficial to use several second primers, each with a different sequence in their second regions, and several reporters, each having a sequence complementary to the second portion of one of the several different second primers. In such assays it can be beneficial for each reporter to have a different label. In some embodiments, the reporters may be attached by their 3' ends to a discrete region of a solid or other unique support.

The ability of reporters to form sufficiently stable hybrids to oligonucleotides having complementary sequences depends on several factors, as discussed above for primers.

Figure 4:
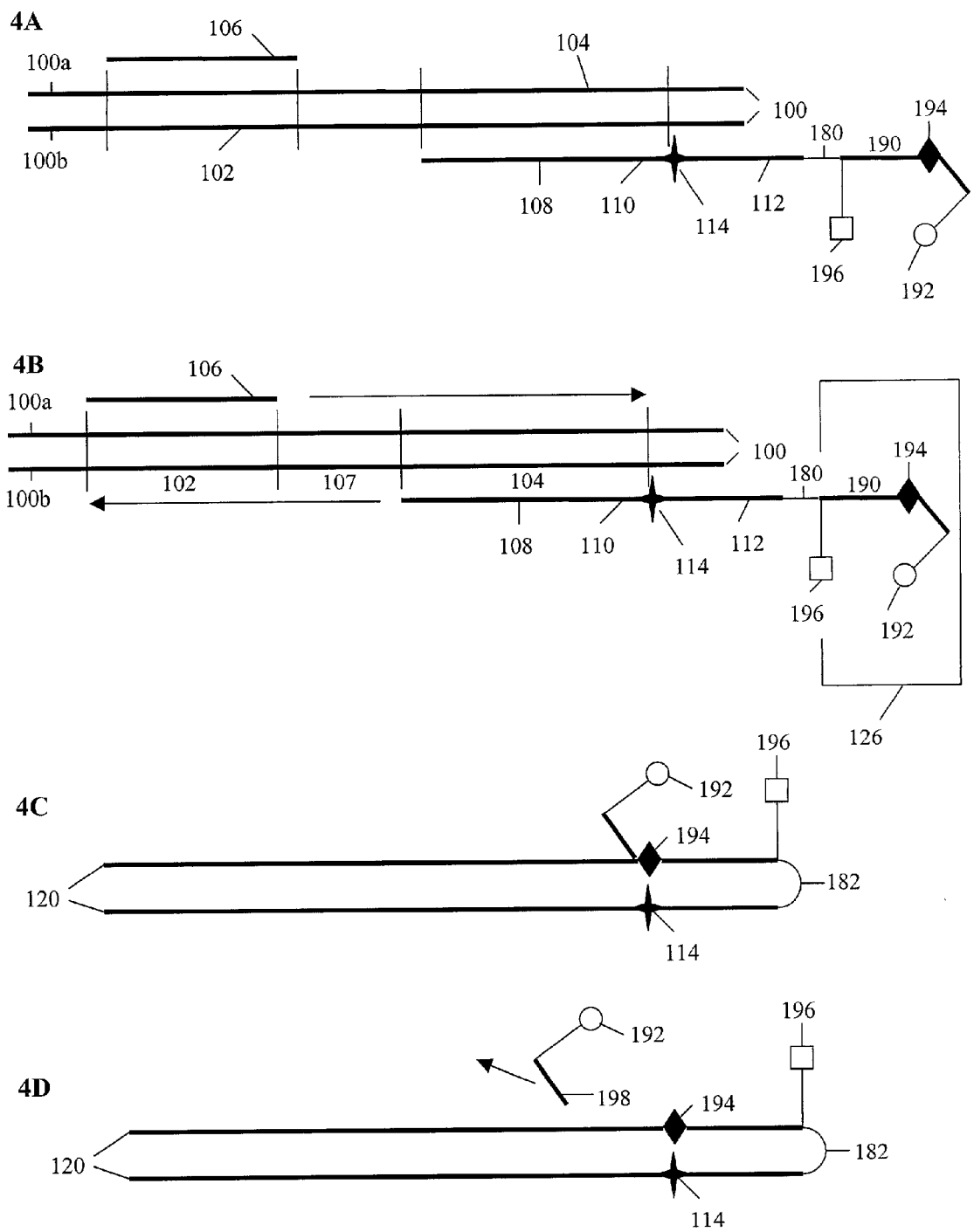
FIGS. 4A-4D schematically illustrate an assay method according to a third embodiment of the invention.

In an alternative embodiment, the second primer and the reporter are a single compound. This embodiment is illustrated in FIG. 4. As shown in FIG. 4A, the target nucleic acid 100 is contacted with a first primer 106 and a second primer 108. In this embodiment, the second primer comprises: a first region 110, a second region 112, a linker 180, a reporter 190, and a quencher 196. In this embodiment, the linker 180 connects the second primer 108 with the reporter 190. The reporter 190 comprises a dye 192, a non-natural base 194, and a quencher 196. The non-natural base 194 is complementary to the non-natural base 114 of the second primer 108. As illustrated in FIG. 4B, the first region 110 anneals to the first portion 102 of the target nucleic acid 100. The linker 180 comprises a chemical linker that couples the 5' end of one nucleotide to the 3' end of another nucleotide. The linker 180 allows the reporter 126 to fold back and form base pairs with the second region 112 of the second primer 102, as illustrated in FIG. 4B. In one embodiment, the linker 180 comprises a sequence of nucleotides of sufficient length to allow the reporter 126 to hybridize with the second region 112. Preferably, the nucleotides that comprise the linker 180 in this embodiment are capable of forming a hairpin loop 182. In another embodiment, the temperature at which the reporter 126 hybridizes to the second region 112 is lower than the temperature at which the first region 110 hybridizes to the second portion 104 of the target 100.

FIG. 4C shows the amplification product 200 that results from extension of primers 104 and 106 during PCR, or Fastshot™ amplification. The amplification product 200 includes a double-stranded region 202 and a single-stranded region 204. The reporter 190 anneals to the single-stranded region 204 of the amplification product.

As shown in FIG. 4D, the reporter 190 is cleaved by an enzyme, for example, the polymerase or other suitable enzyme, thus releasing a reporter fragment 198. The released reporter fragment 198 includes the dye 192. Release of the dye 192 from proximity of the quencher 196 can be visualized as described herein. In some embodiments, the reporter 126 is hybridized to the second region 112 while the first and second primers 106, 108 extend, as illustrated in FIG. 4. This allows the polymerase to cleave the reporter fragment 198 when the first primer 106 has sufficiently extended and can permit the "real time" monitoring of the assay during the PCR process without subsequent addition of a reporter. The hybridization of the reporter to the second region during extension of the first and second primers is not, however, a necessary feature. Hybridization of the reporter to the second region can occur after extension in a manner similar to that described for the assay illustrated in FIG. 1.

Label

In accordance with the invention, the reporter comprises a label. Nucleotides and oligonucleotides can be labeled by incorporating moieties detectable by spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

A variety of labels which are appropriate for use in the invention, as well as methods for their inclusion in the probe, are known in the art and include, but are not limited to, enzyme substrates, radioactive atoms, fluorescent dyes, chromophores, chemiluminescent labels, electrochemiluminescent labels, such as ORI-TAG™ (Igen), ligands having specific binding partners, or any other labels that can interact with each other to enhance, alter, or diminish a signal. It is understood that, should the PCR be practiced using a thermocycler instrument, a label should be selected to survive the temperature cycling required in this automated process.

One radioactive atom suitable for a label according to the methods of the invention is $^{32}P$. Methods for introducing $^{32}P$ into nucleic acids are known in the art, and include, for example, 5' labeling with a kinase, or random insertion by nick translation.

It should be understood that the above description is not meant to categorize the various labels into distinct classes, as the same label can serve in several different modes. For example, $^{125}I$ can serve as a radioactive label or as an electron-dense reagent. Further, one can combine various labels for desired effects. For example, one could label a nucleotide with biotin, and detect its presence with avidin labeled with $^{125}I$. Other permutations and possibilities will be apparent to those of ordinary skill in the art, and are considered within the scope of the instant invention.

In some situations, it is desirable to use two interactive labels on a single oligonucleotide with due consideration given for maintaining an appropriate spacing of the labels on the oligonucleotide to permit the separation of the labels during oligonucleotide hydrolysis. It can be similarly desirable to use two interactive labels on different oligonucleotides, such as, for example, the reporter and the second region of the second primer. In this embodiment, the reporter and the second region are designed to hybridize to each other. Again, consideration is given to maintaining an appropriate spacing of the labels between the oligonucleotides when hybridized.

One type of interactive label pair is a quencher-dye pair. Preferably, the quencher-dye pair is comprised of a fluorophore and a quencher. Suitable fluorophores include, for example, fluorescein, cascade blue, hexachloro-fluorescein, tetrachloro-fluorescein, TAMRA, ROX, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaza-S-indacene-propionic acid, 6-carboxy-X-rhodamine, N,N,N',N'-tetramethyl-6-carboxyrhodamine, Texas Red, Eosin, fluorescein, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid. Suitable quenchers include, for example, Dabcyl, QSY7™ (Molecular Probes, Eugene, Oreg.) and the like. In addition, dyes can also be used as a quencher if they absorb the emitted light of another dye.

The labels can be attached to the nucleotides, including non-natural bases, or oligonucleotides directly or indirectly by a variety of techniques. Depending upon the precise type of label used, the label can be located at the 5' or 3' end of the reporter, located internally in the reporter's nucleotide sequence, or attached to spacer arms extending from the reporter and having various sizes and compositions to facilitate signal interactions. Using commercially available phosphoramidite reagents, one can produce oligonucleotides containing functional groups (e.g., thiols or primary amines) at either terminus, for example by the coupling of a phosphoramidite dye to the 5' hydroxyl of the 5' base by the formation of a phosphate bond, or internally, via an appropriately protected phosphoramidite, and can label them using protocols described in, for example, PCR Protocols: A Guide to Methods and Applications, ed. by Innis et al., Academic Press, Inc., 1990, incorporated herein by reference.

Methods for incorporating oligonucleotide functionalizing reagents having one or more sulfhydryl, amino or hydroxyl moieties into the oligonucleotide reporter sequence, typically at the 5' terminus, are described in U.S. Pat. No. 4,914,210, incorporated herein by reference. For example, 5' phosphate group can be incorporated as a radioisotope by using polynucleotide kinase and $[\gamma^{32}P]ATP$ to provide a reporter group. Biotin can be added to the 5' end by reacting an aminothymidine residue, introduced during synthesis, with an N-hydroxysuccinimide ester of biotin.

Labels at the 3' terminus, for example, can employ polynucleotide terminal transferase to add the desired moiety, such as for example, cordycepin, $^{35}S$-dATP, and biotinylated dUTP.

Oligonucleotide derivatives are also available as labels. For example, etheno-dA and etheno-A are known fluorescent adenine nucleotides which can be incorporated into a reporter. Similarly, etheno-dC is another analog that can be used in reporter synthesis. The reporters containing such nucleotide derivatives can be hydrolyzed to release much more strongly fluorescent mononucleotides by the polymerase's 5' to 3' nuclease activity as nucleic acid polymerase extends a primer during PCR.

In some embodiments, the labeled reporter comprises first and second labels wherein the first label is separated from the second label by a nuclease-susceptible cleavage site.

The label of the reporter can be positioned at any suitable location of the reporter. For example, when the reporter comprises more than one nucleotide, the label can be attached to any suitable nucleotide of the reporter sequence. The label can be positioned at the 5' terminus of the reporter and separated from the reporter sequence that is complementary to the target nucleic acid by a non-complementary sequence. In this embodiment, the reporter comprises a non-natural base that is complementary to the non-natural base of the amplification product, and a sequence that is noncomplementary to the second region of the second primer, and the label is positioned in the sequence that is noncomplementary to the second region. Further, the label can be indirectly attached to a nucleotide of the reporter, using a suitable spacer or chemical linker.

In another embodiment, the labeled reporter comprises a pair of interactive signal-generating labels effectively positioned on the reporter or on the reporter and a second componenet of the assay (such as the second oligonucleotide) so as to quench the generation of detectable signal when the interactive signal-generating labels are in sufficiently close proximity to each other. Preferably, the labels are separated by a site within the reporter that is susceptible to nuclease cleavage, thereby allowing the 5' to 3' nuclease activity of the nucleic acid polymerase to separate the first interactive signal-generating label from the second interactive signal-generating label by cleaving the reporter at the nuclease susceptible site. Separation of the interactive signal-generating moieties (e.g., cleavage of the reporter to release a reporter fragment containing one of the labels) results in the production of a detectable signal. Examples of such labels include dye/quencher pairs or two dye pairs (where the emission of one dye stimulates emission by the second dye).

In an exemplified embodiment, the interactive signal generating pair comprises a fluorophore, for example fluorescein, 5-[(2-aminoethyl)amino]napthalene-1-sulfonic acid (EDANS), tetramethylrhodamine, or the like, and a quencher that can quench the fluorescent emission of the fluorophore, for example, dimethylaminoazobenzen aminoexal-3-acryinido (Dabcyl). The ordinarily skilled artisan can select a suitable quencher moiety that will quench the emission of the particular fluorophore. In the exemplified embodiment, the Dabcyl quencher absorbs the emission of fluorescence from the fluorophore moiety. Fluorophore-quencher pairs have been described in Morrison, Detection of Energy Transfer and Fluorescence Quenching in Nonisotopic Probing, Blotting and Sequencing Academic Press, 1995, incorporated herein by reference.

Figure 6:
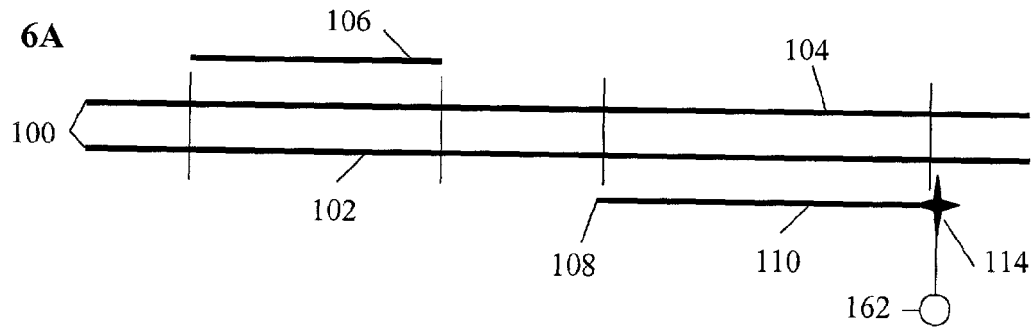
FIGS. 6A-6E schematically illustrate an assay method according to a fifth embodiment of the invention.
Figure 6:
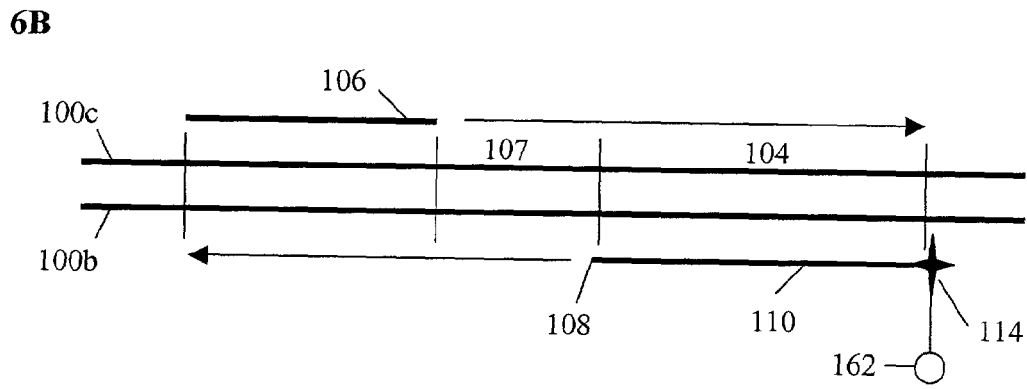
Figure 6:
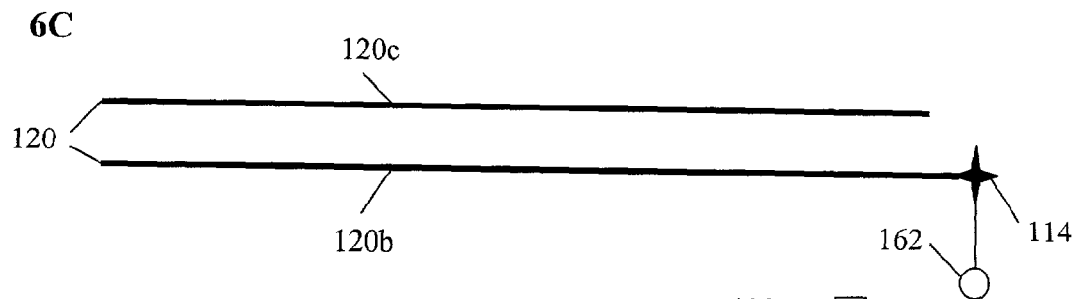
Figure 6:
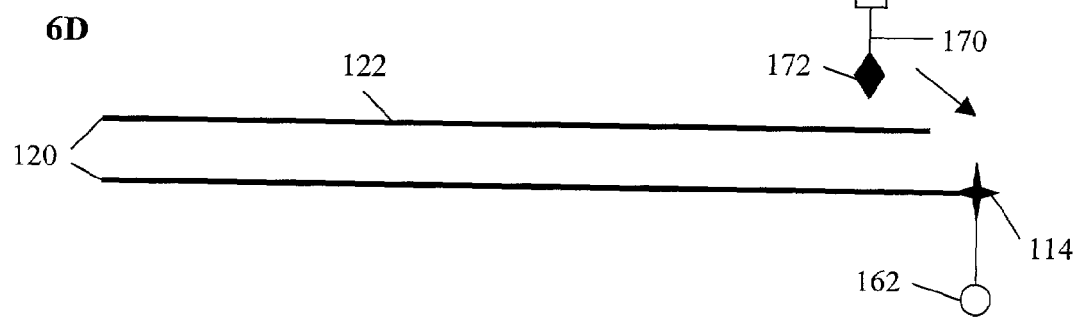
Figure 6:
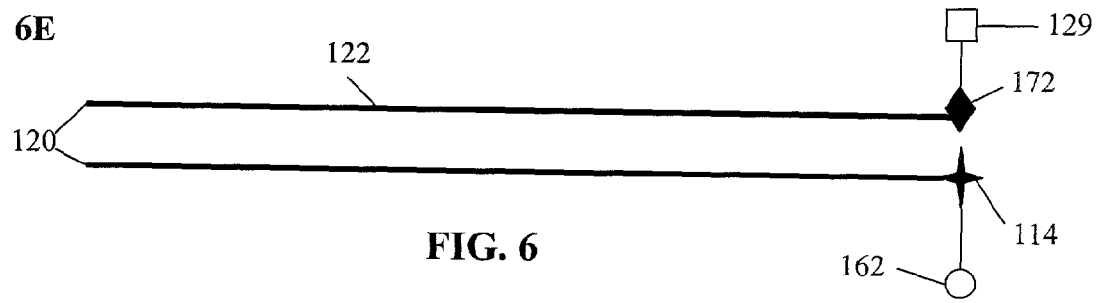

Alternatively, these interactive signal-generating labels can be used in a detection method where the second region of the second primer comprises at least one non-natural base and a label. The second label of the pair is provided by the reporter, which comprises at least one non-natural base that is complementary to the non-natural base of the second primer, and a second label. This embodiment is illustrated in FIG. 6. For example, if a dye/quencher pair is used, hybridization of the reporter to or incorporation of the amplification product will result in a reduction of fluorescence.

Alternatively, the proximity of the two labels can be detected using fluorescence resonance energy transfer (FRET) or fluorescence polarization. FRET is a distance-dependent interaction between the electronic excited states of two dye molecules in which excitation is transferred from a donor molecule to an acceptor molecule without emission of a photon. Examples of donor/acceptor dye pairs for FRET are Fluorescein/Tetramethylrhodamine, IAEDANS™/Fluorescein (Molecular Probes, Eugene, Oreg.), EDANS™/Dabcyl, Fluorescein/Fluorescein (Molecular Probes, Eugene, Oreg.), BODIPY™ FL/BODIPY™ FL (Molecular Probes, Eugene, Oreg.), and Fluorescein/QSY7™.

Annealing

The reporter is added to the sample at an appropriate time during the detection method. In the embodiment illustrated in FIG. 1, after PCR has produced sufficient amplification product 120, the reporter 126 is annealed to the single stranded region 124 of the amplification product 120. In this illustrated embodiment, the reporter 126 comprises a dye 128, a quencher 132, and a non-natural base 130 that is complementary to the non-natural base 114 of the second primer 108. The reporter 126 anneals to the sequence corresponding to the second region 112 of the second primer 108. The reporter 126 can be added to the reaction mix after PCR has produced sufficient amplification product 120, or the reporter 126 can be added to the reaction mix prior to PCR amplification. Preferably, the reporter 126 is added to the reaction mix prior to PCR amplification. After amplification, the temperature is preferably lowered to a temperature lower than the melting temperature of the reporter/amplification product to allow annealing of the reporter to the single-stranded region of the amplification product. In one embodiment, the reaction temperature is lowered to about 49° C. or less during the step of annealing the reporter to the single-stranded overhang region. Annealing is performed similarly for other embodiments of the invention including those using other reporters and other types of labels, as described above. In another embodiment the reporter 126 is annealed at or above the melting temperature of the first and second primers 106, 108 and the amplification product 120. This embodiment is particularly useful when performing "real time" detection of the PCR amplification product Cleaving In one embodiment of the invention, after the reporter anneals to the amplification product, a cleavage event occurs to release at least one reporter fragment. The release of the reporter fragment is correlated with the presence of the target nucleic acid, as described below. Once the reporter anneals to the single-stranded region of the amplification product, this forms a reporter/amplification product complex that is recognizable by an enzyme that cleaves the complex to release the reporter fragment. The enzymes contemplated for use in this embodiment are generally capable of recognizing a variety of reporter/amplification product complex structures. For example, the 5' end portion of the reporter 126 can overlap with a sequence of the amplification product, forming a single-stranded overhang region 160 (see FIG. 1D).

Figure 5:
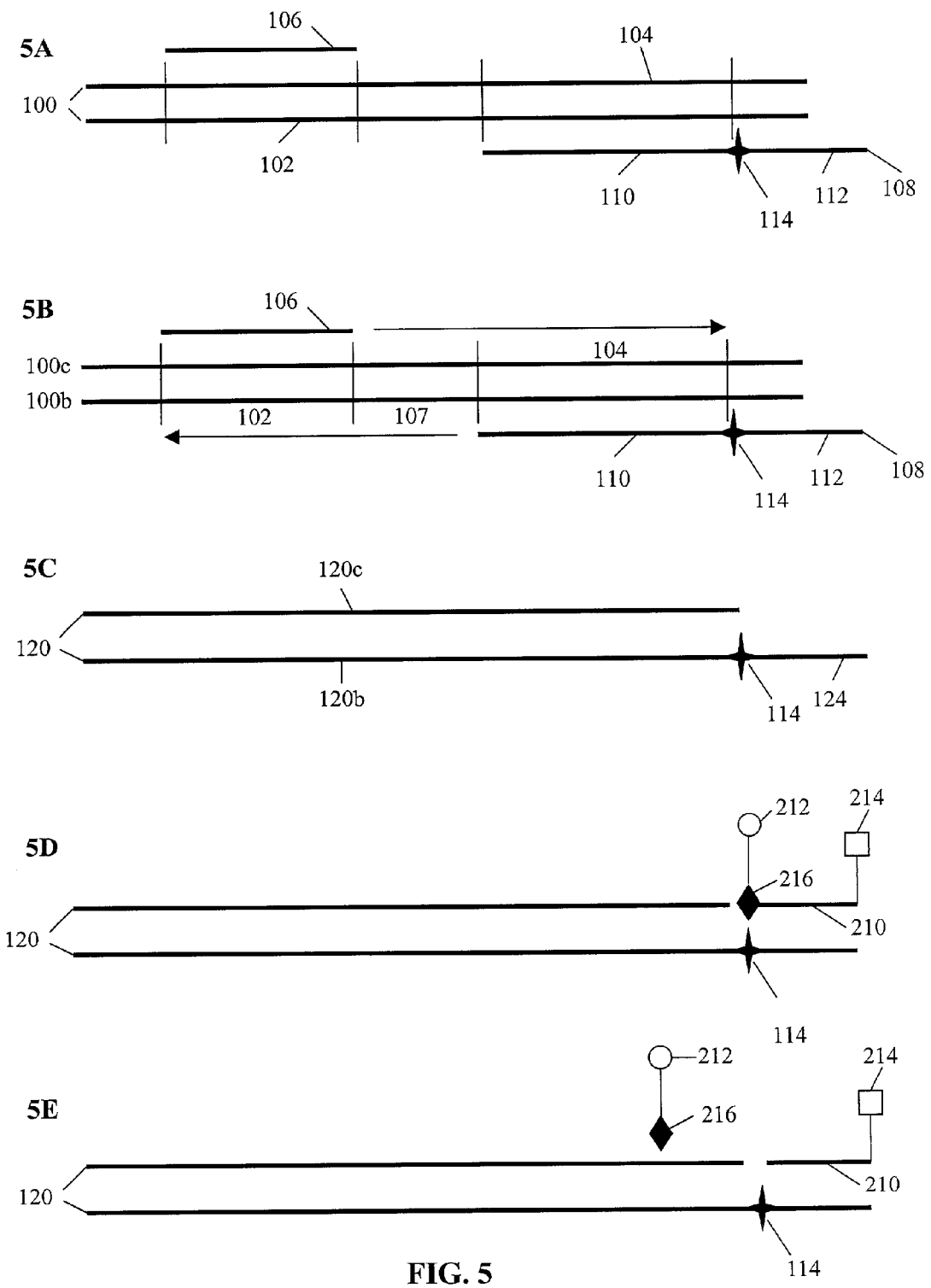
FIGS. 5A-5E schematically illustrate an assay method according to a fourth embodiment of the invention.

In another embodiment, the reporter 126 does not contain an overlapping region to form a single-stranded overhang region, but rather the reporter forms a nick-like structure when it is annealed to the amplification product (see FIG. 5). In this embodiment, a nick-like structure is formed in the amplification product, as shown in FIG. 5D. Generally, a "nick" in duplex DNA is the absence of a phosphodiester bond between two adjacent nucleotides on one strand. As used herein, a "nick-like" structure is formed when there is an absence of the phosphodiester bond between the 5' terminal nucleotide of the reporter 126 and the 3' terminal nucleotide of the strand 120c of the amplification product. There are several enzymes, such as, for example, *E. coli* DNA polymerase I, that are capable of using a nick in duplex DNA as the starting point from which one strand of duplex DNA can be degraded and replaced by resynthesis of new material.

In this embodiment, the reporter 210 includes non-natural base 216 that is complementary to the non-natural base 114 of the amplification product, a dye 212, and a quencher 214. The reporter 210 anneals to a single-stranded portion of the amplification product. Therefore, a nick is produced between the non-natural base 216 and the adjacent nucleotide of the amplification product. In this embodiment, the polymerase recognizes the nick-like structure formed in the reporter/amplification product complex and cleaves the reporter at that nick site. Cleavage of the complex releases the reporter fragment 134, and signal is detected.

While some of the particular structures formed by the reporter/amplification product complex will be discussed in some detail, other reporter/amplification product complexes can be formed to achieve cleavage as described herein.

Referring to the embodiment illustrated in FIG. 1D, after annealing, a portion of the 5' end 160 of the reporter 126 is not annealed to the target and is single-stranded. It is understood that any length, in bases, of the single-stranded overhang region 160 is contemplated, provided that the ability of the 5' to 3' nuclease activity of the polymerase to cleave annealed reporter fragments from the amplification product is maintained. For detection in the embodiment exemplified in FIG. 1D, the reaction is continued under conditions sufficient to allow the 5' to 3' nuclease activity of the polymerase to cleave the annealed reporter 126. Cleavage of the reporter 126 produces cleavage fragments 134 (containing the label or a part of the label) which can then be detected (or, alternatively, the remaining reporter/amplification product complex can be detected) and which are indicative of the presence of the target nucleic acid in the sample. In at least some embodiments, the reporter fragments can include a mixture of mono-, di-, and larger nucleotide fragments.

The nuclease activity of the polymerase cleaves the single-stranded region 160, releasing a reporter fragment 134 as shown in FIG. 1E. In this embodiment, the reporter fragment comprises the dye 128. Release of the dye 128 from the amplification product that includes a quencher 132 allows detection of the dye. Therefore, release of the reporter fragment allows detection of the dye as it is released from proximity to the quencher. This, in turn, allows for correlation of the release of the reporter fragment with presence of the target nucleic acid. If instead, the placement of the dye and quencher are reversed and the quencher is released with the reporter fragment, the dye on the reporter/amplification product is then detected.

Incorporating

Referring now to FIG. 2, an alternative embodiment of the invention is shown. In this embodiment, the second region 124 of the second primer comprises a non-natural base 124. A non-natural base 152 that is complementary to the non-natural base 124 is incorporated into the amplification product using a suitable enzyme. In this embodiment, the incorporation of the reporter is correlated with the presence of the target nucleic acid in the sample.

As shown in FIG. 2, the methods of the present invention employ a reporter 150; a nucleic acid polymerase (not shown); a first primer 106 and a second primer 108. The PCR reaction mixture also contains the four naturally occurring nucleotide triphosphates (i.e., dATP, dCTP, dGTP, and dTTP) as well as one or more non-natural nucleotide triphosphate (or an oligonucleotide containing a non-natural nucleotide triphosphate) as the reporter 150. In the illustrated embodiment, the one or more non-natural nucleotide triphosphates 152 in the reaction mixture comprises a label 154. The PCR can be a Fast-shot™ amplification.

The first primer 106 comprises a sequence complementary to a portion of a target nucleic acid 100 and can hybridize to that portion of the target nucleic acid 100. The second primer 108 has a first region 110 and a second region 112. The first region 110 comprises a sequence complementary to a portion of the target sequence 100. The second region 112 of the second primer 108 comprises a non-natural base 114, and this second region 112 is not complementary to the target nucleic acid 100. Although only a single nucleotide is illustrated in the second region 112, it will be understood that the second region can include additional nucleotides. Preferably, the non-natural base 114 is located at the junction between the first region 110 and the second region 112 of the second primer 108. In some embodiments, the non-natural base 114 present in the second region 112 of the second oligonucleotide primer is an iso-C or an iso-G.

In addition to the first primer 106 and second primer 108, the sample is contacted with a polymerase (not shown), and a polymerase chain reaction is run. If the target nucleic acid 100 is present in the sample, the complementary portion of the first primer 106 and the complementary portion 110 of the second primer 108 anneal to the corresponding regions 102, 104 of the target nucleic acid 100 following standard base-pairing rules. Similar to the embodiment shown in FIG. 1, when the primers are annealed to the target, the 3' terminal nucleotide of the first primer 106 is separated from the 3' terminal nucleotide of the second primer 108 by a sequence of nucleotides, or a "gap." In a preferred embodiment, the first and second primers are designed such that gap of between about zero (0) to about five (5) bases on the template nucleic acid exists between the 3' ends of the PCR primers when annealed to the template nucleic acid.

As shown in FIGS. 2B and 2C, the polymerase is used to synthesize a single strand 120a, 120b from the 3'-OH end of each primer, using polymerase chain reaction, or a modified Fast-shot™ amplification. The polymerase chain reaction is allowed to proceed for the desired number of cycles, to obtain an amplification product 120 shown in FIG. 2C.

As shown in FIG. 2C, the amplification product 120 includes a double-stranded region 122 and a single-stranded region 124. As shown, the single-stranded region 124 comprises the non-natural base 114 of the second primer 108. Although the single-stranded region 124 is shown including a single non-natural base, this region can include more than one non-natural base.

Referring now to FIG. 2D, the amplification product 120 is then contacted with a reporter 150. The reporter 150 comprises a label 154 and a non-natural base 152. The reporter 150 is incorporated into the amplification product opposite the non-natural base 114, as illustrated in FIG. 2E. In one embodiment, the non-natural base 152 of the reporter 150 comprises a nucleotide triphosphate base that is complementary to the non-natural base 114 of the single-stranded region 124 of the amplification product 120. In this embodiment, the PCR reaction includes the presence of labeled non-natural nucleotide triphosphate base, in addition to the four naturally occurring nucleotide triphosphate bases (i.e., dATP, dCTP, dGTP, and dTTP). The concentration of non-natural nucleotide triphosphate base in the PCR reaction can range, for example, from 1 μM to 100 μM.

Suitable enzymes for incorporation of the reporter 150 into the amplification product 120 include, for example, polymerases and ligases. A number of polymerases that are capable of incorporating natural nucleotides into an extending primer chain can also incorporate a non-natural base into an amplification product opposite a complementary non-natural base. Typically, class A DNA polymerases; such as Klenow, Tfl, Tth, Taq, Hot Tub, and Bst, are better able than class B polymerases; such as Pfu, Tli, Vent exo-, T4, and Pwo, to incorporate a non-natural base. Reverse transcriptases, such as HIV-1, can also be used to incorporate non-natural bases into an extending primer opposite its complementary non-natural base within a template. In this embodiment the polymerase can be nuclease deficient or can have reduced nuclease activity. While not intended to limit the invention, nuclease deficient polymerases are expected to be more robust because nuclease activities have been shown to interfere with some PCR reactions (*Gene* 1992 112(1):29-35 and *Science* 1993 260(5109):778-83).

Presence of the target nucleic acid in the sample is determined by correlating the presence of the reporter in the amplification product. Suitable detection and visualization methods are used to detect the target nucleic acid. In the illustrated case, for example, presence of the target nucleic acid is determined by detecting the label 154, for example, by fluorescence or other visualization method. Fluorescence polarization, for example, can be used to detect the incorporation of the reporter into the amplification product.

Preferably, in this embodiment, a washing step or a separation step is performed after incorporation of the reporter 150 into the amplification product 120, and prior to detection. This washing or separation step will remove unbound reporter 150 from the system, so that detection of signal is dependent upon incorporated reporter. One of skill in the art would readily appreciate that any known washing or separation steps can be used in connection with the invention, including size separation by gel electrophoresis, and the like. Alternatively, a washing step is not needed when fluorescence polarization is used as the method of detection.

The reporter 150 used in this embodiment comprises at least one non-natural base 152. The non-natural base(s) of the reporter preferably include a label 154. The non-natural base(s) 152 of the reporter 150 is capable of being inserted by the polymerase into the amplification product opposite to the at least one non-natural base 114 of the second primer 108 during the PCR amplification.

In another embodiment, illustrated in FIG. 6, the reporter 170 comprises a non-natural base 172 that is complementary to non-natural base 114 of the second primer 108, and a quencher 129. In this embodiment, the non-natural base 114 of the second primer 108 includes a dye 162. In this embodiment, incorporation of the reporter 170 brings the quencher 129 into proximity with the dye 162. This, in turn, reduces the signal output of the dye 162, and this reduction in signal can be detected and correlated with the presence of the target nucleic acid. Suitable dye-quencher pairs are discussed above. Alternatively, a dye-dye pair can be used. When the target nucleic acid is present, PCR creates a duplexed product that places the two dyes in close proximity, and the fluorescent output of the label changes. The change is detectable by bench-top fluorescent plate readers.

The polymerase used in this embodiment can have nuclease activity, can have reduced nuclease activity, or can be nuclease deficient. Preferably, the polymerase is a thermostable polymerase.

Detection

Detection and analysis of the reporter oligonucleotide fragments can be accomplished using any methods known in the art. Numerous methods are available for the detection of nucleic acids containing any of the above-listed labels. For example, biotin-labeled oligonucleotide(s) can be detected using non-isotopic detection methods which employ avidin conjugates such as streptavidin-alkaline phosphatase conjugates. Fluorescein-labeled oligonucleotide(s) can be detected using a fluorescein-imager.

In one embodiment the reporter oligonucleotides can be detected within the PCR reaction mixture without any further processing. For example, the signal from cleaved oligonucleotides can be resolved from that of uncleaved oligonucleotides without physical separation. This can be accomplished, for example by fluorescence polarization analysis where a change in size and therefore rate of rotation in solution of fluorescent molecules can be detected.

In one embodiment, when the target is present, a duplexed product is created that places the first and second labels (e.g. dye/dye pair) into close proximity. When the two labels are in close proximity, the fluorescent output of the reporter molecule label changes. The change is detectable by most benchtop fluorescent plate readers. Alternatively, the label pair comprises a quencher-label pair in close proximity. In this embodiment, the fluorescent output of the reporter molecule label changes, and this change is detectable. Other suitable detection methods are contemplated in this invention.

In another embodiment, the reporter is detected after further processing. It is contemplated that the reporter oligonucleotide fragments can be separated from the reaction using any of the many techniques known in the art useful for separating oligonucleotides. For example, the reporter oligonucleotide fragments can be separated from the reaction mixture by solid phase extraction. The reporter oligonucleotide fragments can be separated by electrophoresis or by methods other than electrophoresis. For example, biotin-labeled oligonucleotides can be separated from nucleic acid present in the reaction mixture using paramagnetic or magnetic beads, or particles which are coated with avidin (or streptavidin). In this manner, the biotinylated oligonucleotide/avidin-magnetic bead complex can be physically separated from the other components in the mixture by exposing the complexes to a magnetic field. In one embodiment, reporter oligonucleotide fragments are analyzed by mass spectrometry.

In some embodiments, when amplification is performed and detected on an instrument capable of reading fluorescence during thermal cycling, the intended PCR product from non-specific PCR products can be differentiated. Amplification products other than the intended products can be formed when there is a limited amount of template nucleic acid. This can be due to a primer dimer formation where the second primer 108 is incorporated into a primer dimer with itself or the first primer 106. During primer dimer formation the 3' ends of the two primers hybridize and are extended by the nucleic acid polymerase to the 5' end of each primer involved. This creates a substrate that when formed is a perfect substrate for the primers involved to exponentially create more of this non-specific products in subsequent rounds of amplification. Therefore the initial formation of the primer dimer does not need to be a favorable interaction since even if it is a very rare event the amplification process can allow the dimer product to overwhelm the reaction, particularly when template nucleic acid is limited or absent. When the second oligonucleotide primer 106 is incorporated into this product a labeled nonstandard base 170 is placed orthogonal to the nonstandard base 114 of the second primer 106. This results in an interaction between the labels 129 of the reporter and 162 of the second primer which would give the same fluorescent output change as in the formation of the intended product 120 as shown in FIG. 6E. Primer dimer products are typically shorter in length than the intended product and therefore have a lower melting temperature. Since the labels are held in close proximity across the duplex as shown in 6E an event that would separate the two strands would disrupt the interaction of the labels. Increasing the temperature of the reaction which contains the reaction products to above the Tm of the duplexed DNAs of the primer dimer and intended product would melt the DNA duplex of the product and disrupt the interaction of the labels giving a measurable change in fluorescence. By measuring the change in fluorescence while gradually increasing the temperature of the reaction subsequent to amplification and signal generation it is possible to determine the Tm of the intended product as well as that of the nonspecific product.

Nested PCR

Nested PCR can be performed using the method of the invention. By way of example, nested PCR can be performed using a first, second, and third primers (or more). The second primer has a first region complementary to the target sequence and a second region complementary to the reporter oligonucleotide. The first and third primers can hybridize to the target at higher temperatures than the second primer. A first amplification product can be produced after several PCR cycles are performed where cycling between denaturation and annealing temperatures allows annealing of the first and third primer to the target nucleic acid, but not the second primer. The PCR annealing temperature can subsequently be reduced to allow the first region of the second primer to hybridize to the first amplification product. Several cycles of PCR at the reduced annealing temperature can produce a second amplification product between the first and second primers. The temperature can be lowered to allow hybridization of the reporter oligonucleotide to the second region of the second primer.

Use in Detection of DNA Polymorphisms

The methods of the invention are useful for detecting sequence variations in nucleic acid sequences. As used herein, "sequence variation" refers to differences in nucleic acid sequence between two nucleic acids. For example, a wild-type gene and a mutant form of this gene can vary in sequence by the presence of single base substitutions or deletions or insertions of one or more nucleotides. These two forms of the gene are said to vary in sequence from one another. One example of sequence variation is DNA polymorphisms. In an embodiment illustrated in FIG. 7, detection of a single nucleotide polymorphism (SNP) using PCR and requiring no further sample manipulation other than placing the PCR reaction plate onto a fluorescence plate reader is illustrated. Allele-specific reporters or primers are used which contain an allele-specific label. For example, a two allele system might include allele-specific reporters or primers with labels having different colors. The presence of either color indicating the presence of that allele in the sample and the presence of the combination of the two colors indicating that both alleles are present in the sample.

In this embodiment, the primers are designed to detect the single nucleotide polymorphism as follows. Preferably, one of the primers used comprises an allele specific primer. Preferably, one of the primers comprises a non-natural base. In one embodiment, both of these features are provided by a single primer. Alternatively, the allele specific primer is a separate primer from the primer that comprises a non-natural base.

As used herein, "allele specific primer" means a primer that is completely complementary to a target nucleic acid in a region suspected to contain a SNP.

The allele specific PCR primers that can be used to discriminate the SNP alleles are designed to be complementary to each allele such that the polymorphic base of interest is positioned at the 3' end of the primer. High levels of allelic discrimination are achieved in part by the limited ability of the polymerase to extend a primer which has a nucleotide mismatch at its 3' end with that of the target DNA, i.e., the corresponding allele to which the primer is not specific. Additionally, allelic discrimination can be accomplished by placing the mismatch at other positions in the allele specific primer. Generally, the allele specific position can be anywhere within the primer provided that the polymerase cannot efficiently extend the primer if there is a mismatch. Preferably, the primers are chosen so that the allele mismatch sufficiently destabilizes hybridization of the allele-specific primer to a target nucleic acid sequence of a different allele for the selected PCR conditions. In one embodiment, the allele specific position is within about 5 bases from the 3'-end of the primer. For example, the allele specific position can be at the 3'-terminal base of the primer. These alternate positions for the allele specific position in the primer can be used to achieve selective amplification in two primary ways: 1) by lowering the Tm of the primer so that it is not hybridized on the template DNA during thermal cycling for the polymerase to extend, or 2) by creating an unfavorable primer/template structure that the polymerase will not extend. Enhanced specificity is achieved by using Fast-shot™ amplification cycles where the extension stop time, as well as the stop times for annealing and melting, are brief or non-existent. In one such embodiment, the reactions are rapidly cycled between about 90-100° C. and about 50-65° C. with a maximum of about a one-second hold at each temperature, thereby leaving the polymerase little time to extend mismatched primers. In an exemplified embodiment, the reaction is cycled between about 95° C. and about 58° C. with about a one second hold at each temperature. This rapid cycling is made possible by generating the shortest possible PCR product by, in general, leaving a gap of about zero (0) to about five (5) bases on the template nucleic acid between the 3' bases of the PCR primers. Preferably, the primers are designed to have the shortest sequence possible and a Tm of approximately 55-60° C. In one embodiment involving SNP analysis on genomic DNA samples a total of about 37 cycles was adequate to detect as little as 30 target molecules.

Figure 7:
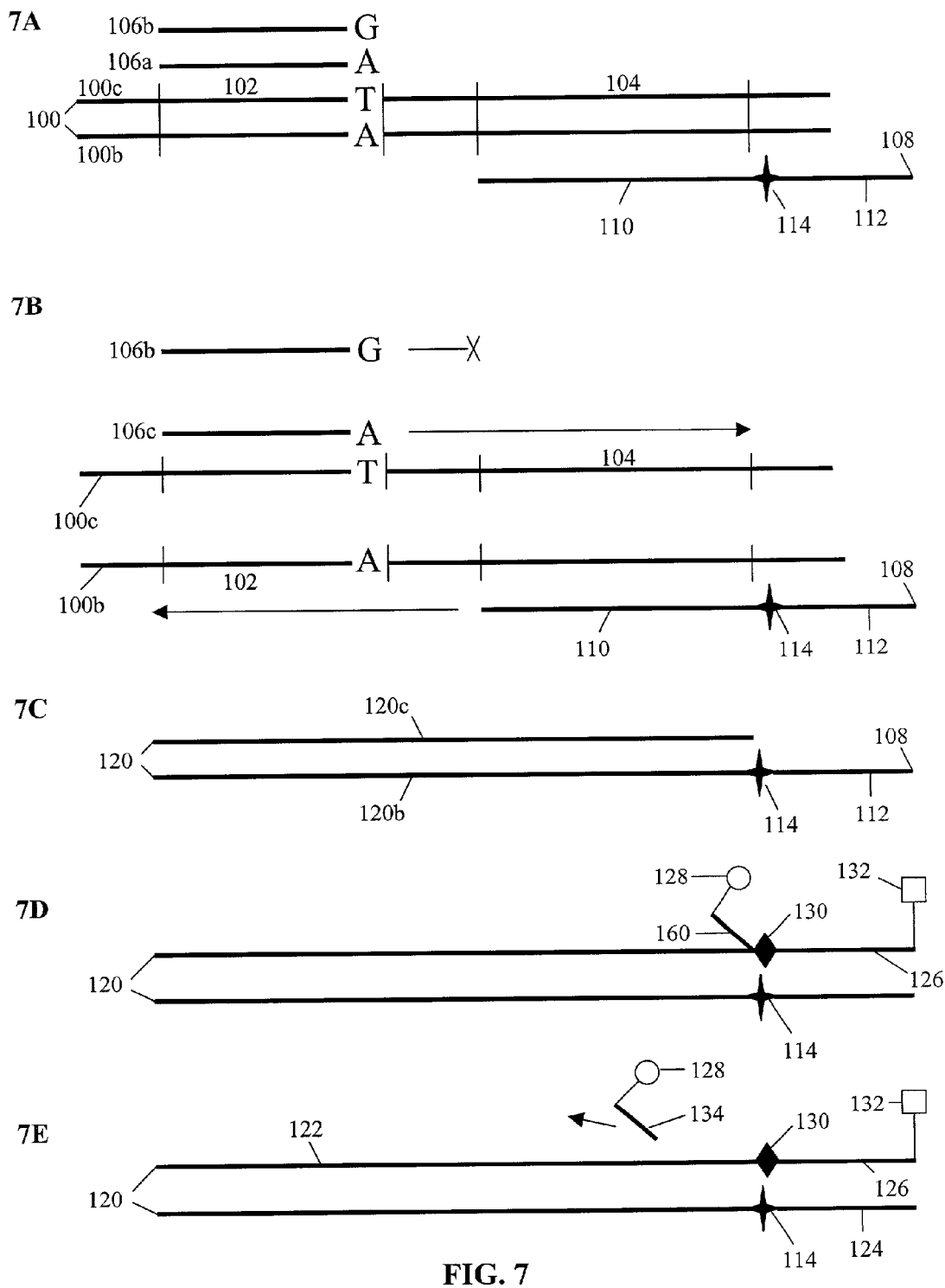
FIGS. 7A-7E schematically illustrate an assay method according to a sixth embodiment of the invention.

One example of an allele specific assay method is illustrated in FIG. 7. It will be recognized that the other assays discussed herein can be used or modified for allele-specific assays. Referring to FIG. 7A, a sample is suspected to contain target nucleic acid 100, the target nucleic acid 100 including a first portion 102 and a second portion 104. As shown, target nucleic acid 100 is a double-stranded molecule comprised of strands 100b and 100c.

Referring to FIG. 7B, the sample is contacted with two or more allele-specific first primers 106a, 106b and a second primer 108 as illustrated. One of the allele-specific first primers 106a is complementary to the first portion 102 of the target nucleic acid 100. The other allele specific primer(s) 106b are not fully complementary to the first portion 102 of the target nucleic acid 100. The second primer 108 includes a first region 110 and a second region 112, the first region 110 comprising a sequence that is complementary to the second portion 104 of the target nucleic acid 100. The second region 112 of the second primer 108 includes a non-natural base 114. The second region 112 is not complementary to the target nucleic acid 100.

In addition to the first primers and the second primer, the sample is also contacted with a polymerase and subjected to polymerase chain reaction (PCR), as herein described. If the target nucleic acid 100 is present in the sample, the complementary portion of the allele-specific first primer 106a and the complementary portion of the second primer 108 anneal to the corresponding regions 102 and 104 of the target nucleic acid 100 following standard base-pairing rules.

As shown in FIG. 7B, the polymerase is used to synthesize a single strand from the 3'-OH end of each primer 106a, 108, using PCR, or Fast-shot.TM. amplification. That is, allele specific first primer 106a is used to synthesize strand 102c that is complementary to at least a portion of strand 100c of the target nucleic acid 100, and the second primer 108 is used to synthesize strand 120b that is complementary to at least a portion of strand 100b of the target nucleic acid 100. Allele-specific first primer 106b does not substantially extend because it is not fully complementary to the target nucleic acid 100. The polymerase chain reaction is allowed to proceed for the desired number of cycles to obtain an amplification product 120 shown in FIG. 7C. The assay then proceeds as described for the assay illustrated in FIG. 1.

Kits

Reagents employed in the methods of the invention can be packaged into diagnostic kits. Diagnostic kits include labeled reporter, first primer, and second primer. In some embodiments the kit includes non-natural bases capable of being incorporated into an elongating oligonucleotide by a polymerase. In one embodiment, the non-natural bases are labeled. If the oligonucleotide and non-natural base are unlabeled, the specific labeling reagents can also be included in the kit. The kit can also contain other suitably packaged reagents and materials needed for amplification, for example, buffers, dNTPs, or polymerizing enzymes, and for detection analysis, for example, enzymes and solid phase extractants.

Reagents useful for the methods of the invention can be stored in solution or can be lyophilized. When lyophilized, some or all of the reagents can be readily stored in microtiter plate wells for easy use after reconstitution. It is contemplated that any method for lyophilizing reagents known in the art would be suitable for preparing dried down reagents useful for the methods of the invention.

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLES

Example 1

Primer Design

The symbols indicated in the sequence of the nucleic acid components are as follows: A=deoxyadenylate; T=deoxythymidylate; C=deoxycytidylate; G=deoxyguanylate; X=deoxy-iso-cytosine (d-isoC); Y=deoxy-iso-guanine (d-isoG); P=nucleotide of first primer complementary to polymorphic nucleotide in target nucleic acid; B=3' modification of reporter nucleic acid by addition of BiotinTEG CPG (Glen Research, Sterling, Va.) to 3' end that functions to block nucleic acid polymerase and extension of the reporter; Q=signal quenching element (5'-5-[(N-4'-carboxy-4(dimethylamino)-azobenzene)-aminohexyl-3-acrylimido]-2'-deoxyUridine (Dabcyl dT; Glen Research, Sterling, Va.) incorporated into reporter by addition of 5'-Dimethoxytrityloxy-5-[(N-4'-carboxy-4(dimethylamino)-azobenzene)-aminohexyl-3-acrylimido]-2'-deoxyUridine-3'-[(2-cyanoethyl)-(N,N-diisopropyl)]-phosphoramidite (Dabcyl dT; Glen Research, Sterling, Va.); FAM=Signal generating element (6-carboxyfluorescein (6-FAM); Glen Research, Sterling, Va.). Underlining indicates the portion of the nucleic acid component that is not complimentary to the template.

The designs of the nucleic acid components are shown below:

| Nucleic Acid Component | Sequence | SEQ ID NO |
| --- | --- | --- |
| Reporter | 5'-FAM-TYQCCTGTCTGC-3' | SEQ ID NO: 1 |
| First Primer | 5'-GGCCAGCATAAGCCM-3' | SEQ ID NO: 2 |
| Second Primer | 3'-GTTGCTTTTGTCGACTACC<u>AXAGGACAGACG</u>-5' | SEQ ID NO: 3 |

The first primer was designed to have a $T_m$ of approximately 60° C. The second primer was designed to have a $T_m$ of approximately 61° C. $T_m$ can be estimated using a variety of known techniques including Peyret et al., Biochemistry, 38, 3468-77 (1999), incorporated herein by reference.

Hybridization conditions were as follows:

| Component | Concentration |
| --- | --- |
| $Na^+$ | 0.04 mol/L |
| $Mg^{2+}$ | 0.002 mol/L |
| First Primer | 0.2 μmol/L |
| Second Primer | 4.0 μmol/L |

A 3' G was avoided in designing the allele specific primer due to the tendency of Taq polymerase to extend G mismatches.

The first region, or the 3' end, of the second primer was complimentary to the second portion, or downstream region, of a target nucleic acid sequence. The location of the second primer on the target nucleic acid sequence provided a gap, or a region, of the target nucleic acid that is between the 3' ends of the first and second primers, which can be from 0 to about 5 nucleotides. In synthesizing the second primer, incorporation of the iso-cytosine nucleoside, in the second region of the primer was carried out using standard DNA synthesis conditions.

Example 2

Allele Specific PCR

The following nucleic acid components were used in a fluorescence-based PCR reaction:

| Nucleic Acid Component | Sequence | SEQ ID NO: |
|---|---|---|
| Reporter | 5'-FAM-TYQCCTGTCTGC-3' | SEQ ID NO: 1 |
| First Primer, C specific | 5'-GGCCAGCATAAGCCC-3' | SEQ ID NO: 4 |
| First Primer, A specific | 5'-GGCCAGCATAAGCCA-3' | SEQ ID NO: 5 |
| Second Primer | 3'-GTTGCTTTTGTCGACTACC<u>AXAGGACAGACG</u>-5' | SEQ ID NO: 3 |
| Template, G | 3'-GGGAATGCAGTTCGATCAGTGAAACGAACGTTCTGACCTTTAAGT-5'<br>5'-CCCTTACGTCAAGCTAGTCACTTTGCTTGCAAGACTGGAAATTCA-3' | SEQ ID NO: 6<br>SEQ ID NO: 7 |
| Template, A | 3'-GGGAATGCAGTTCGATCAGTTAAACGAACGTTCTGACCTTTAAGT-5'<br>5'-CCCTTACGTCAAGCTAGTCAATTTGCTTGCAAGACTGGAAATTCA-3' | SEQ ID NO: 8<br>SEQ ID NO: 9 |

The working concentration (1×) of components in PCR reaction for individual 20 µl PCR reaction volumes is shown below:

| Component | 1X Conc. |
|---|---|
| Tris pH 8.0 | 10 mM |
| Bovine Serum Albumin | 0.01% |
| Triton ™ X-100 | 0.01% |
| Herring Sperm DNA | 0.1 µg/ml |
| Potassium acetate | 40 mM |
| $MgCl_2$ | 2 mM |
| Amplitaq Gold ™ DNA polymerase | 1 U/rxn |
| dATP | 50 µM |
| dGTP | 50 µM |
| dCTP | 50 µM |
| dTTP | 50 µM |
| First Primer | 0.2 µM |
| Second Primer (A or B) | 0.2 µM |
| Reporter | 0.4 µM |

All components were thawed on ice and gently mixed together. A 10× PCR Buffer was prepared and composed of 100 mM Tris pH 8.0, 0.1% BSA, 0.1% Triton X-100, 1 mg/ml degraded herring sperm DNA (Sigma D-3159), 400 mM potassium acetate, and 20 mM $MgCl_2$. A master mix and an allele specific mix were prepared by adding the reagents in the proportions indicated below:

Master Mix

| Component | Volume per Reaction (µL) | Concentration in Reaction |
|---|---|---|
| $dH_2O$ | 11.36 | — |
| 10X PCR Buffer | 2 | 1X |
| dNTPs 25 mM | 0.04 | 50 µM |
| Reporter | 0.2 | 0.4 µM |
| Second primer | 0.2 | 0.2 µM |
| Amplitaq Gold ™ DNA polymerase | 0.2 | 1 U |

The final volume of the reaction was 20 µL. 5 µL of target nucleic acid was added to 15 µL of the combined Master Mix and first primer. The target nucleic acid volume can be increased or decreased according to end user needs by adjusting the amount of water added in the Master Mix. 5 µL is a convenient volume to deliver with a multichannel pipetor. The Allele Specific Mixes were prepared as shown below:

Allele Specific Mixes

| Component | Volume per Reaction (µL) | Concentration in Reaction |
|---|---|---|
| First Primer | 1 | 0.2 µM |
| Master Mix | 14 | — |

The assay plates were prepared as follows: 15 µL of an allele specific mix (as defined above) was aliquoted into a 96-well assay plate. (An allele specific mix can be prepared and run for each specific first primer that is to be used in the assay). The target nucleic acid samples were added in duplicate in a volume of 5 µL to each well containing an allele specific mix. A certain number of wells were reserved as controls; a negative control (no target nucleic acid) should be run with each of the allele specific mixes. Subsequent to the target nucleic acid addition, the reactions were overlaid with 20 µL of mineral oil and the assay plate was transferred to a DNA thermal cycler. Hands on time of this procedure was greatly reduced by the use of a multichannel pipetor.

The thermal cycling parameters for the assay plates are shown below:

| Cycle # | Step | Temp | Time |
|---|---|---|---|
| 1 | 1 | 95° C. | 12 min. |
| 2-38 | 1 | 95° C. | 1 sec. |
|  | 2 | 58° C. | 1 sec. |
| 39 | 1 | 49° C. | 20 min. |

Following PCR cycling reactions, the assay plates were tested for emission of a fluorescence signal. The assay plates were transferred to a PerSeptive Biosystems Cytofluor™ 4000 fluorescence plate reader and the instrument set to read from the top of the plate. The parameters for the plate reader were as follows: excitation filter settings at 485±10 nm; emission filter settings at 530±12.5 nm, and PMT gain set to 50. The samples were then read.

Table 1 shows readings obtained using the allele specific primers.

TABLE 1

|  | C-specific first primer | | | A-specific first primer | | |
| --- | --- | --- | --- | --- | --- | --- |
| Copy number, target nucleic acid | 3000 | 300 | 30 | 3000 | 300 | 30 |
| RFUs: G-target nucleic acid | 1847 | 1071 | 131 | 1 | 1 | |
| RFUs: T-target nucleic acid | 7 | 1 | | 1464 | 1066 | 176 |

RFU = Relative Fluorescence Unit

Example 3

Comparison of "Fast-shot™" Amplification Versus Standard PCR in SNP Detection

This example shows the relative levels of allelic discrimination between "Fast-shot™" amplification and traditional PCR cycling parameters by varying the target levels over three orders of magnitude. Fast-shot™ amplification involves cycling between the denaturation and annealing temperatures of the primers with stops at these temperatures for very short periods of time (for example, 1 second).

The following nucleic acid components were used:

```
Nucleic Acid
Component    Sequence                                          SEQ ID NO First Primer, 5'-CCCTTACGTCAAGCTAGTCAC-3'                      SEQ ID NO: 10
C specific
First Primer, 5'-CCCTTACGTCAAGCTAGTCAA-3'                      SEQ ID NO: 11
A specific
Second        3'-ACGAACGTTCTGACCTTTAAGT-FAM-5'                 SEQ ID NO: 12
Primer
Template, G  3'-GGGAATGCAGTTCGATCAGTGAAACGAACGTTCTG            SEQ ID NO: 6
             ACCTTTAAGT-5'
             5'-CCCTTACGTCAAGCTAGTCACTTTGCTTGCAAGACT           SEQ ID NO: 7
             GGAAATTCA-3'
Template, A  3'-GGGAATGCAGTTCGATCAGTTAAACGAACGTTCTG            SEQ ID NO: 8
             ACCTTTAAGT-5'
             5'-CCCTTACGTCAAGCTAGTCAATTTGCTTGCAAGA             SEQ ID NO: 9
             CTGGAAATTCA-3'
```

The template nucleic acid concentration was in attomol range. The working concentration (1×) of components in PCR reaction for individual 20 μl PCR reaction volumes are shown below.

| Component | 1X Conc. |
| --- | --- |
| Tris pH 8.0 | 10 mM |
| Bovine Serum Albumin | 0.01% |
| Triton ™ X-100 | 0.01% |
| Herring Sperm DNA | 0.1 μg/ml |
| Potassium acetate | 40 mM |
| $MgCl_2$ | 2 mM |
| Amplitaq ™ Gold or Amplitaq ™ Stoffel DNA polymerase | 1 U/rxn |
| dATP | 50 μM |
| dGTP | 50 μM |
| dCTP | 50 μM |
| dTTP | 50 μM |
| First Primer | 0.2 μM |
| Second Primer (A or B) | 0.2 μM |
| Reporter | 0.4 μM |

The PCR reactions were prepared using the same procedure as described in Example 2.

The following PCR parameters were utilized for "fast shot" PCR:

| Cycle # | Step | Temp | Time |
| --- | --- | --- | --- |
| 1-25 | 1 | 95° C. | 1 sec. |
| | 2 | 61° C. | 1 sec. |

The following PCR parameters were utilized for traditional PCR:

| Cycle # | Step | Temp | Time |
| --- | --- | --- | --- |
| 1-25 | 1 | 95° C. | 30 seconds |
| | 2 | 61° C. | 30 seconds |

Amplitaq™ Gold is a 5'->3' exonuclease positive Taq polymerase and Amplitaq™ Stoffel is a 5'->3' exonuclease deficient Taq polymerase.

The data shown in Table 2 shows the relative levels of allelic discrimination between "Fast-shot™" amplification and traditional PCR cycling parameters by varying the target nucleic acid levels over three orders of magnitude. By comparison of the band intensities of the specific reactions (C-primer/G-target, and A-Primer/T-target) and the mismatched reactions (C-primer/T-target, and A-Primer/G-target), levels of allelic discrimination can be determined. Table 2 summarizes the levels of discrimination seen in these experiments.

TABLE 2

| | A-specific first primer | | C-specific first primer | |
| --- | --- | --- | --- | --- |
| | Fast-shot ™ amplification | Traditional PCR | Fast-shot ™ amplification | Traditional PCR |
| Amplitaq ™ Gold | >1:1000 | >1:1000 | 1:1000 | 1:1 |
| Amplitaq ™ Stoffel | >1:1000 | >1:1000 | 1:1000 | 1:100 |

As shown in the results, certain 3' mismatches are more readily extended by nucleic acid polymerases. In this case under traditional PCR parameters the C/T mismatch is extended to a much greater extent than the A/G mismatch by both 5'->3' exonuclease containing Amplitaq™ Gold and 5'->3' exonuclease deficient Amplitaq™ Stoffel DNA polymerases. By employing "Fast-shot™" amplification a 1:1000 level of discrimination between both alleles is achieved using either enzyme.

Example 4

PCR and Reporter Annealing

The following nucleic acids were used for fluorescence-based PCR reactions:

| Nucleic Acid Component | Sequence | SEQ ID NO: |
|---|---|---|
| Reporter A | 5'-FAM-TYQCCTGTGTGC-3' | SEQ ID NO: 1 |
| Reporter B | 5'-FAM-XYQCCTGTCTGC-3' | SEQ ID NO: 13 |
| First Primer | 5'-CTCATGGACCCCCATAC-3' | SEQ ID NO: 14 |
| Second Primer A | 3'-GGTGCGAGGTCAATCGAXAGGACAGACG-5' | SEQ ID NO: 15 |
| Second primer B | 3'-GGTGCGAGGTCAATCGYXAGGACAGACG-5' | SEQ ID NO: 16 |
| Template | 5'-CCTCATGGACCCCCATACATATTGTCCACGCT-CCAGTTAGC-3' | SEQ ID NO: 17 |

2 fM of synthetic template controls in 2 µg/ml herring sperm DNA, and 2 mM MOPS pH 7.0 were used.

The reaction components for the following reaction are shown below.

| Component | 1X Conc. |
|---|---|
| Tris pH 8.0 | 10 mM |
| Bovine Serum Albumin | 0.01% |
| Triton ™ X-100 | 0.01% |
| Herring Sperm DNA | 0.1 µg/ml |
| Potassium acetate | 40 mM |
| MgCl$_2$ | 2 mM |
| Amplitaq ™ Gold DNA polymerase | 1 U/rxn |
| dATP | 50 µM |
| dGTP | 50 µM |
| dCTP | 50 µM |
| dTTP | 50 µM |
| First Primer | 0.2 µM |
| Second Primer (A or B) | 0.2 µM |
| Reporter | 0.4 µM |

AMPLITAQ GOLD™ 5 U/µl was obtained from Perkin Elmer.

Reagents were thawed and gently mixed and two master mixes were prepared. One master mix (A) contained the second primer A and the reporter A. The other master mix (B), contained the second primer B and the reporter B. The Master Mixes were prepared as shown below.

| | Master Mix | |
|---|---|---|
| Component | Volume per Reaction (µL) | Concentration in Reaction |
| dH$_2$O | 11.36 | — |
| 10X PCR Buffer | 2 | 1X |
| dNTPs 25 mM | 0.04 | 50 µM |
| Reporter | 0.2 | 0.4 µM |
| Second primer | 0.2 | 0.2 µM |
| Amplitaq Gold ™ DNA polymerase | 0.2 | 1 U |
| First primer | 1 | 0.2 µM |

The final volume of the reaction was 20 µl. 5 µl of target nucleic acid was added to 15 µl of combined Master Mix and First primer. The target nucleic acid volume can be increased or decreased according to end user needs by adjusting the amount of water added in the Master Mix.

Assay plates were prepared as follows: 15 µl of a master mix was aliquoted to wells of a 96-well assay plate (Low Profile Multiplate™ 96 well; MJ Research, MLL-9601). Target nucleic acid samples were added in duplicate in a volume of 5 µl to wells containing the master mix. To some wells, 5 µl of water, rather than target nucleic acid, was added as a negative control. Subsequent to target nucleic acid or negative control addition, the reactions were overlaid with 20 µl of mineral oil Mineral Oil (light white oil; Sigma, M-3516) and the assay plate was transferred to a DNA thermal cycler.

Thermal cycling parameters for the assay plates are shown below:

| Cycle # | Step | Temp | Time |
|---|---|---|---|
| 1 | 1 | 95° C. | 12 min. |
| 2-38 | 1 | 95° C. | 1 sec. |
| | 2 | 58° C. | 1 sec. |
| 39a. | 1 | 49° C. | 20 min. |
| 39b. | 1 | 51° C. | 20 min. |
| 39c. | 1 | 53° C. | 20 min. |
| 39d. | 1 | 55° C. | 20 min. |
| 40. | 1 | 4° C. | hold |

As an additional control, some of the samples were not subjected to PCR thermal cycling.

Following PCR cycling reactions, the assay plates were tested for emission of fluorescence signal. The assay plates were transferred to a PerSeptive Biosystems Cytofluor™ 4000 fluorescence plate reader and the instrument set to read from the top of the plate. The parameters for the plate reader are as follows: excitation filter settings at 485±10 nm; emission filter settings at 530±12.5 nm, PMT gain set to 50. The samples were then read. The assay plates were also tested for the emission of fluorescent signal prior to PCR amplification as a control.

The samples were subsequently run on 10% native polyacrylamide gel electrophoresis (PAGE) followed by ethidium bromide staining to detect the presence of an amplification product and to confirm the fluorescence readings taken from the assay plates.

The results of the fluorescence detection of the target nucleic acid template is shown Table 3. The amplification product was also detected by ethidium bromide staining after PAGE. In Table 3, a (−) indicates the absence and a (+) indicates the presence of the template or process of thermal cycling. The numbers indicated in Table 3 indicate the relative fluorescence units (RFUs).

TABLE 3

| Master mix | A | A | A | A | A | A | B | B | B | B | B | B |
|---|---|---|---|---|---|---|---|---|---|---|---|---|
| Target | + | + | − | − | − | − | + | + | − | − | − | − |
| Thermal cycling | + | + | + | + | − | − | + | + | + | + | − | − |
| T = 0 | 198 | 203 | 208 | 206 | 205 | 208 | 170 | 173 | 172 | 173 | 166 | 170 |
| 49° C. | 1272 | 1440 | 234 | 243 | 240 | 235 | 470 | 494 | 382 | 398 | 264 | 267 |
| 51° C. | 1543 | 1725 | 248 | 252 | 257 | 244 | 603 | 644 | 387 | 403 | 279 | 273 |
| 53° C. | 1540 | 1666 | 250 | 253 | 255 | 250 | 718 | 773 | 382 | 403 | 283 | 284 |
| 55° C. | 1590 | 1724 | 261 | 263 | 273 | 264 | 806 | 866 | 380 | 399 | 285 | 287 |

As shown in Table 3, several second primers and reporters can be successfully used to detect the presence of a target nucleic acid sequence present in a sample. The second primer/reporter combination in master mix A produced a more robust signal than the second primer/reporter combination in master mix B. (It will also be recognized that master mix A included more PCR product than master mix B, which accounts for some of the difference in signal intensity.) The difference in signal intensity appeared to be greater at lower temperatures. However, the second primer and reporter in master mix B produced a signal above background at all hold temperatures, and therefore were sufficient for detection and quantification of the target nucleic acid sequence.

PCR products were separated by PAGE and stained with ethidium bromide or scanned for fluorescein fluorescence using a Molecular Dynamics (Sunnyvale, Calif.) 595 Fluor-oimager™. For both the master mix A and the master mix B reactions, an amplification product was detected by ethidium bromide staining after PAGE in lanes corresponding to reactions containing template (+). An amplification product was not seen in lanes corresponding to reactions not containing a nucleic acid template (−). These results confirmed that the increased fluorescence signals detected in the above assay were due to presence of nucleic acid target sequence in the sample.

The differences in the signal intensity between the second primer/reporter combination of master mix A and second primer/reporter combination of master mix B were likely due to the degradation of the non-natural base, isoC, during the reaction. The non-natural base, isoC, tends to degrade at high temperatures in solutions containing nucleophiles, such as solutions containing Tris buffer. However, the results presented above do show that isoC is suitable for use in Tris buffer at high temperatures.

To optimize the efficiency of the methods according to the invention, polymerases that do not require a hot start activation and buffers that are non-nucleophilic in nature should be used when the non-natural base, isoC, is used.

Example 5

Dry Down Plate Preparation

Some or all of the reagents necessary for the methods of the invention can be dried down for convenient storage and ease of use. For example, reactions can be set up as master mixes containing 40 mM Potassium acetate, 20 mM $MgCl_2$, 50 μM dNTPs (dATP, dCTP, dGTP, dTTP), 1 unit/reaction AMPLI-TAQ GOLD™ polymerase, a sugar as described below, and 8 μM reporter. The Master Mix can then be aliquoted into the wells of 96 well microtiter plates and dried in a SPEED-VAC™ (Savant Instruments, Holbrook, N.Y.) for 45-50 minutes (no heat). After desiccation, plates can be covered with MICROSEAL A™ film (MJ Reasearch, Waltham, Mass.) placed in a vacuum bag with 1 DESIPAK™ (Trocken, Germany), and the bag can be filled with argon and sealed with a FOOD SAVER™ (Tilia, San Franscisco, Calif.). Various sugars (Mannose, Raffinose, Sucrose, and Trehalose (Sigma, St. Louis, Mo.)) at various concentrations (1%, 2%, 5%, and 10% by weight) can be used.

Reaction mixes can be reconstituted in water containing nucleic acid target, first primer, second primer, and optionally reporter. The reaction mixes can then be subjected to PCR In this way, the dried down reagents can be readily reconstituted and successfully used in PCR assays. Such lyophilized reagents can be stored at room temperature for extended periods of time. Some or all of the reagents can be dried down. Some or all of the lyophilized reagents necessary for a given method of the present invention can be stored in wells of microtiter plates for later use after reconstitution.

Example 6

Assay Including PCR Incorporation of Non-natural Base

The following example illustrates a method for monitoring the accumulation of PCR product by quenching the signal of a label on the second primer by site specific incorporation (SSI) of a nucleotide triphosphate across the DNA duplex at a position near the label of the second primer. The labeled nucleotide triphosphate is incorporated into the elongating first primer during PCR extension. The label on the labeled nucleotide triphosphate is capable of quenching the label on the second primer. Alternatively fluorescence energy transfer (FRET) can be observed between the label of the second primer (donor dye) and the label of the reporter (acceptor dye). Detection of PCR product can be observed by exciting the donor dye and reading the emission of the incorporated acceptor dye.

The following nucleic acid components were used in the PCR reaction:

| Nucleic Acid Component | Sequence | SEQ ID NO: |
|---|---|---|
| First Primer | 5'-GTYATYTGCG-c3-TCGTGCGGTGCGTC-3' | SEQ ID NO: 18 |
| Second Primer A | 3'-TGTGTCGTGTCGTCCGAT-FAM 5' | SEQ ID NO: 19 |
| Second Primer B | 3'-TGTGTCGTGTCGTCCGXT-FAM 5' | SEQ ID NO: 20 |
| Template | 5'-TCGTGCGGTGCGTCACACAGCACAGCAGGC-3' | SEQ ID NO: 21 |

"c3" indicates a propyl spacer which was chemically installed in place of a nucleotide during synthesis of the first primer. The phosphoramidite used in the synthesis of the first primer was 3-O-Dimethyltrityl-propyl-1-[2-cyanoethyl)-(N, N-diisopropyl)]-phosphoramidite (Spacer Phosphoramidite C3; Glen Research, Sterling, Va.). Optionally, an oligonucleotide containing an identical nucleotide sequence, including nucleotide modifications, but lacking the propyl spacer can be used as a substitute for the first primer in the PCR reaction.

In design of these systems it is preferred that the labeled nucleotide triphosphate is complementary to a base near the label of the second primer A or B. When using a naturally occurring nucleotide base that is labeled, the ability to incorporate such a complementary base near the label of the second primer A or B is possible only in a limited number of cases. This is because all four naturally occurring nucleotide bases are likely to be incorporated at other positions. By using labeled non-natural bases, such as labeled isoG and isoC for example, the labeled non-natural base will be incorporated only opposite to a complimentary non-natural base, which can be placed near the label of the second primer A or B.

Systems for using labeled non-natural bases and naturally occurring nucleotide triphosphates utilize a naturally occurring nucleotide (dTTP) labeled a quencher dye (QSY7™) in an assay to detect or quantify the amount of target nucleic acid (template) present in a sample. For this example the labeled, naturally occurring nucleotide was incorporated into the first primer during PCR extension at a position opposite to, and near, the label (FAM) of the second primer A. A system for using a non-natural base, IsoG ($dG_{iso}TP$), labeled with a quencher dye (QSY7™) in an assay to detect or quantify the amount of target nucleic acid (template) present in a sample was also performed. For this example the labeled, non-natural nucleotide was incorporated into the first primer during PCR extension at a position opposite to isoC (X), which is near the label (FAM) of the second primer B. The chemical structures of the QSY7™ dTTP and QSY7™ $dG_{iso}$TP are shown below.

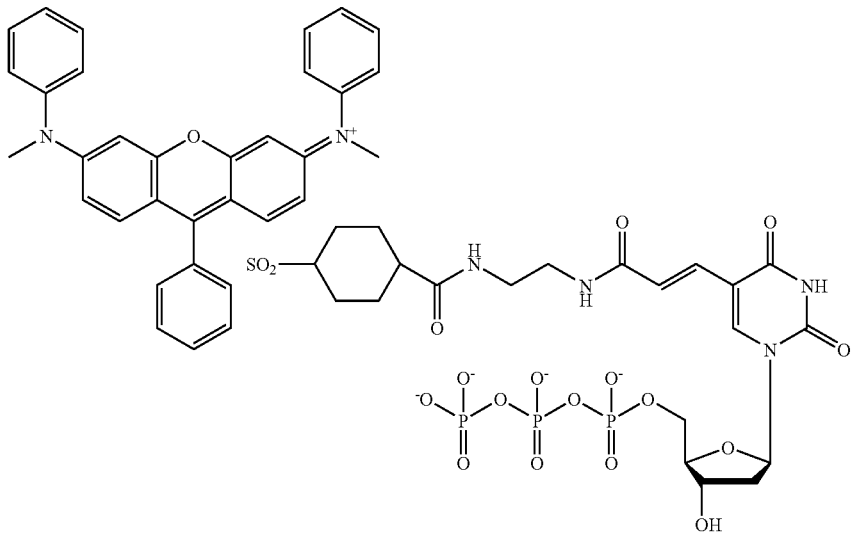

QSY 7 dTTP

-continued

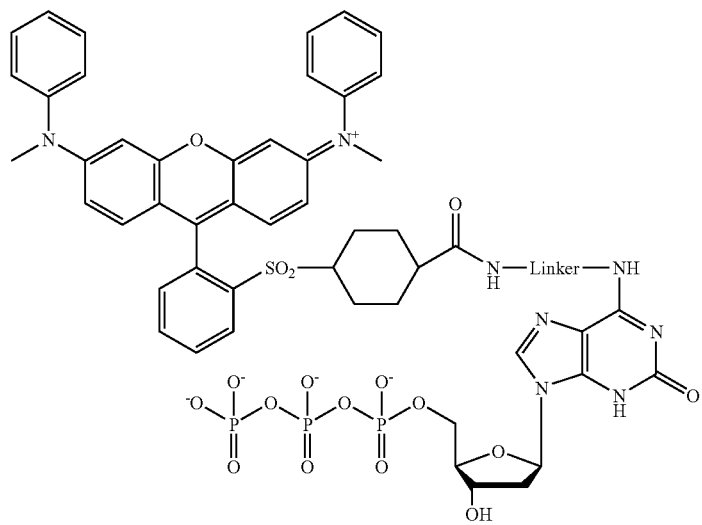

QSY 7 dG$_{iso}$TP

A PCR reaction was performed to demonstrate fluorescence quenching by site specific incorporation in PCR. PCR conditions: 0.2 µM first primer, 0.2 µM second primer A, 0.4 pM template nucleic acid, 50 µM dATP, dGTP, 10 mM Tris pH 8, 0.1% BSA, 0.1% Triton™ X-100, 0.1 µg/µl degraded herring sperm DNA, 40 mM KAc, 2 mM MgCl$_2$, 1 unit Klentaq™ DNA polymerase (Ab Peptides, St/Louis, Mo.), and 0 or 3.9 uM QSY7™ dTTP in a 25 µl reaction volume.

The PCR conditions used are shown below.

| Cycle # | Step | Temp | Time |
|---------|------|------|------|
| 1 | 1 | 95° C. | 2 min. |
| 2-36 | 1 | 95° C. | 1 sec. |
|  | 2 | 60° C. | 1 sec. |
| 37. | 1 | 70° C. | 6 sec. |

Reactions were analyzed for fluorescence on a Cytofluor™ 4000 fluorescence plate reader (485 nm excitation/530 nm emission) and by gel electrophoresis. The hold time of 6 seconds at 70° C. was used to obtain an accurate fluorescence reading. The results are presented in Table 4.

PCR reactions were resolved on a 10% native polyacrylamide gel scanned for 6FAM using a Typhoon™ fluorescence scanner (Molecular Dynamics, Sunnyvale, Calif.). The relative fluorescent units (RFU's) contained in product bands were 1,325,644 for (+) QSY7™ dTTP reaction and 41,462,945 for (−)QSY7™ dTTP reaction. The polyacrylamide gel was also stained with ethidium bromide (50 µg/ml in 10 mM Tris-HCl, 1 mM EDTA). Quantitation of product bands from ethidium bromide staining revealed 21,993 RFU's for the (+)QSY7TM dTTP reaction and 25,537 RFU's for the (−)QSY7™ dTTP reaction.

Table 4 shows net RFU's read in PCR reaction wells prior to and after 35 cycles of PCR.

TABLE 4

| PCR Cycles | (+)QSY7 ™ | (−)QSY7 ™ |
|---|---|---|
| 0 | 3726 | 3836 |
| 35 | 1200 | 4490 |

These results show a 27 fold reduction of fluorescence intensity when the labeled nucleotide triphosphate (QSY7™ dTTP) is incorporated into a duplex across from the fluoroscein label (FAM) of the second primer during PCR.

The nucleic acid components in this example were also utilized to demonstrate "real time" monitoring of PCR product accumulation by site specific incorporation (SSI).

The PCR conditions were as follows: 0.2 µM of first primer, 0.2 µM of second primer A, 0.33 pM of template, 50 µM dATP, dGTP, and dCTP, 10 mM Tris pH 8, 0.1% BSA, 0.1% Triton X-100, 0.1 µg/µl degraded herring sperm DNA, 40 mM KAc, 2 mM MgCl$_2$, 1 unit Klentaq™ DNA polymerase (Ab Peptides, St/Louis, Mo.), and 0 or 3 uM QSY7™ dTTP in a 15 µl reaction volume.

PCR conditions:

| Cycle # | Step | Temp | Time |
|---------|------|------|------|
| 1 | 1 | 95° C. | 2 min. |
| 2-X.* | 1 | 95° C. | 1 sec. |
|  | 2 | 60° C. | 1 sec. |
| X* + 1. | 1 | 70° C. | 6 sec. |

(*X = 6, 11, 16, 21, 26, 31, or 36)

Figure 14:
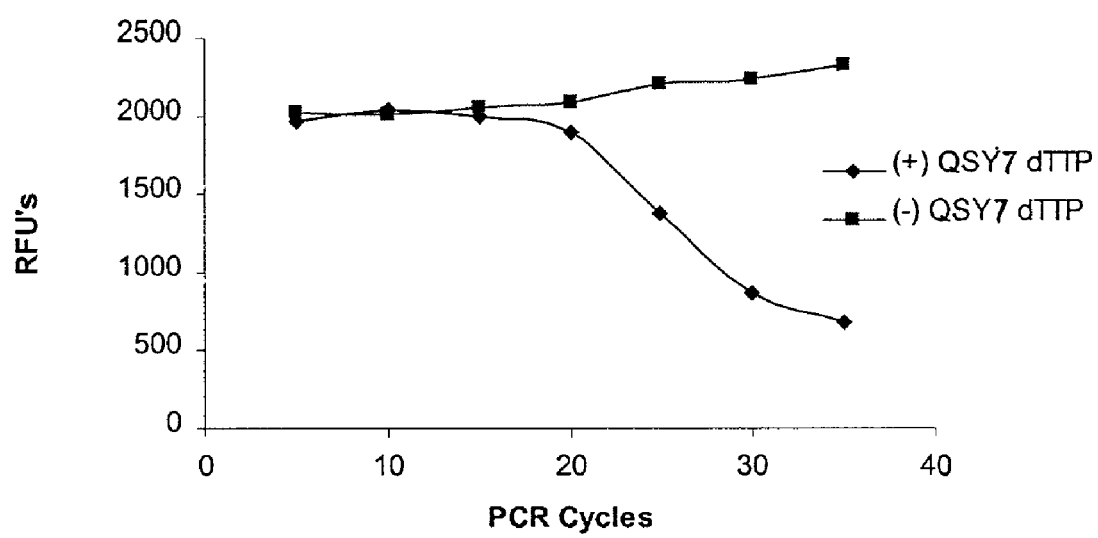
FIG. 14 is a graph demonstrating quenching of fluorescence in a PCR reaction by site specific incorporation of a quenching compound into a PCR amplification product, relative fluorescence units (RFU's) are indicated on the Y axis and the number of PCR cycles are indicated on the X axis.

Reactions were analyzed for fluorescence (485 nm excitation/530 nm emission) on a Cytofluor™ 4000 fluorescence plate reader (PE Biosystems, Foster City, Ca.) and by gel electrophoresis. FIG. 14 illustrates the results.

FIG. 14 shows the relative fluorescence vs. PCR cycle number. QSY7™ dTTP containing reactions were also examined by gel electrophoresis (5 µl on a 10% native polyacrylamide gel). Staining of the gel with ethidium bromide (50 µg/ml in 10 mM Tris-HCl, 1 mM EDTA) indicated accumulation of the expected product. Fluorescence of the QSY7™ dTTP containing reactions agree with the appearance and accumulation of PCR products revealed by gel analysis. These results also showed that correlating rounds of PCR versus quenching to target concentration can quantify the amount of target present in a sample. For example, the more target that is present, the faster quenching will occur.

A hold time of 6 seconds at 70° C. was used for an accurate fluorescence measurement in the Example described above.

Such a hold time is not required for the requisite number of bases to be incorporated across the gap between primers and across the primer. If fluorescence is not to be measured, no hold time at 70° C. is needed. If a hold time is required for obtaining a fluorescence reading, or any other suitable measurement, it is preferred that the hold temperature be a temperature above which the first primer can effectively hybridize to the target sequence. In one embodiment, the hold temperature is greater than 10° C. over the melting temperature of the first primer.

Example 7

Synthesis of Labeled Non-natural Bases

Figure 15:
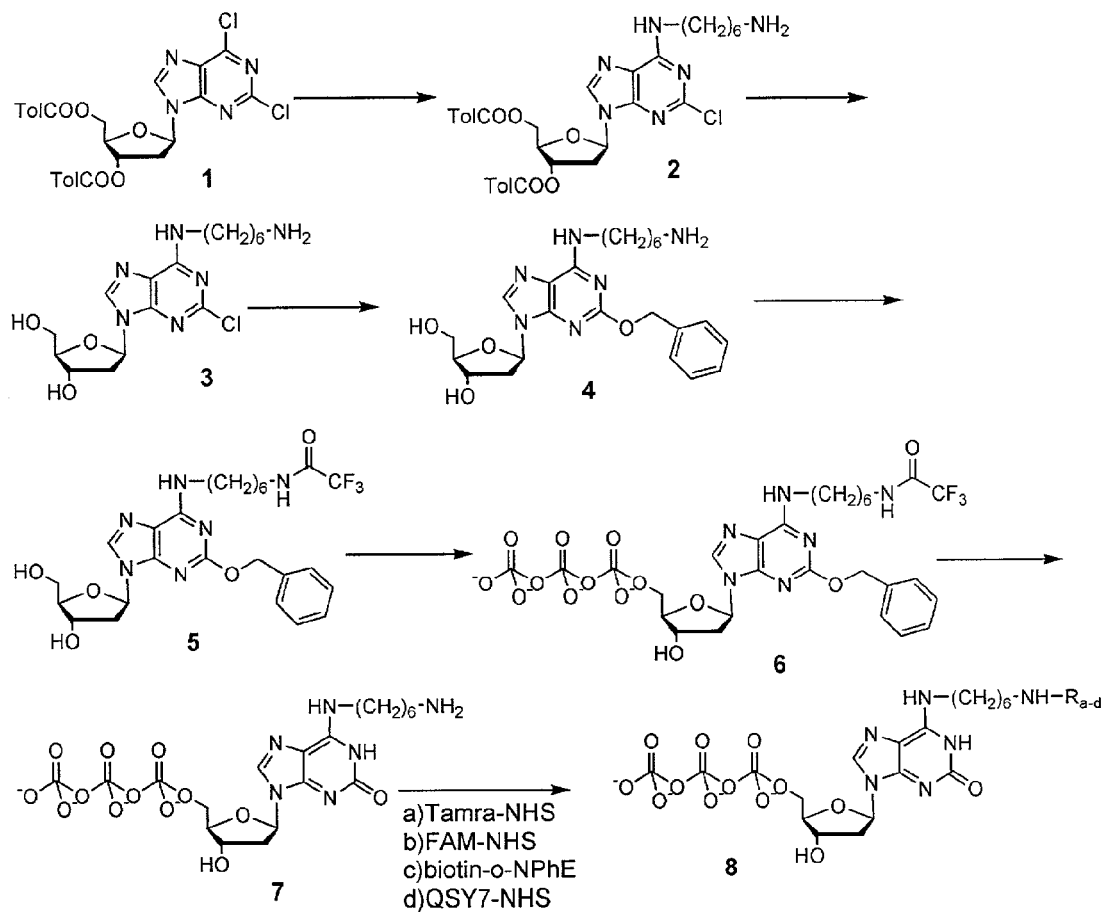
FIG. 15 schematically illustrates a synthesis scheme for the preparation of labeled non-natural bases according to Process A.
Figure 15:
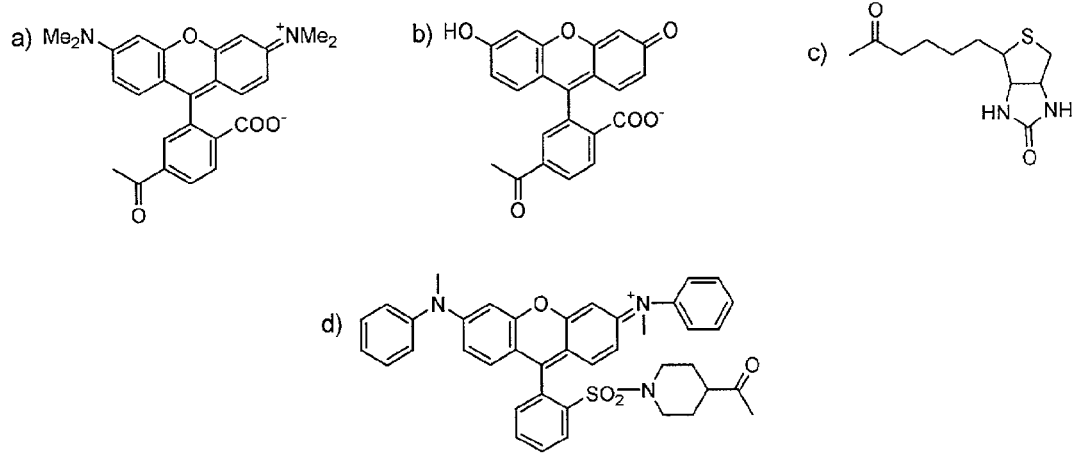
Figure 16:
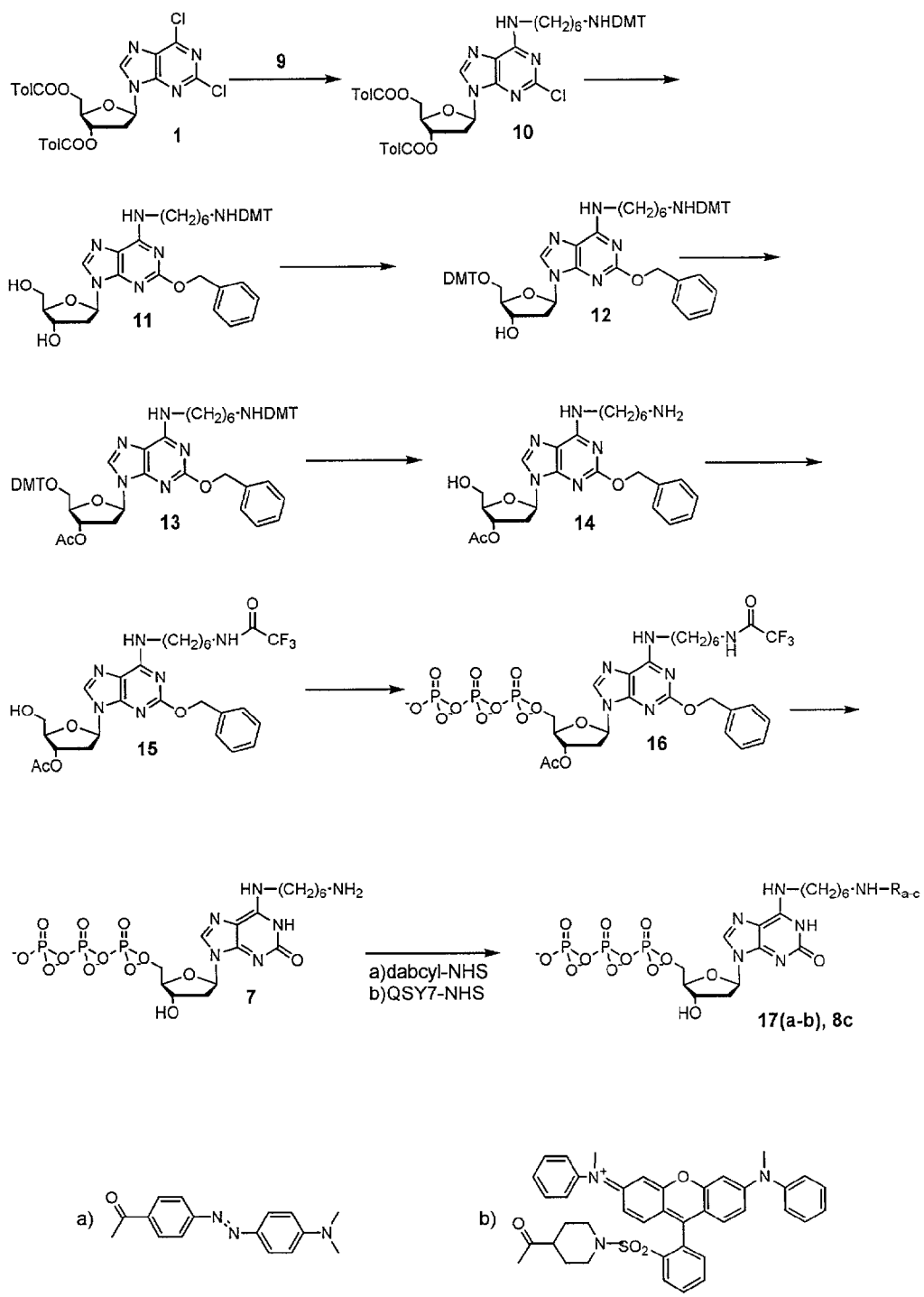
FIG. 16 schematically illustrates a synthesis scheme for the preparation of labeled non-natural bases according to Process B.

Labeled non-natural bases suitable for the methods and kits of the invention can be made by a variety of methods. Two synthesis schemes are provided for labeled-deoxyisoGuanosine 5'-Triphosphates: Process A is illustrated in FIG. 15 and the compounds (compounds 1-8, including $8_a$-$8_d$) of Process A are described in Section A; Process B is illustrated in FIG. 16 and the compounds (compounds 9-18) of Process B are described in Section B Section A For the following chemical reactions involving the synthesis of labeled -deoxyisoGuanosine 5'-Triphosphates using Process A, Sephadex™ DEAE cellulose, omega-aminobutyl agarose and tributylammonium pyrophosphate were purchased from Sigma; biotin 2-nitrophenyl ester, 6-carboxyfluorescein N-hydroxysuccinimide ester, and 6-carboxytetramethylrhodamine N-hydroxysuccinimide ester were purchased from Berry & Associates; QSY7™ N-hydroxysuccinimide ester was purchased from Molecular Probes; all other chemicals were purchased from Aldrich Chemical Co. or Fisher Chemical Co. and were used without further purification. Solvents were dried over 4 Å molecular sieves. Reactions were carried out under dry argon in an oven-dry glass system. "Evaporation" refers to removal of volatile solvents with a membrane pump. Column chromatography was performed with silica gel (230-425 mesh).

6-(6-Aminohexyl)-amino-2-chloropurine 2'-deoxy-3',5'-ditolulriboside 2:

2,6-Dichloro-2'-deoxy-3',5'-ditoluylriboside 1 (I equiv., 5 mmol, 2.705 g), dissolved in DMF (100 ml), was added at room temperature to a stirred solution of hexamethylenediamine (20 equiv., 100 mmol, 11.60 g) in 200 ml DMF over 40 minutes. The solution was stirred at 50° C. for 2.5 hours, then cooled to room temperature, concentrated and the residue extracted (water/ethyl acetate). The organic layer was washed with water (5×50 ml), dried ($Na_2SO_4$), and the solvent was evaporated to give 2.673 g (4.308 mmol, 86%) product 2 as a foam.

6-(6-Aminohexyl)-amino-2-chloropurine 2'-deoxyriboside 3:

The above-obtained compound 2 (4.308 mmol, 2.673 g) was dissolved in 20 ml methanol, saturated at 0° C. with ammonia, and placed in a sealed tube. It was heated at 80° C. for 1 hour and cooled to 0° C. The tube was opened and the solvent evaporated under membrane pump vacuum. The residue was treated with ether/hexane three times, and the obtained powder was dried in vacuum and used in next step without further purification.

6-(6-Aminohexyl)-amino-2-phenoxypurine 2'-deoxyriboside 4:

The above-obtained powder (max. 4.308 mmol) was dissolved in DMF (15 ml) and a solution of NaH (12 equiv., 51.69 mmol, 2.068 g of a 60% dispersion in mineral oil) in benzylalcohol (43 ml) was added. It was stirred at 100° C. for 2 hours and cooled to room temperature. Acetic acid was then added (12 equiv.) to neutralize the reaction mixture. The resultant solution was filtered over Celite™, the filtrate was evaporated, and the obtained residue was used in the next step without further purification.

6-(6-Trifluoroacetylamidohexyl)-amino-2-phenoxypurine 2'-deoxyriboside 5:

The above-obtained product was dissolved in a mixture of methanol (30 ml)/ethyl trifluoroacetate (30 ml) and stirred at room temperature for 24 hours. The solvent and excess ethyl trifluoroacetate was removed by evaporation, and the residue was purified by column chromatography using a one step gradient of 1.5% methanol in chloroform, then 17.5% methanol in chloroform. Yield: 626 mg (1.134 mmol, 26% for 3 steps).

6-(6-Trifluoroacetylamidohexyl)-amino-3-phenoxypurine 2'-deoxyriboside 5'-triphosphate 6:

1,2,4-Triazole (4.5 equiv., 0.585 mmol, 40 mg) was dissolved in a mixture of 0.5 ml acetonitrile/4.5 equiv. triethylamine (0.585 mmol, 0.081 ml), and the flask was placed in an ice bath. Phosphorus oxychloride (1.5 equiv., 0.195 mmol, 0.018 ml) was added, and it was stirred at room temperature for 30 minutes. It was filtrated, the solid was washed with a minimum amount of acetonitrile, and the filtrate was added to compound 5 (1 equiv., 0.13 mmol, 72 mg). It was stirred for 30 minutes at room temperature, then a solution of tributylammonium pyrophosphate (89 mg) in DMF (2 ml) was added and stirring continued for 19 hours. Then, water (1 ml) was added to hydrolyze the remaining triazolide group. After stirring for 30 minutes, the reaction mixture was concentrated in vacuum at 30° C. and purified by column chromatography on DEAE cellulose using a gradient of 0.05M-0.5M TEAB buffer. The product elutes at a buffer concentration of 0.4-0.5M. The fractions containing the product were evaporated at 30° C. and used further.

$N^6$-(Aminohexyl)-2'-deoxyisoGuanosine 5'-triphosphate 7:

The above-obtained compound was evaporated with methanol and dissolved in methanol (5 ml). Pd/C (10 weight %, 10 mg) and $HCOONH_4$ (63 mg) were added and it was stirred under reflux for 45 minutes. Then it was cooled to room temperature, filtered from the catalyst, the catalyst washed with hot water (60° C., 3 ml) and the combined filtrates concentrated in vacuum. The residue was dissolved in 28% aqueous ammonium hydroxide (3 ml), stirred at room temperature for 3 hours, concentrated in vacuum and purified by column chromatography on DEAE cellulose using a gradient of 0.05M-0.5M TEAB buffer. The product elutes at a buffer concentration of 0.3-0.4M. The fractions containing the product were evaporated and used further.

$N^6$-(6-Tamra-amidohexyl)-2'-deoxyisoGuanosine 5'-triphosphate 8a:

Compound 7 (approximately 1 mg as its triethylammonium salt) was dissolved in 0.2 ml 0.1M TEAB buffer and 6-carboxytetramethylrhodamine N-hydroxysuccinimide ester (10 mg), dissolved in DMF (0.2 ml), was added. It was stirred at 35° C. for 3 hours, then omega-aminobutyl agarose added to bind the excess Tamra™, stirred for another hour and the reaction mixture loaded to a DEAE cellulose column, which was eluted with a gradient of 0.05M-0.5M TEAB buffer. The product elutes at a buffer concentration of 0.4M. The fractions containing the product were evaporated at 30° C.

Compounds 8b and 8d will be prepared in the same way as compound 8a, using 6-carboxyfluoroscein N-hydroxysuccinimide ester and QSY7TM N-hydroxysuccinimide ester, respectively, instead of 6-carboxytetramethylrhodamine N-hydroxysuccinimide ester.

$N^6$-(6-Biotinylamidohexyl)-2'-deoxyisoGuanosine 5'-triphosphate 8c:

Compound 7 (approximately 1 mg as its triethylammonium salt) was dissolved in 0.2 ml water and biotin 2-nitrophenyl ester (10 mg), dissolved in DMF (0.2 ml), was added. The solution turned to light yellow. It was stirred at 35° C. for 1 hour, then omega-aminobutyl agarose added to bind the excess biotin, stirred for another hour and the reaction mixture loaded to a DEAE cellulose column, which was eluted with a gradient of 0.05M-0.5M TEAB buffer. The product elutes at a buffer concentration of 0.4M. The fractions containing the product were evaporated at 30° C.

Section B

For the following chemical reactions involving the synthesis of labeled -deoxyisoGuanosine 5'-Triphosphates using Process A, tributylammonium pyrophosphate was purchased from Sigma; biotin N-hydroxysuccinimide ester, was purchased from Pierce Chemical Company; QSY7™ N-hydroxysuccinimide ester and Dabcyl N-hydroxysuccinimide were purchased from Molecular Probes; all other chemicals were purchased from Aldrich Chemical Co. or Fisher Chemical Co. and were used without further purification. Solvents were dried over 4 Å molecular sieves. Reactions were carried out under dry argon in oven-dry glassware. Column chromatography was performed with silica gel (230-425 mesh).

The following abbreviations were used: $Ac_2O$ (Acetic anhydride); DMF (N,N-Dimethylformamide); DMAP (4,4'-Dimethylaminopyridine); DMT (4,4'-Dimethoxytrityl); $Et_3N$ (Triethylamine); MeCN (Acetonitrile); MeOH (Methyl alcohol); Tol (p-Toluyl).

1-(p,p'-Dimethoxytrityl)-hexamethylenediamine (9)

Hexamethylenediamine (10 eq., 375 mmol, 43.5 g) was coevaporated two times from pyridine and dissolved in 100 ml pyridine. DMAP (0.1 eq., 3.75 mmol, 457 mg) was added and the reaction flask placed in an ice bath. DMT-chloride (1 eq., 37.5 mmol, 12.69 g), dissolved in 100 ml pyridine, was added dropwise over 2 h. It was stirred at room temperature for 4 h, MeOH (5 ml) added, the reaction mixture concentrated and the remaining residue extracted with aqueous $NaHCO_3$/ethyl acetate. The organic layer was washed twice with aqueous $NaHCO_3$ solution, dried and the solvent evaporated. The obtained product was used in next step without further purification.

Yield: 14.895 g (35.634 mmol, 95%) sticky oil.

2-Chloro-6-(6-p,p'-dimethoxytritylaminohexyl)-aminopurine-2'-deoxy-3',5'-ditoluylriboside (10)

Compound 9 (1.3 equiv., 31.916 mmol, 13.34 g) was coevaporated with DMF and dissolved in 100 ml DMF. Diisopropylethylamine (3.9 equiv., 95.748 mmol, 16.65 ml) and compound 1 (1 equiv., 24.551 mmol, 13.282 g), dissolved in 100 ml DMF, were added and it was stirred at room temperature for 3 h. It was concentrated, the residue extracted with aqueous $NaHCO_3$/ethyl acetate, the organic layer dried and the solvent evaporated. The residue was triturated with ether twice and the obtained solid product used further after drying in vacuum without further purification.

2-Benzyloxy-6-(6-p,p'-dimethoxytritylaminohexyl)-aminopurine-2'-deoxyriboside (11)

Compound 10 (1 equiv., 19.23 mmol, 17.74 g) was dissolved in DMF (25 ml) and added to a solution of NaH (10 eq., 192.3 mmol, 7.69 g of a 60% dispersion in mineral oil) in benzylalcohol (128 mL). The reaction mixture was heated (120° C., 6 h) and then stirred at room temperature (15 h) before filtrated over Celite™, the filtrate evaporated, the residue extracted (ethyl acetate/water), the organic layer washed ($NaHCO_3$-solution), dried, the solvent evaporated and the residue triturated 5 times with ether/hexane 1:10. TLC: $CHCl_3$/10% MeOH $R_F$=0.26.

Yield: 10.280 g (13.562 mmol, 70.5% for 2 steps) foam.

2-Benzyloxy-6-(6-p,p'-dimethoxytritylaminohexyl)-aminopurine-2'-deoxy-5'-O-p,p'-dimethoxytritylriboside (12)

Compound 11 (14.7388 mmol, 11.172 g) was coevaporated with pyridine, dissolved in 150 ml pyridine and DMAP (0.25 equiv., 3.6847 mmol, 450 mg) added. The flask was placed in an ice bath and DMTCl (1.5 equiv., 22.108 mmol, 7.484 g) was added slowly over 2 h. It was stirred at room temperature for 22 h, then MeOH (1 ml) added, the reaction mixture concentrated and the residue extracted (chloroform/aqueous $NaHCO_3$). The organic layer was dried, the solvent evaporated and the residue triturated with ether/hexane 1:1 to remove the excess DMT and the insoluble solid product was dried and used further without additional purification.

Yield: 14.890 g (14.047 mmol, 95%) light brown foam.

2-Benzyloxy-6-(6-p,p'-dimethoxytritylaminohexyl)-aminopurine-3'-O-acetyl-2'-deoxy-5'-O-p,p'-dimethoxytritylriboside (13)

Compound 12 (14.047 mmol, 14.89 g) was coevaporated with pyridine, dissolved in 200 ml pyridine and DMAP (0.25 equiv., 3.5117 mmol, 428 mg), $Et_3N$ (5 equiv., 70.235 mmol, 9.7 ml) and $Ac_2O$ (2.5 equiv., 35.1175 mmol, 3.582 g) were added. It was stirred at room temperature for 4.5 h, then MeOH (2 ml) added, the reaction mixture concentrated and the residue extracted (ethyl acetate/aqueous $NaHCO_3$). The organic layer was dried, the solvent evaporated and the residue purified by column chromatography using an one step gradient of ethyl acetate/hexane/$Et_3N$ 30:60:1, then 65:35:3.

Yield: 5.93 g (5.385 mmol, 38%), yellow foam

2-Benzyloxy-6-(6-aminohexyl)-aminopurine-3'-O-acetyl-2'-deoxyriboside (14)

Compound 13 (2.471 mmol, 2.723 g) was dissolved in 50 ml acetonitrile/2 ml water and $Ce(NH_4)_2(NO_3)_3$ (0.3 equiv., 0.74 mmol, 406 mg) was added. It was refluxed for 45 min., then another 0.15 equiv. $Ce(NH_4)_2(NO_3)_3$ (0.37 mmol, 205 mg) added and refluxing continued for 1 h. Then, it was evaporated, the residue triturated with ether to remove the DMT, the insoluble product dried and used further without additional purification.

2-Benzyloxy-6-(6-trifluoroacetamidohexyl)-aminopurine-3'-O-acetyl-2'-deoxyriboside (15)

The above obtained compound 14 (max. 5.385 mmol) was dissolved in 30 ml MeOH/50 ml ethyl trifluoroacetate/5 ml $Et_3N$ and the reaction mixture stirred at room temperature for 21.5 h. TLC (chloroform/17.5% MeOH): $R_F$=0.72) indicated complete conversion. It was evaporated, the residue extracted (brine/ethyl acetate), the organic layer dried, the solvent evaporated and the residue purified by silica gel column chromatography using a one step gradient of chloroform/1.5% MeOH, then 17.5% MeOH. Yield: 2.80 g (4.714 mmol, 87%) foam.

2-Benzyloxy-6-(6-trifluoroacetamidohexyl)-aminopurine-3'-O-acetyl-5'-triphosphoryl-2'-deoxyriboside (16).

Imidazole (61 eq., 306 mg, 4.5 mmol, recrystallised) was dissolved in acetonitrile (3.6 mL) and chilled (0° C.). $POCl_3$ (19 eq., 0.128 mL) and triethylamine (61 eq., 0.633 mL) were then added and the mixture was stirred (0° C., 0.5 h) before adding a portion (0.309 mL) to 15 (1 eq., 0.074 mmol, 44 mg). This mixture was stirred (r.t., 0.5 h) before adding DMF (1.5 mL) containing tributylammonium pyrophosphate (2eq., 0.16 mmol, 73 mg). The reaction was then quenched (2 mL, 10% $NH_4COO$) 24 h later and lyophillized. Product was purified by anion-exchange chromatography (Dionex ProPac™ SAX-10; Dionex, Sunnyvale, Calif.) using 20% MeCN and a gradient of $(NH_4)_2CO_3$/20% MeCN. Collected product was repetitively lyophilized to remove excess salt. Yield 0.007 mmol (10%), white solid.

6-(6-aminohexyl)-aminopurine-5'-triphosphoryl-2'-deoxyriboside (7).

Compound 16 (0.007 mmol) was dissolved in methanol (2.5 mL) before adding Pd/C (10%, 5 mg) and $NH_4COO$ (0.05 mmol, 31 mg). The suspension was refluxed (1 h) before filtering off the catalyst and evaporating the solvent. The residue was then treated with 28% ammonium hydroxide (1.5 mL, 3 h, room temp.) before the reaction was dried and the product purified by anion-exchange chromatography (Dionex ProPac™ SAX-10; Dionex, Sunnyvale, Calif.) using 20% MeCN and a gradient of $(NH_4)_2CO_3$/20% MeCN. Collected product was repetitively lyophilized to remove excess salt. Yield 0.0063 mmol (90%), white solid.

6-(6-biotinylamidohexyl)-aminopurine-5'-triphosphoryl-2'-deoxyriboside (8c), 6-(6-dabcylamidohexyl)-aminopurine-5'-triphosphoryl-2'-deoxyriboside (17a), 6-(6-QSY7™ amidohexyl)-aminopurine-5'-triphosphoryl-2'-deoxyriboside (17b).

To 7 (0.88 µmol, triethylammonium salt) in $H_2O$ (40 µL) was added sodium borate (10.5 µL, 1M, pH 8.5) followed by DMF (216 mL) containing biotin N-hydroxysuccinimide ester, dabcyl N-hydroxysuccinimide ester, or QSY7™-N-hydroxysuccinimide ester (2.6 µmol, 3 eq.). The reaction proceeded (3 h, 55° C.) before it was diluted with 20% MeCN and the product purified by anion-exchange chromatography (Dionex ProPac™ SAX-10; Dionex, Sunnyvale, Calif.) using 20% MeCN and a gradient of $(NH_4)_2CO_3$/20% MeCN. Yields 50-80%.

Example 8

"Real time" Monitoring of PCR Amplification by Site Specific Incorporation of a Fluorescence-quenching Nonstandard Deoxy-nucleotide Triphosphate Monitoring of the flourescence of PCR reactions was performed during the cycling of the PCR reactions. PCR reactions included a first and second primer and the second primer contains a fluorophore-coupled nucleotide (FAM-dT) at its 5' end. During amplification of the template nucleic acid, a standard nucleoside triphosphate (reaction A; dTTP) or an isoG nucleoside triphosphate (reaction B; dGisoTP) coupled to a fluorescence quenching compound (Dabcyl or QSY7™) is incorporated [opposite and adjacent] the fluorophore-coupled nucleotide (FAM-dT) of the second primer, reducing the fluorescence signal in the PCR reaction. The following nucleic acids were used in PCR reactions for this example:

| Nucleic Acid Component | Sequence | SEQ ID NO: |
|---|---|---|
| First Primer | 5'-GTYATYTGCG-c3-TCGTGCGGTGCGTC-3' | SEQ ID NO: 18 |
| Second Primer A | 3'-TGTGTCGTGTCGTCCGAT-FAM 5' | SEQ ID NO: 19 |
| Second Primer B | 3'-TGTGTCGTGTCGTCCGXT-FAM 5' | SEQ ID NO: 20 |
| Template | 5'-TCGTGCGGTGCGTCACACAGCACAGCAGGC-3' | SEQ ID NO: 21 |

"c3" indicates a propyl spacer which was chemically installed in place of a nucleotide during synthesis of the first primer. The phosphoramidite used in the synthesis of the first primer was 3-O-Dimethyltrityl-propyl-1-[2-cyanoethyl)-(N, N-diisopropyl)]-phosphoramidite (Spacer Phosphoramidite C3; Glen Research, Sterling, Va.). Optionally, an oligonucleotide containing an identical nucleotide sequence, including nucleotide modifications, but lacking the propyl spacer can be used as a substitute for the first primer in the PCR reaction.

The following components (base PCR reaction components) at the indicated concentrations were present in all PCR reactions:

| Component | 1X Conc. | Supplier and location |
|---|---|---|
| Bis-Tris-Propane pH 8.9 | 10 mM | Sigma, St. Louis, MO |
| Bovine Serum Albumin | 0.1 µg/µl | Sigma, St. Louis, MO |
| Tween ™ 20 | 0.1% | EM Sciences, Gibbstown, NJ |
| d-Trehalose | 37.5 mM | Aldrich, Milwaukee, WI |
| Potassium acetate | 40 mM | Sigma, St. Louis, MO |
| $MgCl_2$ | 3 mM | Sigma, St. Louis, MO |
| Klen-Taq ™ DNA polymerase | 0.1 units/µL | AbPeptides, St. Louis, MO |
| dATP | 50 µM | Promega, Madison, WI |
| dGTP | 50 µM | Promega, Madison, WI |
| dCTP | 50 µM | Promega, Madison, WI |
| First Primer | 0.2 µM | |
| Template | 0.4 pM | |

The components indicated above were prepared

Second primer A, second primer B, dTTP, Dabcyl dTTP (Glen Research, Sterling, Va.), Dabcyl dGisoTP, and QSY7™ dGisoTP were variable components in the following PCR reactions. These components were added to PCR reactions A through J, as indicated below, at the indicated concentrations:

| PCR Reaction: | Variable PCR components (in addition to base components): |
|---|---|
| A | 0.2 µM Second Primer B, and 50 µM dTTP |
| B | 0.2 µM Second Primer A, and 1 µM Dabcyl dTTP |
| C | 0.2 µM Second Primer B, and 1 µM Dabcyl dGisoTP |
| D | 0.2 µM Second Primer B, and 50 µM dTTP |

-continued

| PCR Reaction: | Variable PCR components (in addition to base components): |
|---|---|
| E | 0.2 μM Second Primer B, and 5 μM Dabcyl dTTP |
| F | 0.2 μM Second Primer B, 50 μM dTTP, and 5 μM Dabcyl dGisoTP |
| G | 0.2 μM Second Primer B, 50 μM dTTP, and 5 μM QSY7 ™ dGisoTP |
| H | 0.2 μM Second Primer A, and 50 μM dTTP |
| I | 0.2 μM Second Primer A, and 5 μM Dabcyl dTTP |
| J | 0.2 μM Second Primer A, 50 μM dTTP, and 5 μM QSY7 ™ dGisoTP |

Reactions were prepared for a 25 μL final volume. Reactions mixtures were loaded in 25 μL Smart Cycler PCR tubes (Cepheid, Sunnyvale, Calif.). The PCR tubes were spun in a mini-centrifuge for 6 seconds to pull liquid into the reaction chamber. Tubes containing PCR reactions were then placed in a Smart Cycler™ (Cepheid, Sunnyvale, Calif.) to provide constant monitoring of fluorescence during the entire PCR reaction.

Thermal cycling parameters:

| Cycle # | Step | Temp | Time |
|---|---|---|---|
| 1 | 1 | 95° C. | 5 min. |
| 2-41 | 1 | 95° C. | 1 sec. |
| | 2 | 58° C. | 1 sec. |
| | 3* | 72° C. | 10 sec. |

*During Step 3 of cycles 2-41 the optics of the Smart Cycler ™ were activated, allowing determination of the fluorescence in the PCR reaction tube.

Following the 41 cycles of PCR amplification, PCR reaction products were subject to a melt curve analysis by increasing the temperature in the PCR tubes from 60° C. to 95° C. at a rate of 0.2° C. per second with flourescence monitoring optics on.

Figure 17A:
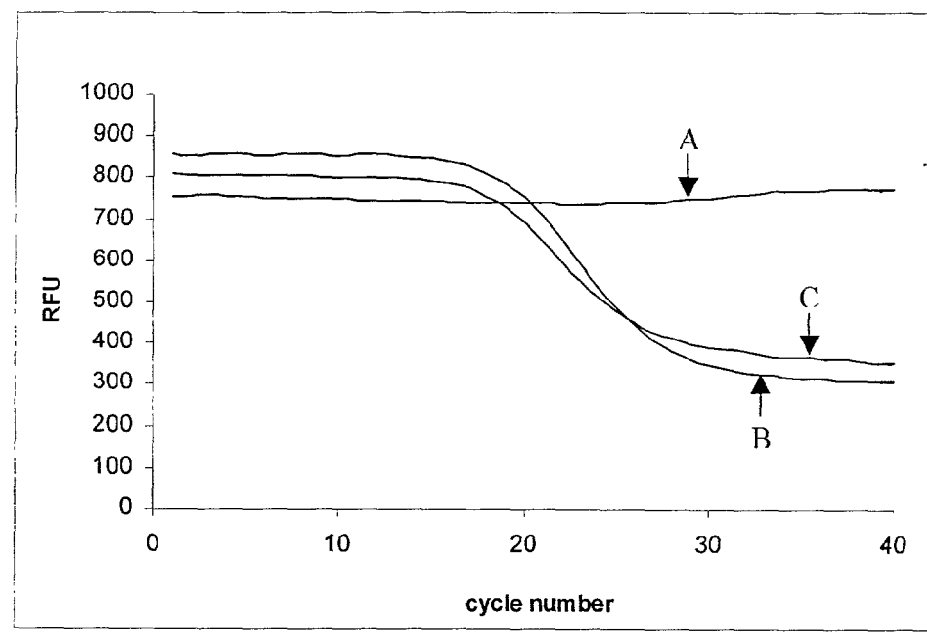
FIG. 17A is a graph demonstrating the "real time" monitoring of quenching of fluorescence in a PCR reaction by site specific incorporation of a quenching compound into a PCR amplification product; relative fluorescence units (RFU's) are indicated on the Y axis and the number of PCR cycles are indicated on the X axis.
Figure 17B:
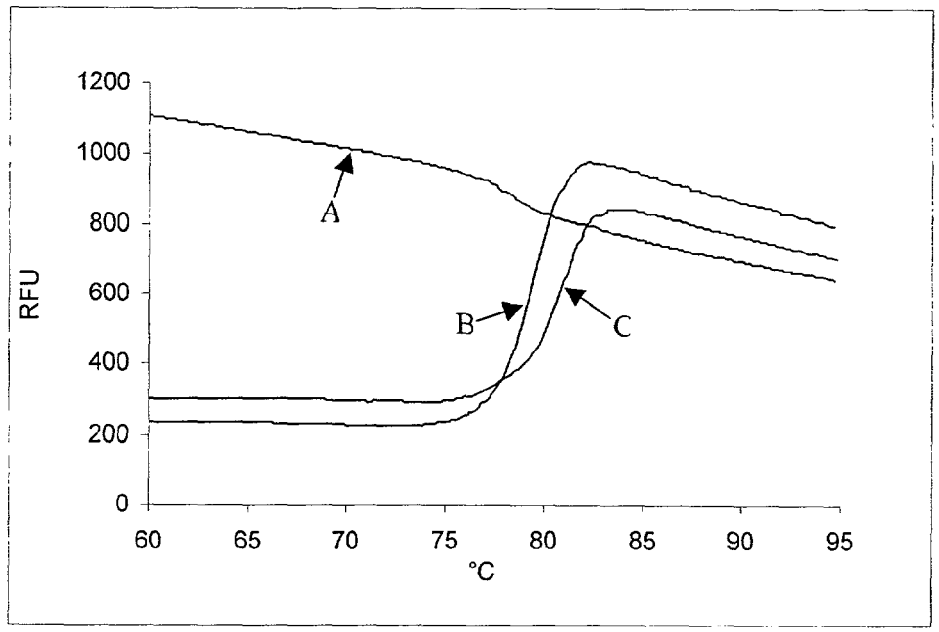
FIG. 17B is a graph demonstrating a melting curve analysis of the PCR products of FIG. 17A; the melting temperature is indicated on the X axis.

Fluorescence quenching of PCR reaction products from PCR reactions A, B, and C is shown in FIG. 17A and the melting curve analysis of these PCR products is shown in FIG. 17A. These results demonstrate that the fluorescence of the PCR reaction is quenched in samples that include a quenching compound-coupled standard nucleoside triphosphate or a quenching compound-coupled isoG nucleoside triphosphate in combination with the a fluorophore-coupled standard nucleoside-containing second primer or nonstandard nucleoside-containing second primer, respectively. The melting curve data indicates that the fluorescence in the reaction products is restored by separating the flurophore-coupled nucleic acid strands from the quenching compound-coupled nucleic strands.

Figure 18A:
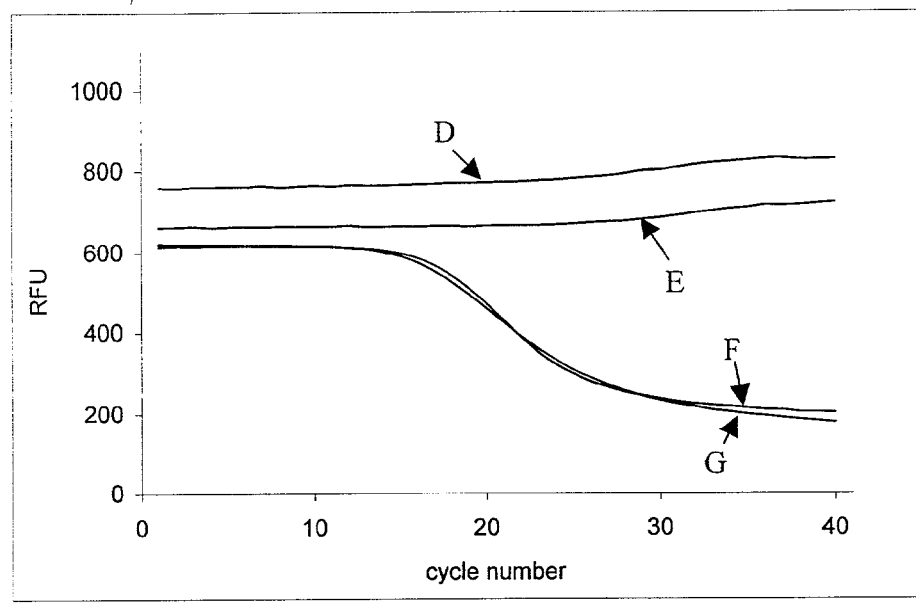
FIG. 18A is a graph demonstrating the "real time" monitoring of quenching of fluorescence in a PCR reaction by site specific incorporation of a quenching compound into a PCR amplification product; relative fluorescence units (RFU's) are indicated on the Y axis and the number of PCR cycles are indicated on the X axis.
Figure 18B:
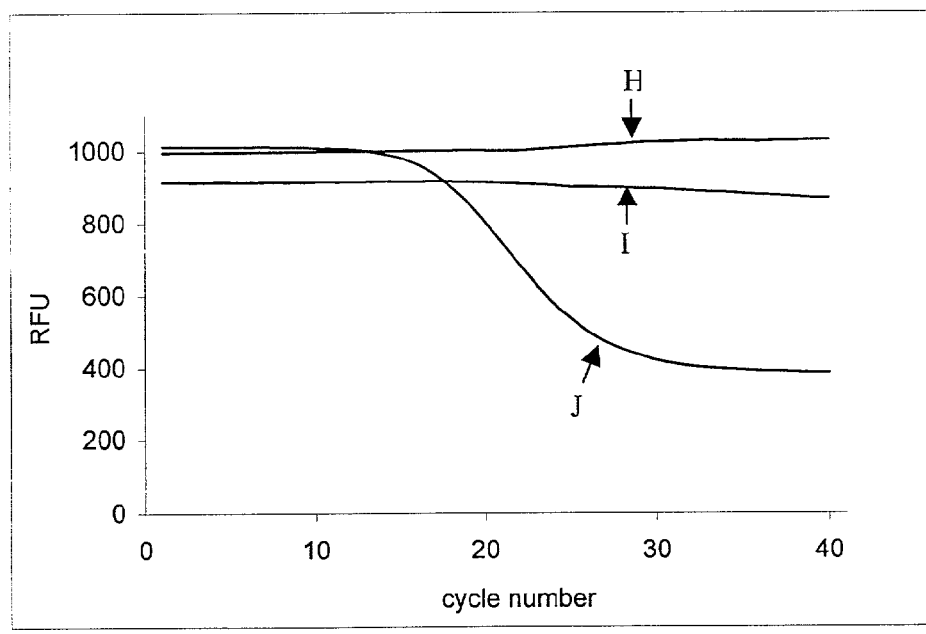
FIG. 18B is a graph demonstrating a melting curve analysis of the PCR products of FIG. 17A; the melting temperature is indicated on the X axis.

Fluorescence quenching of PCR reaction products from PCR reactions D, E, F, and G is shown in FIG. 18A Fluorescence quenching of PCR reaction products from PCR reactions H, I, and J is shown in FIG. 18B.

Example 9

Real Time Quantitation of Genomic DNA

Monitoring of the fluourescence of PCR reactions was performed during the cycling of the PCR reactions and amplification of nucleic acid template from a genomic DNA sample. PCR reactions included a first primer and second primer containing two non-standard nucleotides (iso-G and iso-C); the primers were designed to hybridize and to amplify a region of mouse genomic DNA. PCR reactions also included a reporter nucleic acid containing a non-standard nucleotide (iso-G), a fluorescence quenching compound-coupled nucleotide (Dabcyl dT), and a fluorophore (6FAM) coupled to the 5' base (T) of the reporter. Annealing of the reporter nucleic acid to the amplification product, including pairing of the non-standard nucleotides, can cause the cleavage of the fluorophore from the reporter nucleic acid containing the fluorescence quenching compound-coupled nucleotide by nucleic acid polymerase activity.

The following nucleic acids were used in PCR reactions for this example:

| Nucleic acid component | Sequence | Seq ID NO: |
|---|---|---|
| Reporter | 5'-FAM-TYQCCTGTCTGCCTGT-3' | SEQ ID NO: 22 |
| First Primer A | 5'-GATAATCAGTAGCTTTGTAACCCTG-3' | SEQ ID NO: 23 |
| First Primer B | 5'-GTGGCACAAGATTGATGGAAT-3' | SEQ ID NO: 24 |
| Second Primer A | 3'-CATGTCATTTGTCAACCACCCYXAGGA-CAGACGGACAGCAC-5' | SEQ ID NO: 25 |
| Second primer B | 3'-CAATGACGTCGTTCCAGGAYXAGGAC-AGACGGACA-5' | SEQ ID NO: 26 |
| Template A | Mouse genomic DNA; Strain: A/J (target locus L11316, Chromosome 3-9.679 P) | |
| Template B | Mouse genomic DNA; Strain: C57BL/6J (target locus R75378, Chromosome 10-41.5 F) | |

Mouse genomic DNA was obtained from Jackson Laboratories (Bar Harbor, Me.) and diluted in 1 mM MOPS pH7.5, 0.01 mM EDTA. For template A, Mouse strain A/J genomic DNA was serially diluted to concentrations of 5 ng/μl, 2.5 ng/μl, 1.25 ng/μl, 0.63 ng/μl, 0.31 ng/μl, and 0.16 ng/μl. For template B, the Mouse strain C57BL/6J genomic DNA was serially diluted to concentrations of 20 ng/μl, 2 ng/μl, 0.2 ng/μl, 20 pg/μl, 2 pg/μl, and 0.2 pg/μl. The genomic DNA dilution series were boiled for 5 min., placed on ice for 5 min., and stored at −20° C.

Primers were synthesized for the PCR amplification and detection of specific target nucleic acid sequences in the mouse genome. An initial target nucleic acid sequence was chosen to assess the viability of this procedure using A/J mouse genomic DNA, locus L11316, Chromosome 3-9.679 P (design A). The target sequence chosen for further genomic DNA quantitation was mouse strain C57BL/6J, locus R75378, Chromosome 10-41.5 F (design B). First primer A and first primer B are designed to have a Tm between 60.0-63.0° C. Second primer A and second primer B are designed to have a Tm between 61.0-63.0° C. All primers were assessed for secondary structure formation using Oligo 4.0 Software for Macintosh (National Biosciences, Minneapolis, Minn.).

The following components (base PCR reaction components) at the indicated concentrations were present in all PCR reactions in this example:

| Component | 1X Conc. | Supplier and location |
|---|---|---|
| Bis-Tris-Propane pH 8.9 | 10 mM | Sigma, St. Louis, MO |
| Bovine Serum Albumin | 0.1 µg/µL | Sigma, St. Louis, MO |
| Tween ™ 20 | 0.1% | EM Sciences, Gibbstown, NJ |
| d-Trehalose | 37.5 mM | Aldrich, Milwaukee, WI |
| Potassium acetate | 40 mM | Sigma, St. Louis, MO |
| $MgCl_2$ | 2 mM | Sigma, St. Louis, MO |
| Amplitaq ™ DNA polymerase | 0.025 units/µL | Applied Biosystems, Foster City, CA |
| dATP | 25 µM | Promega, Madison, WI |
| dGTP | 25 µM | Promega, Madison, WI |
| dCTP | 25 µM | Promega, Madison, WI |
| dTTP | 25 µM | Promega, Madison, WI |
| First Primer (A or B) | 0.2 µM | |
| Second Primer (A or B) | 0.2 µM | |
| Reporter | 0.2 µM | |

Master mix A containing the ingredients listed above (with First Primer A and Second Primer A) was prepared at a 1.04× concentration for 25 µL final reaction volumes.

Master Mix B containing the ingredients listed above (with First Primer B and Second Primer B) was prepared at a 1.25× concentration for 25 µL final reaction volumes.

Design A reaction mixtures were created by adding 1 µL of each A/J genomic target DNA dilutions of 5 ng/µL, 2.5 ng/µL, 1.25 ng/µL, 0.63 ng/µL, 0.31 ng/µL, and 0.16 ng/µL to 25 µL Smart Cycler™ PCR tubes containing 24 µL of PCR A Master mix. Tubes were spun in a mini-centrifuge for 6 seconds to pull liquid into the reaction chamber. Individual PCR tubes contained 5 ng, 2.5 ng, 1.25 ng, 630 pg, 30 pg, and 160 pg of A/J genomic target DNA which corresponds to a nucleic acid target number of 1500, 750, 375, 188, 94, and 47 haploid equivalents, respectively.

Design B reaction mixtures were created by adding 5 µL of each C57BL/6J genomic target DNA dilutions of 20 ng/µL, 2 ng/µL, 0.2 ng/µL, 20 pg/µL, and 2 pg/µL to a thermocycling plate well or tube specific for each real time thermocycler containing 20 µL of PCR Master Mix B. Individual PCR tubes or wells contained 100 ng, 10 ng, 1 ng, 100 pg, and 10 pg of C57BL/6J genomic target DNA which corresponds to a nucleic acid target number of 30,000 targets, 3,000 targets, 300 targets, 30 targets, and 3 targets, respectively. When reactions were run in microtiter plates, a 15 µL mineral oil overlay was added to each well prior to thermocycling in order to prevent evaporation of the sample volume.

Design A reaction mixtures were placed into the Smart Cycler™ and cycled under the following conditions:

| Cycle # | Step | Temp | Time |
|---|---|---|---|
| 1 | 1 | 90° C. | 30 min. |
| 2-16 | 1 | 90° C. | 1 sec. |
| | 2 | 56° C. | 1 sec. |
| 17-51 | 1 | 90° C. | 1 sec. |
| | 2* | 56° C. | 11 sec. |

*During Step 2 of cycle #17-51 the optics of the Smart Cycler ™ were activated, allowing determination of the fluorescence in the PCR reaction tube in order to generate a kinetic plot.

Figure 19:
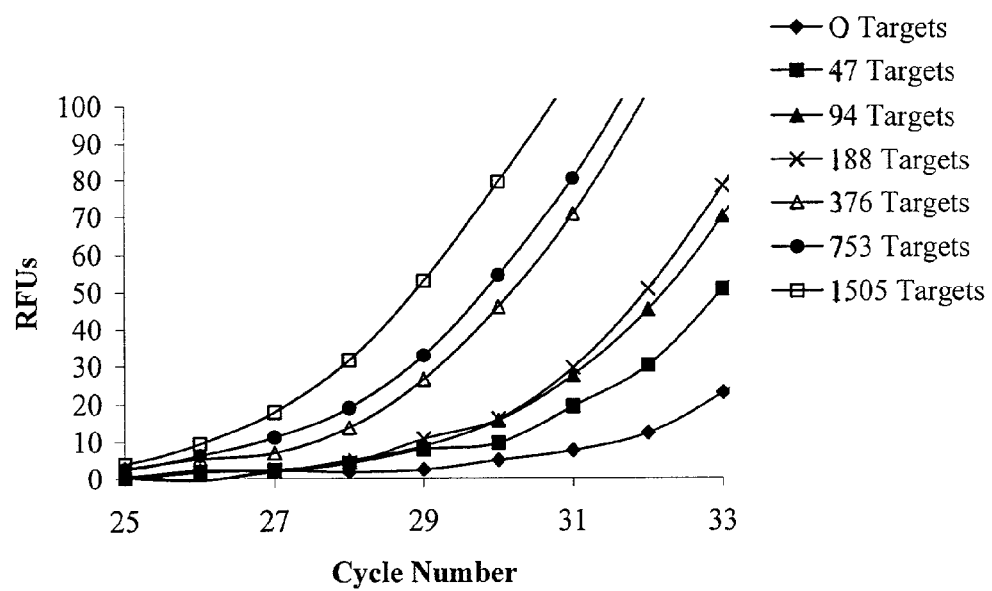
FIG. 19 is a graph demonstrating the "real time" monitoring of an increase in the fluorescence in a PCR reaction amplifying genomic DNA; relative fluorescence units (RFU's) are indicated on the Y axis and the number of PCR cycles are indicated on the X axis.

The fluorescence reading for these reactions are shown in FIG. 19.

Design B reaction mixtures were individually placed into the following real-time PCR thermocyclers:
1) Smart Cycler™ (Cepheid; Sunnyvale, Calif.) using Smart Cycler™ 25 µL Tubes (Cepheid; Sunnyvale, Calif.)
2) Light Cycler™ (Roche; Basel, Switzerland) using Light Cycler™ Tubes (Roche; Basel, Switzerland)
3) iCycler™ (BioRad; Hercules, Calif.) using 96-well Microtiter Plates (MJ Research Inc.; Waltham, Mass.)
4) 7700 (Applied Biosystems; Foster City, Calif.) using MicroAmp™ Optical 96-Well Reaction plate wells (Applied Biosystems; Foster City, Calif.)

and cycled under the following conditions:

| Cycle # | Step | Temp | Time |
|---|---|---|---|
| 1 | 1 | 95° C. | 5 min. |
| 2-46 | 1 | 95° C. | 5 sec. |
| | 2 | 56° C. | 10 sec. |
| | 3* | 60° C. | 10 sec. |

*During Step 3 of cycle #2-46 the optics of the real-time PCR thermocyclers were activated to read FAM-generated fluorescence, allowing determination of the fluorescence in the PCR reaction tube in order to generate a kinetic plot.

Fluorescence readouts were analyzed by the threshold cycle (Ct) and correlation of variance (Cv) method. The threshold cycle is when the system begins to detect the increase in the signal associated with an exponential growth of PCR product during the log-linear phase. The slope of the log-linear phase is a reflection of the amplification efficiency and bona fide amplification is indicated by an inflection point in the slope, the point on the growth curve when the log-linear phase begins. This point also represents the greatest rate of change along the growth curve. Nucleic acid quantitation is correlated with the Ct wherein the greater the initial amount of nucleic acid, the lower the Ct value. Ct should be placed above any baseline activity and within the exponential increase phase.

Example 10

Real Time Quantitation of RNA

Monitoring of the fluorescence of PCR reactions was performed during the cycling of the PCR reactions and amplification of nucleic acid template from a RNA sample. DNA primers were synthesized for the detection and quantitation of human β-actin mRNA. The cDNA/first primer hybridizes to a sequence on the 5' region of human β-actin mRNA and primes cDNA synthesis using reverse transcriptase. The cDNA/First primer and the Second Primer, which contains two non-standard nucleotides (iso-C and iso-G), are then used for amplification of the human β-actin sequence using the cDNA as a template. PCR reactions also included a reporter nucleic acid containing a non-standard nucleotide (iso-G), a fluorescence quenching compound-coupled nucleotide (Dabcyl dT), and a fluorophore (6FAM) coupled to the 5' base (T) of the reporter. Annealing of the reporter nucleic acid to the amplification product, including pairing of the non-standard nucleotides, can cause the cleavage of the fluorophore from the reporter nucleic acid coupled to the fluorescence quenching compound by nucleic acid polymerase activity.

The following nucleic acids were used in reverse transcription-PCR (RT-PCR) reactions for this example:

| Nucleic acid component | Sequence | SEQ ID NO: |
|---|---|---|
| Reporter | 3'-TGTCCGTCTGTCCQYT-FAM-5' | SEQ ID NO: 27 |
| cDNA/First Primer | 3'-CTACTATAGCGGCGCG-5' | SEQ ID NO: 28 |
| Second Primer | 5'-CACGACAGGCAGACAGGAXYCGCCAG-CTCACCATG-3' | SEQ ID NO: 29 |
| Template | human cardiac RNA (single donor) | |

Total human cardiac RNA from a single donor was obtained from Clontech (Palo Alto, Calif.). RNA samples were diluted to 20 ng/μl, 2 ng/μl, 200 pg/μl, 20 pg/μl, 2 pg/μl and 0.2 pg/μl in a buffer composed of 5 mM Bis-Tris-Propane pH 8.9, 0.1 mM ETDA, 100 ng/ml yeast tRNA (Sigma, St. Louis, Mo.) and 100 ng/ml sheared herring sperm DNA (Sigma, St. Louis, Mo.).

The following components (base PCR reaction components) at the indicated concentrations were present in all PCR reactions:

| Component | 1X Conc. | Supplier and location |
|---|---|---|
| Bis-Tris-Propane pH 8.9 | 10 mM | Sigma, St. Louis, MO |
| Bovine Serum Albumin | 0.1 μg/μL | Sigma, St. Louis, MO |
| Tween ™ 20 | 0.1% | EM Sciences, Gibbstown, NJ |
| d-Trehalose | 37.5 mM | Aldrich, Milwaukee, WI |
| Potassium acetate | 40 mM | Sigma, St. Louis, MO |
| MgCl$_2$ | 3 mM | Sigma, St. Louis, MO |
| Ampli-taq ™ DNA polymerase | 0.05 U/μL | Applied Biosystems, Foster City, CA |
| Reverse Transcriptase (AMV) | 0.05 U/μL | Promega, Madison, WI |
| dATP | 50 μM | Promega, Madison, WI |
| dGTP | 50 μM | Promega, Madison, WI |
| dCTP | 50 μM | Promega, Madison, WI |
| dTTP | 50 μM | Promega, Madison, WI |
| cDNA/First Primer | 0.2 μM | |
| Second Primer | 0.2 μM | |
| Reporter | 0.2 μM | |

An RT-PCR Master mix containing the reagents listed in Table X was prepared at a 1.25× concentration for a 25 μL final reaction volume using nuclease-free H$_2$O. RT-PCR reactions mixtures were prepared by adding 20 μL of 1.25× RT-PCR Master mix to 5 μL of each diluted RNA sample in 25 μl Smart Cycler™ PCR tubes. Tubes were then spun in a minicentrifuge for 6 seconds to pull liquid into the reaction chamber.

Following centrifugation, reaction mixtures were placed immediately into the Smart Cycler™ and cycled under the following conditions:

| Cycle # | Step | Temp | Time |
|---|---|---|---|
| 1. | 1 | 60° C. | 1 min. |
| 2. | 1 | 95° C. | 5 min. |
| 3-52 | 1 | 94° C. | 1 sec. |
| | 2* | 60° C. | 10 sec. |

Figure 20:
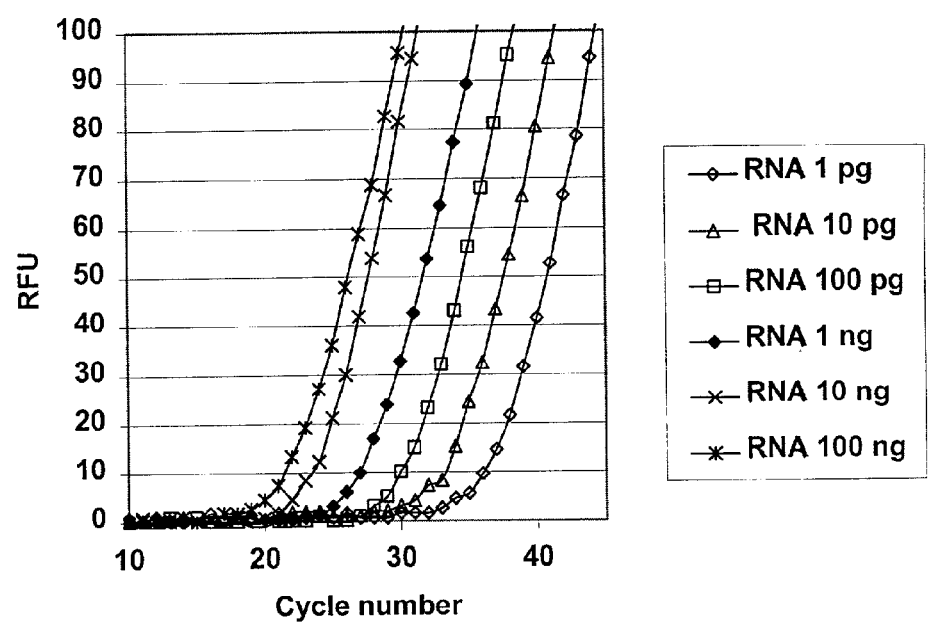
FIG. 20 is a graph demonstrating the "real time" monitoring of an increase in the fluorescence in PCR reaction amplifying different amounts of reverse-transcribed RNA; relative fluorescence units (RFU's) are indicated on the Y axis and the number of PCR cycles are indicated on the X axis.

*During Step 2 of cycle #3-52 the optics of the real-time PCR thermocyclers were activated to read FAM-generated fluorescence, allowing determination of the fluorescence in the PCR reaction tube in order to generate a kinetic plot. The results are shown in FIG. 20.

Example 11

Real Time Quantitation of RNA by Site Specific Incorporation of Labeled Non-standard Bases Monitoring of the fluourescence of PCR reactions was performed during the cycling of the PCR reactions and amplification of nucleic acid template from a RNA sample. DNA primers were synthesized for the detection and quantitation of human β-actin mRNA. The cDNA/first primer hybridized to a sequence on the 5' region of human β-actin mRNA and primed cDNA synthesis using reverse transcriptase. The cDNA/First primer and a second primer containing a fluorophore (6FAM) coupled to the 5' base (T) of the reporter and a 5'-penultimate non-standard nucleotide (iso-dC) were then used for amplification of the human β-actin sequence using the cDNA as a template. During amplification of the template nucleic acid, a fluorescence quenching compound-coupled nonstandard nucleoside triphosphate (Dabcyl-d-isoGTP) was present in the PCR reaction and incorporated opposite the nonstandard nucleotide (iso-dC) of the second primer, which is adjacent the fluorophore-coupled 5'-nucleotide (FAM-dT), and reduces the fluorescence signal in the PCR reaction.

The following nucleic acids were used in RT-PCR reactions for this example:

| Nucleic acid component | Sequence | SEQ ID NO: |
|---|---|---|
| cDNA/First Primer | 3'-CTACTATAGCGGCGCG-5' | SEQ ID NO: 28 |
| Second Primer | 5'FAM-TXCGCCAGCTCACCATG-3' | SEQ ID NO: 30 |
| Template | human cardiac RNA (single donor) | |

Total human cardiac RNA from a single donor was obtained from Clontech (Palo Alto, Calif.) RNA samples were diluted to 20 ng/μL, 2 ng/μL, 200 pg/μL, 20 pg/μL, 2 pg/μL and 0.2 pg/μL in a buffer composed of 5 mM Bis-Tris-Propane pH 8.9, 0.1 mM ETDA, 100 ng/mL yeast tRNA (Sigma, St. Louis, Mo.) and 100 ng/mL sheared herring sperm DNA.

The following components (base PCR reaction components) at the indicated concentrations were present in all PCR reactions:

| Component | 1X Conc. | Supplier and location |
|---|---|---|
| Bis-Tris-Propane pH 8.9 | 10 mM | Sigma, St. Louis, MO |
| Bovine Serum Albumin | 0.1 ug/μL | Sigma, St. Louis, MO |
| Tween ™ 20 | 0.1% | EM Sciences, Gibbstown, NJ |
| d-Trehalose | 37.5 mM | Aldrich, Milwaukee, WI |
| Potassium acetate | 40 mM | Sigma, St. Louis, MO |
| $MgCl_2$ | 3 mM | Sigma, St. Louis, MO |
| Klen-Taq ™ DNA polymerase | 0.025 U/μL | AbPeptides, St. Louis, MO |
| Reverse Transcriptase Maloney-Murine Lukemia Virus (M-MLV-RT) | 0.5 U/μL | Ambion, Austin, TX |
| dATP | 50 μM | Promega, Madison, WI |
| dGTP | 50 μM | Promega, Madison, WI |
| dCTP | 50 μM | Promega, Madison, WI |
| dTTP | 50 μM | Promega, Madison, WI |
| Dabcyl-d-isoGTP | 2 μM | Eragen Biosciences, Madison, WI |
| cDNA/First Primer | 0.2 μM | |
| Second Primer | 0.2 μM | |

An RT-PCR Master mix was prepared for a 25 μL final reaction volume at a 1.25× concentration using nuclease-free $H_2O$. RT-PCR reactions mixtures were prepared by adding 20 μl of 1.25× RT-PCR Master mix to 5 μL of each diluted RNA sample in 25 μL Smart Cycler™ 25 μl Tubes (Cepheid, Sunnyvale, Calif.). Tubes were then spun in a mini-centrifuge for 6 seconds to pull liquid into the reaction chamber.

Following centrifugation, reaction mixtures were placed immediately into a Smart Cycler™ (Cepheid, Sunnyvale, Calif.), and cycled under the following conditions:

| Cycle # | Step | Temp | Time |
|---|---|---|---|
| 1. | 1 | 60° C. | 1 min. |
| 2. | 1 | 95° C. | 5 min. |
| 3-22 | 1 | 94° C. | 1 sec. |
| | 2 | 60° C. | 1 sec. |
| 23-52 | 1 | 94° C. | 1 sec. |
| | 2 | 60° C. | 1 sec. |
| | 3* | 72° C. | 6 sec. |

Figure 21:
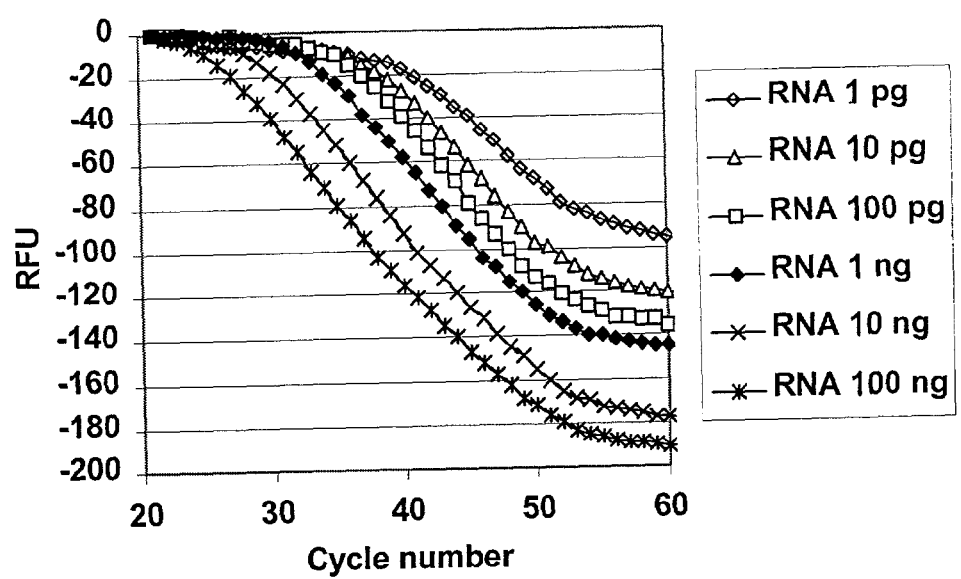
FIG. 21 is a graph demonstrating the "real time" monitoring of quenching of fluorescence in a PCR reaction amplifying different amounts of reverse-transcribed RNA by site specific incorporation of a quenching compound into PCR amplification products; relative fluorescence units (RFU's) are indicated on the Y axis and the number of PCR cycles are indicated on the X axis.

*During Step 3 of cycle #23-52 the optics of the Smart Cycler ™ are activated to read FAM-generated fluorescence, allowing determination of the fluorescence in the PCR reaction tube in order to generate a kinetic plot as shown in FIG. 21.

Example 12

Multiplexed Allele Specific PCR

Multiplexed fluorescence-based PCR reactions were performed to determine the sequence of a single nucleotide polymorphism mouse STS sequence 27.MMHAP25FLA6 from various mouse strains. In this example, the multiplexed PCR reaction included a common first primer that hybridizes to a downstream non-polymorphic sequence on the target nucleic acid and two upstream second primers, second primer A and second primer B, each second primer being allele-specific where the specificity was determined by different 3' nucleotides. Second primer A and second primer B also had different 5' regions, which did not contribute to target nucleic acid hybridization but allow for hybridization of reporter A and reporter B, respectively. The reporter nucleic acids each contained a 5'-penultimate non-standard nucleotide and a fluorescence quenching compound-coupled nucleotide and each contained 5' nucleotides with different fluorophores (either FAM or HEX) coupled to the 5' nucleotide. The different fluorophores emitted different wavelengths of light upon excitation. Annealing of the reporter nucleic acid to the amplification product, including pairing of the non-standard nucleotides, can cause the cleavage of the fluorophore or fluorophores from the quenching compound-coupled reporter nucleic acid by nucleic acid polymerase activity. The predominance of an allele-specific nucleic acid target results in particular fluorescence emission of the fluorophore from the cleaved reporter.

The following nucleic acids were used in RT-PCR reactions for this example:

| Nucleic acid component | Sequence | SEQ ID NO: |
|---|---|---|
| Reporter A | 5'-HEX-TYQGGACAGACG-3' | SEQ ID NO: 31 |
| Reporter B | 5'-FAM-TYQCCTGTCTGC-3' | SEQ ID NO: 1 |
| First Primer | 3'-CAGTGACTGGCTGACGAG-5' | SEQ ID NO: 32 |
| Second Primer A | 5'-<u>CGTCTGTCCAXY</u>GAGCTAGCGGAGGCC-3' | SEQ ID NO: 33 |

-continued

| Nucleic acid component | Sequence | SEQ ID NO: |
|---|---|---|
| Second primer B | 5'-<u>GCAGACAGGAXY</u>GGAGCTAGCGGAGGCT-3' | SEQ ID NO: 34 |
| Template 1 | Mouse genomic DNA; Strain: A/J± (target: 27.MMHAP25FLA6.seq located on mouse chromosome 2: seq. variation: 'CC') | |
| Template 2 | Mouse genomic DNA; Strain: AKR/J± (target: 27.MMHAP25FLA6.seq located on mouse chromosome 2: seq. variation: 'TT') | |
| Template 3 | Mouse genomic DNA; Strain: BALB/cByJ± (target: 27.MMHAP25FLA6.seq located on mouse chromosome 2: seq. variation: 'CC') | |
| Template 4 | Mouse genomic DNA; Strain: C3H/HeJ± (target: 27.MMHAP25FLA6.seq located on mouse chromosome 2: seq. variation: 'CC') | |
| Template 5 | Mouse genomic DNA; Strain: C57BL/6J± (target: 27.MMHAP25FLA6.seq located on mouse chromosome 2: seq. variation: 'TT') | |
| Template 6 | Mouse genomic DNA; Strain: DBA/2J± (target: 27.MMHAP25FLA6.seq located on mouse chromosome 2: seq. variation: 'CC') | |
| Template 7 | Mouse genomic DNA; Strain: AB6F1** (target: 27.MMHAP25FLA6.seq located on mouse chromosome 2: seq. variation: 'CT') | |
| Template 8 | Mouse genomic DNA; Strain: AKD2F1** (target: 27.MMHAP25FLA6.seq located on mouse chromosome 2: seq. variation: 'CT') | |
| Template 9 | Mouse genomic DNA; Strain: B6C3F1** (target: 27.MMHAP25FLA6.seq located on mouse chromosome 2: seq. variation: 'CT') | |
| Template 10 | Mouse genomic DNA; Strain: B6D2F1** (target: 27.MMHAP25FLA6.seq located on mouse chromosome 2: seq. variation: 'CT') | |
| Template 11 | Mouse genomic DNA; Strain: CByB6F1** (target: 27.MMHAP25FLA6.seq located on mouse chromosome 2: seq. variation: 'CT') | |
| Template 12 | Mouse genomic DNA; Strain: C3D2F1** (target: 27.MMHAP25FLA6.seq located on mouse chromosome 2: seq. variation: 'CC') | |
| Template 13 | Mouse genomic DNA; Strain: CByD2F1** (target: 27.MMHAP25FLA6.seq located on mouse chromosome 2: seq. variation: 'CC') | |

±= inbred strains.
**= F1 hybrid strains.

Mouse gDNA samples were purchased from Jackson Laboratories (Bar Harbor, Me.). All gDNA samples were diluted to 2 ng/µL in 1 mM MOPS pH 7.5, 0.01 mM EDTA.

| Component | 1X Conc. | Supplier and location |
|---|---|---|
| Bis-Tris-Propane pH 8.9 | 10 mM | Sigma, St. Louis, MO |
| Potassium acetate | 40 mM | Sigma, St. Louis, MO |
| MgCl$_2$ | 2 mM | Sigma, St. Louis, MO |
| AmpliTaq ™ DNA polymerase | 0.5 U/rxn | Applied Biosystems, Foster City, CA |
| dATP | 50 µM | Promega, Madison, WI |
| dGTP | 50 µM | Promega, Madison, WI |
| dCTP | 50 µM | Promega, Madison, WI |
| dTTP | 50 µM | Promega, Madison, WI |
| First Primer | 0.2 µM | |
| Second Primer A | 0.2 µM | |
| Second Primer B | 0.15 µM | |
| Reporter A | 0.2 µM | |
| Reporter B | 0.2 µM | |

A Master Mix containing components listed above was prepared at a 2× concentration for a final reaction volume of 10 µL. 5 µl of the Master Mix was aliquoted to individual wells of an assay plate and 5 µL of target DNAs (10 ng) were added to individual wells. PCR reactions were prepared for positive controls (perfect match template) and negative controls (mismatch template or no template). After addition of template nucleic acid each well was overlayed with 15 µL of mineral oil and centrifuged briefly. Prior to running the PCR reaction, the assay plate was scanned for intensity of the fluorescent signal to establish baseline fluorescence at 530 and 580 nm.

The following PCR parameters were used:

| Cycle # | Step | Temp | Time |
|---|---|---|---|
| 1. | 1 | 95° C. | 5 min. |
| 2-38. | 1 | 95° C. | 1 sec. |
| | 2 | 58° C. | 1 sec. |
| 39 | 1 | 49° C. | 60 min. |
| 40. | 1 | 4° C. | hold |

Following PCR cycling reactions, the assay plates were tested for emissions of a fluorescence signal. The assay plates were transferred to Cytofluor™ 4000 fluorescence plate reader (Applied Biosystems, Foster City, Calif.) with the instrument set to read from the top of the plate. The parameters for the plate reader were as follows: (6FAM fluorescence detection) excitation filter settings at 485±10 nm; emission filter settings at 530±12.5 nm, and PMT gain set to 50, (HEX fluorescence detection) excitation filter settings at 530±12.5 nm; emission filter to 580±25 nm and PMT gain set to 50.

Example 13

Multiplex PCR Analysis of Factor V Genotype

Multiplexed fluorescence-based PCR reactions were performed to determine allele-specific nucleotide variations in the Factor V gene of human genomic DNA. The procedure used in this example is similar to the procedure used in Example 12.

| Nucleic acid component | Sequence | SEQ ID NO: |
|---|---|---|
| Reporter A | 5'-HEX-TYQGGACAGACG-3' | SEQ ID NO:31 |
| Reporter B | 5'-FAM-TYQCCTGTCTGC-3' | SEQ ID NO:1 |
| First Primer | 5'-ATTTCTGAAAGGTTACTTCAAGGACA-3' | SEQ ID NO:35 |
| Second Primer A | 3'-ACGGACAGGTCCCTAGAYXACCTGTCTGCCTGT-5' | SEQ ID NO:36 |
| Second primer B | 3'-GCGGACAGGTCCCTAGYXAGGACAGACGGACA-5' | SEQ ID NO:37 |
| Template 1 | Synthetic Factor V wild type target; 5'-ATTTCTGAAAGGTTACTTCAAGGACAAAATACCTG TATTCCTCGCCTGTCCAGGGATCTGCTCTTACAGA-3' | SEQ ID NO:38 |
| Template 2 | Synthetic Factor V mutant target; 5'-ATTTCTGAAAGGTTACTTCAAGGACAAAATACCTG TATTCCTTGCCTGTCCAGGGATCTGCTCTTACAGA-3' | SEQ ID NO:39 |
| Template 3 | Human genomic DNA including Factor V wild type target | |
| Template 4 | Human genomic DNA including Factor V mutant target | |

Synthetic Factor V targets were prepared by automated DNA synthesis. Human genomic DNA including Factor V targets was obtained from the Cornell/NIGMS Human Genetic Cell Repository (Camden, N.J.). All gDNA samples were diluted to 1 or 5 ng/µL in 1 mM MOPS pH 7.5, 0.1 mM EDTA and boiled 5 min then placed on ice prior to PCR. Synthetic targets were serially diluted to 1 or 10 fM in 1 mM Tris pH 8.0 (Fisher Scientific, Pittsburgh, Pa.) and 0.1 µg/mL Herring Sperm DNA (St. Louis, Mo.).

| Component | 1X Conc. | Supplier and location |
|---|---|---|
| Bis-Tris-Propane pH 8.9 | 10 mM | Sigma, St. Louis, MO |
| Potassium acetate | 40 mM | Sigma, St. Louis, MO |
| MgCl₂ | 2.5 mM | Sigma, St. Louis, MO |
| AmpliTaq ™ DNA polymerase | 0.5 U/rxn | Applied Biosystems, Foster City, CA |
| dATP | 50 µM | Promega, Madison, WI |
| dGTP | 50 µM | Promega, Madison, WI |
| dCTP | 50 µM | Promega, Madison, WI |
| dTTP | 50 µM | Promega, Madison, WI |
| First Primer | 0.4 µM | |
| Second Primer A | 0.4 µM | |
| Second Primer B | 0.2 µM | |
| Reporter A | 0.4 µM | |
| Reporter B | 0.4 µM | |

A Master Mix containing components listed above was prepared at a 2× concentration for a final reaction volume of 10 µL. 5 µl of the Master Mix was aliquoted to individual wells of an assay plate (Low Profile Multiplate™, 96 well; MJ Research, Waltham, Mass.) and 5 µl of target DNAs were added to individual wells. 5 or 50 zmol (approximately 3000 or 30,000 molecules) of mutant, wild type, or heterozygous synthetic targets were added to the wells. 5 or 25 ng of heterozygous, or wild type human genomic DNA were added to the wells. Wells containing no target DNA were used as controls. After addition of template nucleic acid each well was overlayed with 15 µl of mineral oil and centrifuged briefly. Prior to running the PCR reaction, the assay plate was scanned for intensity of the fluorescent signal to establish baseline fluorescence at 530 nm and 580 nm.

The following PCR parameters were used:

| Cycle # | Step | Temp | Time |
|---|---|---|---|
| 1. | 1 | 95° C. | 5 min. |
| 2-38. | 1 | 95° C. | 1 sec. |
| | 2 | 58° C. | 1 sec. |
| 39 | 1 | 49° C. | 60 min. |

Figure 22:
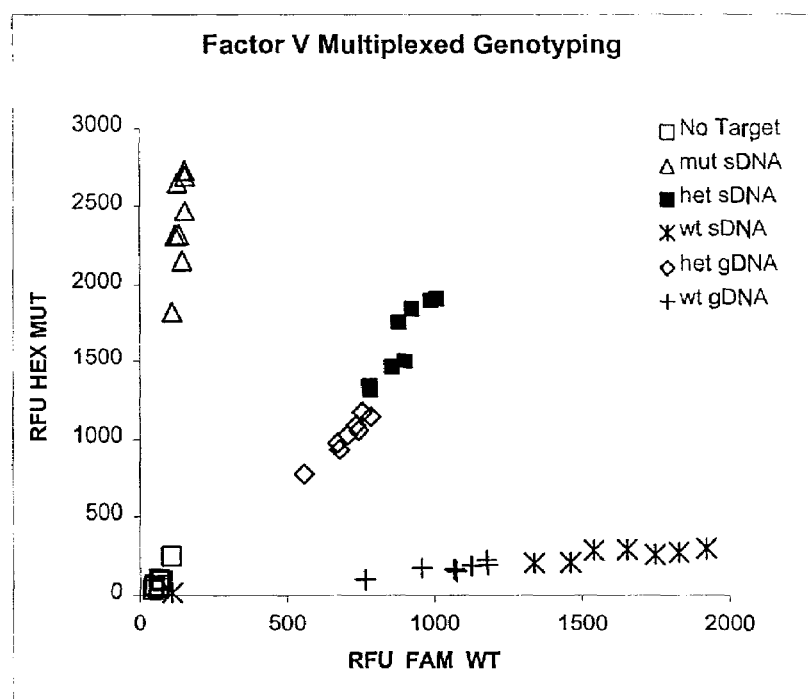
FIG. 22 is a graph demonstrating the combined results from the multiplex PCR analysis of wild type, mutant, and heterozygous Factor V DNA targets; HEX fluorescence RFUs are shown on the Y axis and FAM fluorescence RFUs are shown on the X axis.

Following PCR cycling reactions, the assay plates were tested for emissions of a fluorescence signal. The assay plates were transferred to Cytofluor™ 4000 fluorescence plate reader (Applied Biosystems, Foster City, Calif.) with the instrument set to read from the top of the plate. The parameters for the plate reader were as follows: (6FAM fluorescence detection) excitation filter settings at 485±10 nm; emission filter settings at 530±12.5 nm, and PMT gain set to 50, (HEX fluorescence detection) excitation filter settings at 530±12.5 nm; emission filter to 580±25 nm and PMT gain set to 50. The relative fluorescence units (RFUs) for HEX and FAM fluorescence, shown on the Y and X axes, respectively, for each multiplex PCR reaction performed are combined and shown in FIG. 22.

Example 14

Multiplexed Real Time Allele Specific PCR Using Exonuclease Deficient Nucleic Acid Polymerase and a Flap Endonuclease as a Cleaving Agent Multiplexed fluorescence-based PCR reactions were performed to the sequence of a single nucleotide polymorphism in the mouse STS sequence 27.MMHAP25FLA6 of genomic DNA from various mouse strains. In this example, the multiplexed PCR reaction included a common first primer that hybridized to a downstream non-polymorphic sequence on the target nucleic acid and two upstream second primers, second primer A and second primer B, each second primer being allele-specific where the specificity was determined by different 3' nucleotides. Second primer A and second primer B also had different 5' regions, which did not contribute to target nucleic acid hybridization but allowed for hybridization of reporter A and reporter B, respectively. The reporter nucleic acids each contained a 5'-penultimate non-standard nucleotide and a fluorescence quenching compound-coupled nucleotide but contained 5' nucleotides with different fluorophores (either FAM or HEX) coupled to the 5' nucleotide. The different fluorophores emitted different wavelengths of light upon excitation. Annealing of the reporter nucleic acid to the amplification product, including pairing of the non-standard nucleotides, can cause the cleavage of the fluorophore or fluorophores from the quenching compound-coupled reporter nucleic acid by flap endonuclease-1 (FEN-1) enzyme activity. The predominance of an allele-specific nucleic acid target will result in particular fluorescence emission of the fluorophore from the cleaved reporter.

The following nucleic acids were used in RT-PCR reactions for this example:

| Nucleic acid component | Sequence | SEQ ID NO |
|---|---|---|
| Reporter A | 5'-HEX-TYQGGACAGACGGACA-3' | SEQ ID NO:31 |
| Reporter B | 5'-FAM-TYQCCTGTCTGCCTGT-3' | SEQ ID NO:1 |
| First Primer | 3'-CAGTGACTGGCTGACGAG-5' | SEQ ID NO:32 |
| Second Primer A | 5'<u>TGTCCGTCTGTCCAXY</u>GAGCTAGCGGAGGCC-3' | SEQ ID NO:40 |
| Second primer B | 5'<u>ACAGGCAGACAGGAXY</u>GGAGCTAGCGGAGGCT-3' | SEQ ID NO:41 |
| Template 1 | Mouse genomic DNA; Strain: A/J± (target: 27.MMHAP25FLA6.seq located on mouse chromosome 2: seq. variation: 'CC') | |
| Template 2 | Mouse genomic DNA; Strain: AB6F1** (target: 27.MMHAP25FLA6.seq located on mouse chromosome 2: seq. variation: 'CT') | |
| Template 3 | Mouse genomic DNA; Strain: C57BL/6J± (target: 27.MMHAP25FLA6.seq located on mouse chromosome 2: seq. variation: 'TT') | |

±= inbred strains.
**= F1 hybrid strains.

Mouse gDNA samples were purchased from Jackson Laboratories (Bar Harbor, Me.). All gDNA samples were diluted to 20 ng/μL in 1 mM MOPS pH 7.5, 0.01 mM EDTA and heated to 95 degrees C. for 5 minutes and snap cooled on ice.

| Component | 1X Conc. | Supplier and location |
|---|---|---|
| Bis-Tris-Propane pH 8.9 | 10 mM | Sigma, St. Louis, MO |
| Potassium acetate | 40 mM | Sigma, St. Louis, MO |
| MgCl$_2$ | 2 mM | Sigma, St. Louis, MO |
| dATP | 50 μM | Promega, Madison, WI |
| dGTP | 50 μM | Promega, Madison, WI |
| dCTP | 50 μM | Promega, Madison, WI |
| dTTP | 50 μM | Promega, Madison, WI |
| First Primer | 0.2 μM | |
| Second Primer A | 0.2 μM | |
| Second Primer B | 0.15 μM | |
| Reporter A | 0.2 μM | |
| Reporter B | 0.2 μM | |
| Mja FEN-1 *Methanococcus jannaschii* | 25.1 fmol/rxn | |
| Platinum ™ GenoTYPE ™ Tsp DNA Polymerase | 1.0 U/rxn | Life Technologies, Rockville, MD |

Mja FEN-1 was expressed and purified according to the method described in Hosfield et al., J Biol Chem (1998) 273:27154-61, herein incorporated by reference, with modifications. The GenBank accession number containing the Mja FEN-1 sequence is U67585. Mja FEN-1 is described in U.S. Pat. No. 5,843,669, and Bult et al., Science (1996) 273:1058-1073, both herein incorporated by reference. The plasmid containing the *Methanococcus jannaschii* FEN-1 genes was transformed into the *E. coli* strain BL21 (DE3) (Novagen, Madison, Wis.), and protein overexpression was induced in log phase by addition of isopropylthiogalactopyranoside (Sigma, St. Louis, Mo.) to a final concentration of 0.4 mM. Following growth for an additional 2 hours the cells were pelleted at 3000×g, resuspended in Buffer 1 (10 mM Tris, pH7.5 (Fisher Scientific, Pittsburgh, Pa.), 150 mM NaCl (Sigma, St. Louis, Mo.), 10 mM Imidazole (Aldrich, Milwaukee, Wis.)), sonicated briefly, and lysed by heating at 75° C. for 45 minutes, and then cooled rapidly to 0° C. on ice. This protocol lysed the cells and precipitated the majority of the contaminating mesophilic native *E. coli* proteins. The resulting solution was centrifuged at 25,000×g, and the supernatant was associated with TALON™ Metal Affinity Resin (Clontech, Palo Alto, Calif.) pre-equilibrated with Buffer 1, loaded into a gravity flow column, and washed extensively with Buffer 1. FEN-1 was then eluted using Buffer 1 adjusted to contain a stepwise imidazole gradient of 100 mM, 200 mM, 350 mM and 500 mM. FEN-1 containing fractions were collected and dialyzed extensively against a buffer containing 10 mM Tris, pH 7.5 (Fisher Scientific, Pittsburgh, Pa.), 150 mM KCl, and 1 mM EDTA. Dialyzed material was adjusted to 50% glycerol (Fisher Scientific, Pittsburgh, Pa.), 0.5% Tween®20 (EM Sciences, Gibbstown, N.J.), and 0.5% Nonidet™ P-40 (Roche, Indianapolis, Ind.).

A Master Mix containing components listed above was prepared to be 1.5× the above final concentrations. 15 μl of these mixes were aliquoted to individual wells of an assay plate and 5 μL of target DNAs (100 ng) were added to individual wells and mixed by aspiration. PCR reactions were prepared for positive controls (perfect match template), negative controls (mismatch template or no template), and heterozygous sample (match and mismatch template). After template nucleic acid addition, each well was overlaid with 20 μL of mineral oil and centrifuged briefly.

The assay plates were transferred to the iCycler iQ Real Time PCR Detection System (BioRad, Hercules, Calif.) and cycled using the parameters listed above. The filter sets used for signal detection included: (6FAM)-excitation filter 490±10 nm, emission filter 530±15 nm; (HEX) excitation filter 530±15 nm, emission filter 575±10 nm.

The following PCR parameters were used:

| Cycle # | Step | Temp | Time |
|---|---|---|---|
| 1. | 1 | 95° C. | 3 min. |
| 2-26. | 1 | 95° C. | 1 sec. |
|  | 2 | 59° C. | 1 sec. |
| 27-41 | 1 | 95° C. | 1 sec. |
|  | 2* | 59° C. | 2 min. |
| 42 | 1 | 4° C. | hold |

Figure 23A:
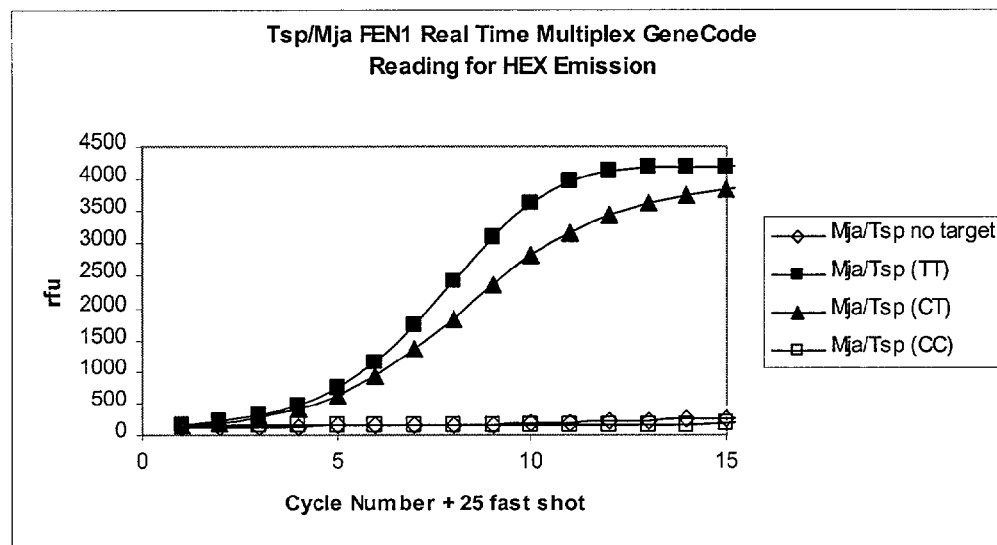
FIGS. 23A-B are graphs demonstrating the combined results from the multiplex PCR analysis of polymorphisms in mouse STS sequence 27.MMHAP25FLA6 of genomic DNA from various mouse strains; PCR cycle number is indicated on the X axis.
Figure 23B:
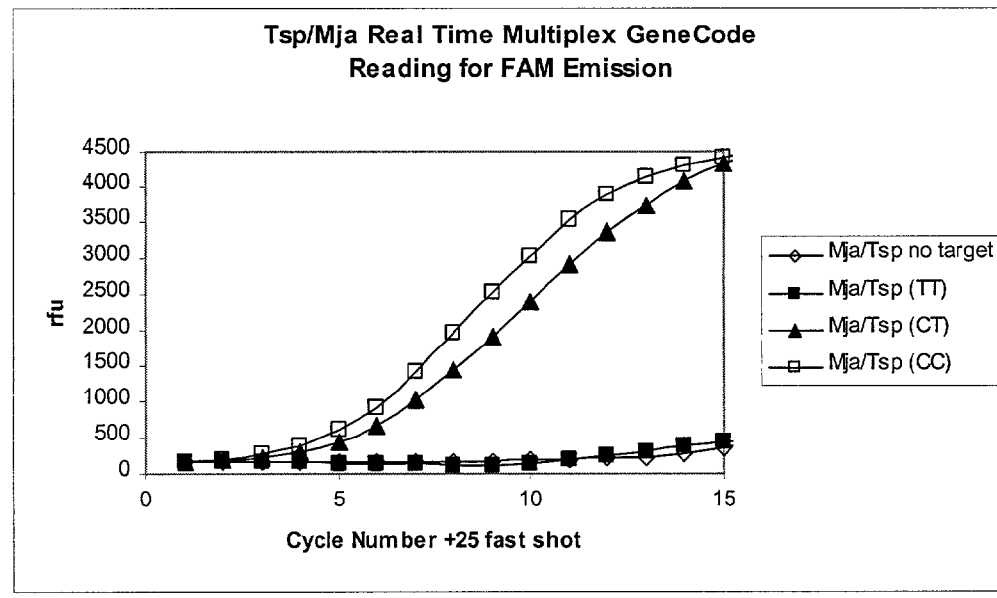

*During Step 2 of cycle #27-42 the optics of the iCycler iQ ™ Real Time PCR Detection System were activated to read FAM and HEX generated fluorescence, allowing determination of the fluorescence in the PCR reaction tube in order to generate a kinetic plot. The results are shown in FIG. 23A-B.

Example 15

Melt Curve Analysis of Fluorescence-quenched PCR Amplification Products and Fluorescence-quenched PCR Amplification Products Melting curve analysis of PCR reaction products containing fluorophores quenched by SSI with a quenching compound can be used to examine the presence of quencher-incorporated primer/dimers. Quencher-incorporated primer/dimers typically melt at temperature lower than quencher-incorporated PCR products. Melt curve analysis can show fluorescence increases at the melting point of the quencher-incorporated primer/dimers and quencher-incorporated PCR products if both are present as products following PCR amplification.

Figure 24:
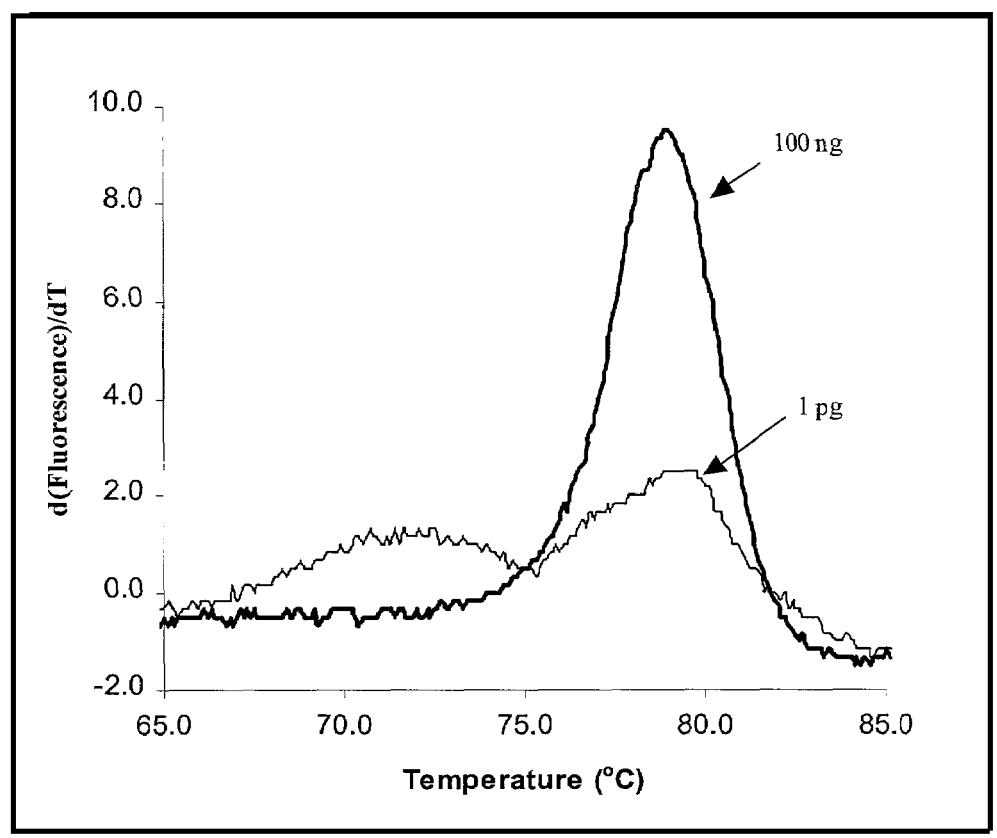
FIG. 24 is a melt curve analysis of the PCR products from a reaction amplifying different amounts of reverse-transcribed RNA by site specific incorporation of a quenching compounds; the change in fluorescence over time is indicated on the Y axis and melting temperature is indicated on the X axis.

PCR amplification products from Example 11 were subjected to melt curve analysis using the Smart Cycler™ (Cepheid, Sunnyvale, Calif.). The change in fluorescence was monitored while gradually increasing the temperature of the PCR reaction products at a rate of 0.1° C. per second. The Tm of the intended product (quencher-incorporated PCR product) as well as that of the nonspecific product (quencher-incorporated primer/dimers) is illustrated in FIG. 25. The melt analysis for a RT-PCR reaction containing a starting quantity of 1 pg of RNA template showed a significant amount of nonspecific product with a Tm of approximately 71° C. as well as an intended product Tm of approximately 79° C. The melt analysis for a reaction containing 100 ng of RNA template showed only the formation the intended product with a Tm of 79° C. Once the Tm of the intended product is known it is conceivable that in order to specifically observe the signal generated by the intended product by taking the fluorescent measurement of the reaction at a temperature above the Tm of the nonspecific product, it may be useful to observe, and below that of the intended product. The results from the melt curve analysis are shown in FIG. 24.

We claim:

1. A method of detecting a target nucleic acid in a sample, the method comprising:
    a) contacting the sample with a nucleic acid polymerase; a first oligonucleotide primer comprising a sequence complementary to a first portion of the target nucleic acid; a second oligonucleotide primer comprising a first region and a second region, the first region comprising a sequence complementary to a second portion of the target nucleic acid and the second region comprising a non-natural base;
    b) amplifying the target nucleic acid, if present in the sample, using the first and second oligonucleotide primers in the presence of a labeled reporter to generate an amplification product, wherein the labeled reporter comprises a non-natural base which is incorporated into the amplification product opposite the non-natural base present in the second region of the second oligonucleotide primer; and
    c) observing a signal from the labeled reporter during amplification and correlating the incorporating of the reporter with the presence of the target nucleic acid in the sample.

2. The method of claim 1, wherein the labeled reporter comprises a nucleotide triphosphate of the non-natural base.

3. The method of claim 1, wherein the labeled reporter consists essentially of a nucleotide triphosphate of the non-natural base and the label.

4. The method of claim 1, wherein the label comprises a fluorophore.

5. The method of claim 1, wherein the second region of the second oligonucleotide primer further comprises a label and the labels of the reporter and the second region of the second oligonucleotide primer comprises a signal generating/signal quenching pair.

6. The method of claim 1, wherein the second region of the second oligonucleotide primer further comprises a label and the labels of the reporter and the second region of the second oligonucleotide primer comprise a pair of fluorophores where the emission of one of the fluorophores stimulates the emission of the other fluorophore.

7. The method of claim 1, wherein the second region of the second oligonucleotide primer comprises at least one additional base.

8. The method of claim 5 wherein the label of the reporter comprises a quencher.

9. The method of claim 1 wherein (c) comprises determining the melting temperature of the amplification product.

10. The method of claim 1 wherein (c) comprises monitoring fluorescence of the amplification during target nucleic acid amplification.

11. The method of claim 5 wherein the label of the second region of the second oligonucleotide primer comprises interactive labels.

12. The method of claim 1 wherein the amplification reaction comprises several different primers.

13. The method of claim 1 wherein the amplification reaction comprises a multiplex amplification reaction.

14. The method of claim 1 wherein the first oligonucleotide primer comprises a non-natural base.

15. A method of detecting a target nucleic acid in a sample, the method comprising:
    a) amplifying the target nucleic acid, if present in the sample, to provide an amplification product, wherein at least one primer used for amplifying the target nucleic acid comprises a first non-natural base;
    b) incorporating a reporter into the amplification product during amplification, wherein the reporter comprises a label and a second non-natural base that base-pairs with the first non-natural base; and
    c) observing a signal from the label during amplification thereby detecting and quantifying the target nucleic acid.

16. A method of detecting a target nucleic acid in a sample, the method comprising:
    a) reacting a mixture that comprises:
        (i) the sample;
        (ii) a first oligonucleotide primer comprising a sequence complementary to the target nucleic acid;

(iii) a second oligonucleotide primer comprising a sequence complementary to the target nucleic acid and a first non-natural base; and (iv) a reporter comprising a label and a second non-natural base that base-pairs with the first non-natural base;

b) amplifying the target nucleic acid, if present in the sample, to generate an amplification product, wherein the reporter is incorporated into the amplification product; and c) observing a signal from the label during amplification thereby detecting and quantifying the target nucleic acid.

\* \* \* \* \*

UNITED STATES PATENT AND TRADEMARK OFFICE
CERTIFICATE OF CORRECTION

| | | |
|---|---|---|
| PATENT NO. | : 7,422,850 B2 | Page 1 of 1 |
| APPLICATION NO. | : 09/861292 | |
| DATED | : September 9, 2008 | |
| INVENTOR(S) | : Marshall et al. | |

It is certified that error appears in the above-identified patent and that said Letters Patent is hereby corrected as shown below:

On the Title Page:

The first and sole Notice should read --

Subject to any disclaimer, the term of this patent is extended or adjusted under 35 U.S.C. 154(b) by 519 days.

Signed and Sealed this

Twenty-first Day of September, 2010

David J. Kappos
*Director of the United States Patent and Trademark Office*